(12) United States Patent
Murai et al.

(10) Patent No.: US 12,202,800 B2
(45) Date of Patent: Jan. 21, 2025

(54) METHOD FOR PRODUCING AMINO ACID DERIVATIVES

(71) Applicant: API CORPORATION, Fukuoka (JP)

(72) Inventors: Masato Murai, Tokyo (JP); Jun Takehara, Tokyo (JP); Daiki Okado, Tokyo (JP)

(73) Assignee: API CORPORATION, Fukuoka (JP)

( * ) Notice: Subject to any disclaimer, the term of this patent is extended or adjusted under 35 U.S.C. 154(b) by 0 days.

(21) Appl. No.: 18/243,409

(22) Filed: Sep. 7, 2023

(65) Prior Publication Data

US 2024/0002340 A1 Jan. 4, 2024

Related U.S. Application Data

(62) Division of application No. 17/277,456, filed as application No. PCT/JP2019/037399 on Sep. 24, 2019, now Pat. No. 11,897,844.

(30) Foreign Application Priority Data

Sep. 21, 2018 (JP) .................. 2018-177774

(51) Int. Cl.
    *C07D 211/60* (2006.01)
(52) U.S. Cl.
    CPC ................ *C07D 211/60* (2013.01)
(58) Field of Classification Search
    None
    See application file for complete search history.

(56) References Cited

U.S. PATENT DOCUMENTS 9,120,795 B2 * 9/2015 Hwang ................ C07D 471/08
11,897,844 B2 * 2/2024 Murai .................. C07D 211/60
(Continued)

FOREIGN PATENT DOCUMENTS

CN 105061425 A 11/2015
EP 3 281 942 A1 2/2018
(Continued)

OTHER PUBLICATIONS

International Union of Pure and Applied Chemistry, Compendium of Chemical Terminology (IUPAC), Gold Book, p. 828 of 1622 (2014) (Year: 2014).*
(Continued)

*Primary Examiner* — Alexander R Pagano
(74) *Attorney, Agent, or Firm* — GREENBLUM & BERNSTEIN, P.L.C.

(57) ABSTRACT

A method for producing a compound represented by the formula (1):

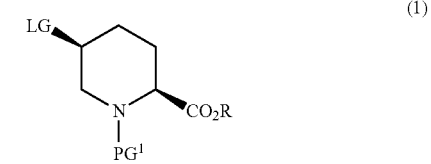

(1)

wherein LG is a leaving group, $PG^1$ is an amino-protecting group, and R is a hydrocarbon group having 1-8 carbon atoms and optionally having substituent(s), comprising
    reacting a compound represented by the formula (6):

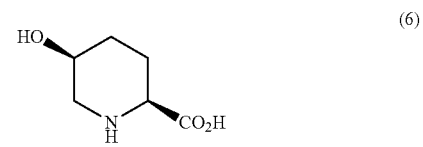

(6)

with an amino group protecting agent to obtain a compound represented by the formula (7):

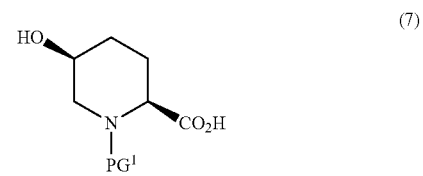

(7)

or a salt thereof;
    reacting the aforementioned compound represented by the formula (7) with a lactonization agent to obtain a compound represented by the formula (8):

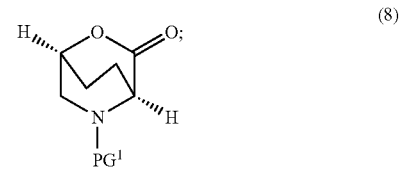

(8)

reacting the aforementioned compound represented by the formula (8) with an esterification agent to obtain a compound represented by the formula (9):

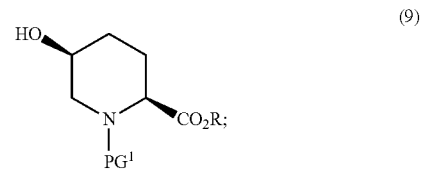

(9)

and (Continued)

reacting the aforementioned compound represented by the formula (9) with a leaving group introduction agent.

3 Claims, No Drawings

(56) References Cited

U.S. PATENT DOCUMENTS

| | | |
|---|---|---|
| 2011/0294777 A1 | 12/2011 | Blizzard et al. |
| 2012/0053350 A1 | 3/2012 | Mangion et al. |
| 2013/0274475 A1 | 10/2013 | Mangion et al. |
| 2014/0275001 A1* | 9/2014 | Hwang ............... C07D 471/08 546/121 |
| 2015/0031659 A1 | 1/2015 | Gu |
| 2015/0038478 A1 | 2/2015 | Gu |
| 2015/0141401 A1 | 5/2015 | Abe et al. |
| 2015/0239906 A1* | 8/2015 | Maeda ................. C12P 17/12 546/242 |
| 2016/0122350 A1* | 5/2016 | Miller ................. C07D 401/12 546/121 |
| 2016/0318867 A1* | 11/2016 | Takehara ............ C07D 498/08 |
| 2017/0218353 A1* | 8/2017 | Petter ................. C07D 401/04 |
| 2024/0150292 A1* | 5/2024 | Murai ................. C07D 211/60 |

FOREIGN PATENT DOCUMENTS

| | | | | |
|---|---|---|---|---|
| WO | 2009/091856 A1 | 7/2009 | | |
| WO | 2010/126820 A1 | 11/2010 | | |
| WO | WO-2013149121 A1 * | 10/2013 | ........... | A61K 31/407 |
| WO | WO-2013180197 A1 * | 12/2013 | ........... | A61K 31/407 |
| WO | 2014/200786 A1 | 12/2014 | | |
| WO | 2015/173779 A1 | 11/2015 | | |
| WO | 2017/098425 A1 | 6/2017 | | |
| WO | 2017/167218 A1 | 10/2017 | | |
| WO | 2018/060926 A1 | 4/2018 | | |
| WO | 2019/122438 A1 | 6/2019 | | |

OTHER PUBLICATIONS

J. Shilvock et al., 9 Tetrahedron: Asymmetry, 4157-4164 (1998) (Year: 1998).*
D. Constable et al., 9 Green Chem., 411-420 (2007) (Year: 2007).*
S. Miller et al., 16 Organic Letters, 174-177 (2014) (Year: 2014).*
P. Bailey et al., 29 Tetrahedron Letters, 2231-2234 (1988) (Year: 1988).*
S. Hoarau et al., 7 Tetrahedron Asymmetry, 2585-2593 (1996) (Year: 1996).*
J. Jung et al., 17 Tetrahedron Asymmetry, 2479-2486 (2006) (Year: 2006).*
Sulsky, R. et al., "Alkylation of N-benzyloxyureas and carbamates," Tetrahedron Letters, 1989, vol. 30, No. 1, pp. 31-34, ISSN: 0040-4039.
Mangion, I. K. et al., "A concise synthesis of a B-lactamase inhibitor," Organic Letters, 2011, vol. 13, No. 20, pp. 5480-5483, ISSN: 1523-7052.
ISR issued in International Patent Application No. PCT/JP2019/037399, Dec. 10, 2019, English translation.
Written Opinion issued in Int'l Patent Application No. PCT/JP2019/037399, Dec. 10, 2019, English translation.
Supplementary partial EESR issue in EP Patent Application No. 19863035.2, May 13, 2022.
Edoo et al. "Synthesis of Avibactam Derivatives and Activity on β-Lactamases and Peptidoglycan Biosynthesis Enzymes of Mycobacteria", Chemistry—A European Journal, vol. 24, No. 32, 2018, 8081-8086.
Reasons for Refusal issued in JP Patent Application No. 2020-549244, Oct. 2, 2023, translation.
Lafrance et al., "New Synthetic Route to a Dipeptidyl Peptidase-4 Inhibitor", Org. Lett. 2011, v. 13, pp. 5480-5483.
European Search Opinion in EP 19863035, Aug. 18, 2022.
T. Allman et al., Canadian Journal of Chemistry, pp. 716-722 (1982).
R. Sanders et al., J.C.S. Dalton, pp. 743-747 (1973).
C. Hansch et al., 91 Chemical Reviews, pp. 165-195 (1991).
A. Debache et al., 49 Tetrahedron Letters, pp. 6119-6121 (2008).
J. March, Advanced Organic Chemistry Reaction, Mechanisms and Structure (1992) pp. 248-272.
Office Action issued in EP Patent Application No. 19863035.2, Dec. 1, 2023.

* cited by examiner

METHOD FOR PRODUCING AMINO ACID DERIVATIVES

This application is a Divisional of U.S. patent application Ser. No. 17/277,456, filed Mar. 18, 2021, which is a National Stage Entry of International Patent Application No. PCT/JP2019/037399, filed Sep. 24, 2019, and claims the benefit of priority of Japanese Application 2018-177774, filed Sep. 21, 2018. The entire contents of each of the above-mentioned documents is expressly incorporated by reference herein in its entirety.

TECHNICAL FIELD

The present invention relates to a method for producing a (2S,5R)-5-(protected oxyamino)-piperidine-2-carboxylic acid derivative, a synthetic intermediate therefor or a salt thereof.

BACKGROUND ART

β-lactam antibiotics such as penicillin antibiotics, cephem antibiotics, monobactam antibiotics, carbapenem antibiotics and the like are widely used for the treatment and prophylaxis of bacterial infections. However, β-lactamase (enzyme that hydrolyzes the β-lactam ring) produced by bacteria reduces or inactivates the antibacterial activity of β-lactam antibiotics, and decreased therapeutic and prophylactic effects of β-lactam antibiotics against bacterial infections often poses problems.

Thus, various β-lactamase inhibitors that, in combination with β-lactam antibiotics, exert their original antibacterial action against bacteria that are resistant to β-lactam antibiotics, and the production methods thereof have been developed.

A (2S,5R)-5-(protected oxyamino)-piperidine-2-carboxylic acid derivative is known as an intermediate useful for synthesizing β-lactamase inhibitors such as diazabicyclooctane derivative and the like.

As a production method of the (2S,5R)-5-(protected oxyamino)-piperidine-2-carboxylic acid derivative, the production methods described in patent document 1 and patent document 2 are known.

Specifically, patent document 1 describes a production method of a (2S,5R)-5-(benzyloxyamino)-piperidine-2-carboxylic acid derivative which includes synthesizing N-trifluoroacetyl-acid alkyl ester using (2S,5S)-5-hydroxypiperidine-2-carboxylic acid as a starting material and via esterification and N-trifluoroacetyl protection, then introducing a trifluoromethanesulfonyl group as a leaving group into the 5-position hydroxyl group, and reacting same with O-benzylhydroxylamine.

In addition, patent document 2 describes a production method of ethyl (2S,5R)-5-(benzyloxyamino)piperidine-2-carboxylate which includes synthesizing 2-ethyl (S)-1-tert-butyl-5-oxopiperidine-1,2-dicarboxylate using ethyl (S)-1-(tert-butyloxycarbonyl)-5-oxopyrrolidine-2-carboxylate as a starting material, reducing the 5-position carbonyl group to synthesize 2-ethyl (2S,5S)-1-tert-butyloxycarbonyl-5-hydroxypiperidine-1,2-dicarboxylate, introducing a leaving group into the 5-position, reacting same with N-(benzyloxy)-2-nitrobenzenesulfonamide, and deprotecting nitrobenzenesulfonyl group and tert-butyloxycarbonyl group.

DOCUMENT LIST

Patent Documents patent document 1: WO 2013/180197
patent document 2: U.S. Pat. No. 9,120,795

SUMMARY OF INVENTION

Technical Problem

However, the above-mentioned prior art relating to the synthetic intermediates of β-lactamase inhibitors had many technical problems below.

In the production method of patent document 1, since many of the starting materials to be used and the intermediates to be produced include are extremely unstable and require extremely low temperature conditions, the production is possible only with equipment that can be used under extremely low temperature conditions. In addition, since many of the intermediates to be produced are oily, purification by crystallization is difficult and handling at the site of production is not easy. Furthermore, since the N-protecting group of the intermediate to be produced is a protecting group with high electron-withdrawing property, isomerization at the 2-position is likely to occur. Thus, the quality control is difficult and the quality of the desired product is easily degraded. In addition, expensive solvents and leaving group introduction agents are required.

Therefore, a less expensive industrial production method that can be performed under mild reaction conditions not requiring a facility at an extremely low temperature, shows good workability in the site of production, and can control the quality of the desired product with ease is desired.

The production method of patent document 2 requires expensive solvents and reagents, and does not show high yield of the intermediate. In addition, diethyl azodicarboxylate to be used as the reagent may cause a large amount of heat generation or explosive reaction due to self-reaction during heating or decomposition, which may lead to a runaway reaction. Furthermore, since post-treatment and removal of triphenylphosphine oxide, which is a by-product, is difficult, it is not easy to control the quality of the desired product.

Therefore, an industrial production method that is less expensive, is safer, and can control the quality of the desired product with ease is desired.

As described above, in the production methods of a (2S,5R)-5-(protected oxyamino)-piperidine-2-carboxylic acid derivative useful as a synthesis intermediate for β-lactamase inhibitors, a less expensive industrial production method that can be performed under mild reaction conditions not requiring a facility at an extremely low temperature, is safer, can control the quality of the desired product with ease, and shows good workability in the site of production has been desired.

Solution to Problem

The present inventors have conducted intensive studies and found a method for producing a (2S,5R)-5-(protected oxyamino)-piperidine-2-carboxylic acid derivative at a low cost that can be performed under mild reaction conditions not requiring a facility at an extremely low temperature, is safer, can control the quality of the desired product with ease, and shows good workability in the site of production, and completed the present invention.

That is, the gist of the present invention is as follows.

[1] A method for producing a compound represented by the formula (2):

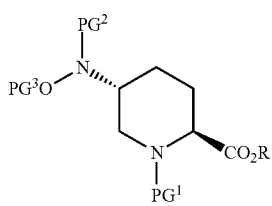

wherein PG$^1$ is an amino-protecting group, PG$^2$ is an amino-protecting group, PG$^3$ is a hydroxyl-protecting group, LG is a leaving group, and R is a hydrocarbon group having 1-8 carbon atoms and optionally having substituent(s), comprising reacting a compound represented by the formula (1):

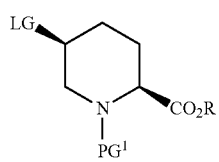

wherein each symbol is as defined above, with a hydroxylamine derivative represented by the formula PG$^2$NHOPG$^3$ wherein each symbol is as defined above in the presence of a base in a solvent.

[2] A method for producing a compound represented by the formula (4):

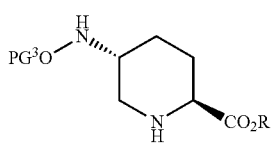

wherein PG$^3$ is a hydroxyl-protecting group, and R is a hydrocarbon group having 1-8 carbon atoms and optionally having substituent(s), or a salt thereof, comprising removing PG$^2$ from a compound represented by the formula (2):

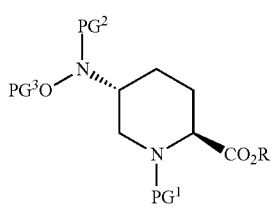

wherein PG$^1$ and PG$^2$ are each independently an amino-protecting group, and other symbols are as defined above, to obtain a compound represented by the formula (3):

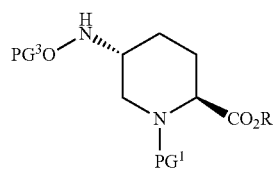

wherein each symbol is as defined above,
or a salt thereof; and
removing PG$^1$ from the aforementioned compound represented by the formula (3).

[3] A method for producing a compound represented by the formula (4):

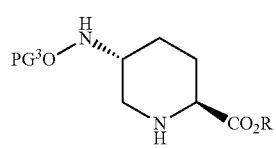

wherein PG$^2$ is a hydroxyl-protecting group, and R is a hydrocarbon group having 1-8 carbon atoms and optionally having substituent(s), or a salt thereof, comprising removing PG$^1$ from a compound represented by the formula (2):

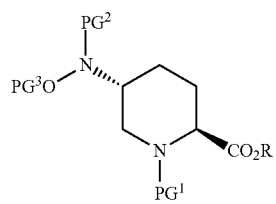

wherein PG$^1$ and PG$^2$ are each independently an amino-protecting group, and other symbols are as defined above, to obtain a compound represented by the formula (5):

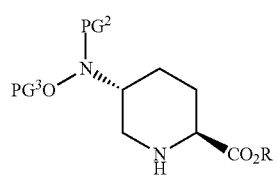

wherein each symbol is as defined above,
or a salt thereof; and
removing PG$^2$ from the aforementioned compound represented by the formula (5) to obtain the compound represented by the formula (4).

[4] A method for producing a compound represented by the formula (1):

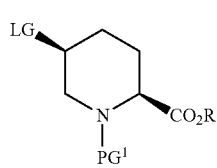

(1)

wherein LG is a leaving group, PG¹ is an amino-protecting group, and R is a hydrocarbon group having 1-8 carbon atoms and optionally having substituent(s), comprising reacting a compound represented by the formula (6):

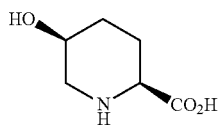

(6)

with an amino group protecting agent to obtain a compound represented by the formula (7):

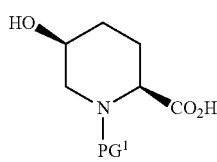

(7)

wherein each symbol is as defined above,
or a salt thereof;
reacting the aforementioned compound represented by the formula (7) with a lactonization agent to obtain a compound represented by the formula (8):

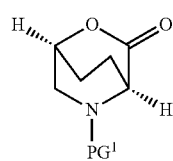

(8)

wherein each symbol is as defined above;
reacting the aforementioned compound represented by the formula (8) with an esterification agent to obtain a compound represented by the formula (9):

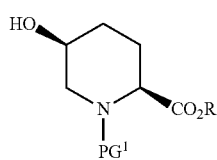

(9)

wherein each symbol is as defined above; and
reacting the aforementioned compound represented by the formula (9) with a leaving group introduction agent.
[5] A method for producing a compound represented by the formula (1):

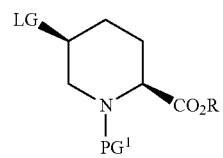

(1)

wherein LG is a leaving group, PG¹ is an amino-protecting group, and R is a hydrocarbon group having 1-8 carbon atoms and optionally having substituent(s), comprising reacting a compound represented by the formula (8):

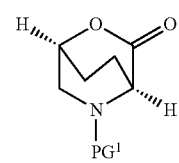

(8)

wherein PG¹ is as defined above, with an esterification agent to give a compound represented by the formula (9):

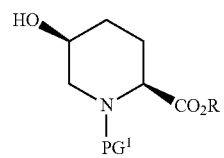

(9)

wherein each symbol is as defined above; and
reacting the aforementioned compound represented by the formula (9) with a leaving group introduction agent.
[6] A method for producing a compound represented by the formula (4):

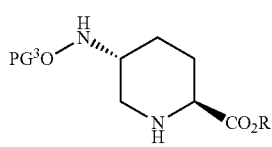

(4)

wherein R is a hydrocarbon group having 1-8 carbon atoms and optionally having substituent(s), and PG³ is a hydroxyl-protecting group,
or a salt thereof, comprising reacting a compound represented by the formula (1):

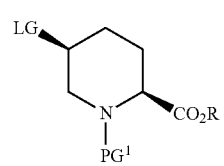

(1)

wherein PG¹ is an amino-protecting group, LG is a leaving group, and R is as defined above, with a hydroxylamine derivative represented by the formula PG²NHOPG³ wherein PG$^2$ is an amino-protecting group and PG$^3$ is as defined above in the presence of a base in a solvent to obtain a compound represented by the formula (2):

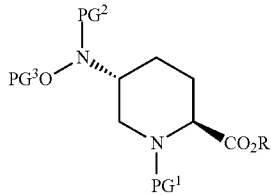
(2)

wherein each symbol is as defined above;
removing PG$^2$ from the aforementioned compound represented by the formula (2) to obtain a compound represented by the formula (3):

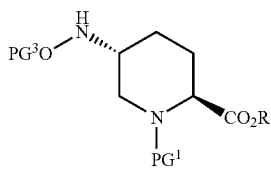
(3)

wherein each symbol is as defined above,
or a salt thereof; and
removing PG$^1$ from the aforementioned compound represented by the formula (3).

[7] A method for producing a compound represented by the formula (4):

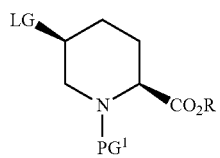
(4)

wherein R is a hydrocarbon group having 1-8 carbon atoms and optionally having substituent(s), and PG$^3$ is a hydroxyl-protecting group,
or a salt thereof, comprising reacting a compound represented by the formula (1):

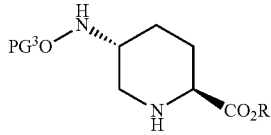
(1)

wherein PG$^1$ is an amino-protecting group, LG is a leaving group, and R is as defined above, with a hydroxylamine derivative represented by the formula PG$^2$NHOPG$^3$ wherein PG$^2$ is an amino-protecting group and PG$^3$ is as defined above in the presence of a base in a solvent to obtain a compound represented by the formula (2):

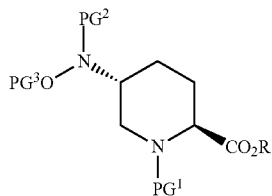
(2)

wherein each symbol is as defined above;
removing PG$^1$ from the aforementioned compound represented by the formula (2) to obtain a compound represented by the formula (5):

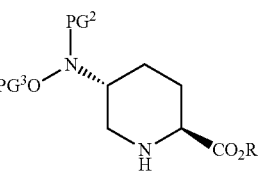
(5)

wherein each symbol is as defined above,
or a salt thereof; and
removing PG$^2$ from the aforementioned compound represented by the formula (5) to obtain the compound represented by the formula (4).

[8] The production method of [1], [6] or [7], wherein PG$^1$ is a carbamate type protecting group or an amide type protecting group, and a $\sigma_p^-$ value thereof is not more than 1.00.

[9] The production method of any one of [1] and [6]-[8], wherein LG is a sulfonyloxy group.

[10] The production method of any one of [1] and [6]-[9], wherein the compound represented by the formula (1) and the hydroxylamine derivative represented by the formula: PG$^2$NHOPG$^3$ wherein PG$^2$ is an amino-protecting group, PG$^3$ is a hydroxyl-protecting group, and other symbols are each as defined above, are reacted at 10° C.-70° C.

[11] A compound represented by the following formula (1a), (1b), (2a), (2b), (3b), (5a) or (9b):

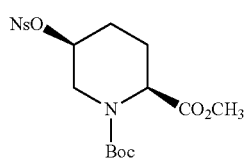
(1a)

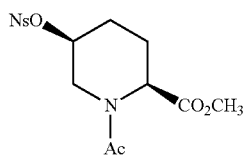
(1b)

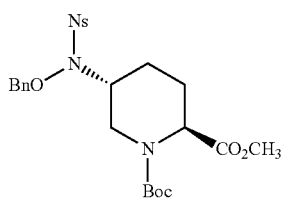
(2a)

-continued

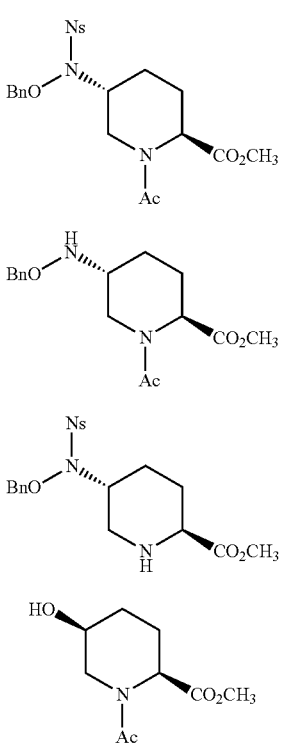

(2b)

(3b)

(5a)

(9b)

wherein Boc is a tert-butoxycarbonyl group, Ac is an acetyl group, Ns is a p-nitrobenzenesulfonyl group, and Bn is a benzyl group.

Advantageous Effects of Invention

According to the present invention, a method for producing a (2S,5R)-5-(protected oxyamino)-piperidine-2-carboxylic acid derivative at a low cost that can be performed under mild reaction conditions not requiring a facility at an extremely low temperature, is safer, can control the quality of the desired product with ease, and shows good workability in the site of production can be provided.

Specifically, the production method of the present invention can produce the desired product with high quality since hydroxylamination can be performed under mild conditions while suppressing isomerization of the 2-position by adopting, as a compound with pipecolic acid as the base structure, a compound in which a leaving group has been introduced into the and an amine-protecting group with low electron-withdrawing property has been introduced into the 1-position. Furthermore, the production method of the present invention can reduce the polarity of the intermediate produced and improve solubility of the intermediate in an organic solvent and crystallization thereof by protection of an amino group and esterification of a carboxyl group. As a result, purification efficiency of the produced intermediate can be improved and workability at the site of production can be improved.

DESCRIPTION OF EMBODIMENTS

The present invention is explained in detail below.

Terms in Description

Respective symbols and terms in the formulas in the present invention are explained below.

$PG^1$ and $PG^2$ are each independently an amino-protecting group.

The amino-protecting group is not particularly limited as long as it protects an amino group and known amino-protecting groups can be mentioned. Preferable examples thereof include carbamate type protecting group, amide type protecting group, and sulfonamide type protecting group.

Examples of the carbamate type protecting group include aliphatic oxycarbonyl groups such as methyloxycarbonyl group, ethyloxycarbonyl group, tert-butyloxycarbonyl group, allyloxycarbonyl group and the like; and aromatic oxycarbonyl groups such as benzyloxycarbonyl group, p-methyloxybenzylcarbonyl group, p-nitrobenzyloxycarbonyl group, 9-fluorenylmethyloxycarbonyl group and the like.

Examples of the amide type protecting group include formyl group, acetyl group, pivaloyl group, benzoyl group, trichloroacetyl group or trifluoroacetyl group and the like. Among these, examples of the amide type protecting group with low electron-withdrawing property include hydrocarbon acyl groups such as acetyl group, pivaloyl group, benzoyl group and the like. Examples of the amide type protecting group with high electron-withdrawing property include halogen substituted hydrocarbon type acyl groups such as trichloroacetyl group, trifluoroacetyl group and the like.

Examples of the sulfonamide type protecting group include hydrocarbon sulfonamide type protecting groups such as methanesulfonyl group, benzenesulfonyl group, p-toluenesulfonyl group, triisopropylbenzenesulfonyl group and the like; and nitrobenzenesulfonamide type protecting groups such as o-nitrobenzenesulfonyl group, p-nitrobenzenesulfonyl group, o,p-dinitrobenzenesulfonyl group and the like.

$PG^3$ is a hydroxyl-protecting group.

As the hydroxyl-protecting group, known hydroxyl-protecting groups can be mentioned. Examples thereof include ether type protecting group, acetal type protecting group, silyl ether type protecting group, and acyl type protecting group.

Examples of the ether type protecting group include chain alkyl ether type protecting groups such as methyl group, ethyl group, normal propyl group, isopropyl group, normal butyl group, sec-butyl group, tert-butyl group and the like; cyclic alkyl ether type protecting groups such as cyclopentyl group, cyclohexyl group and the like; and aromatic ether type protecting groups such as benzyl group, p-methyloxybenzyl group, trityl group and the like.

Examples of the acetal type protecting group include chain acetal type protecting groups such as methyloxymethyl group, methyloxyethyl group, ethyloxymethyl group, ethyloxyethyl group and the like; and cyclic acetal type protecting groups such as tetrahydropyranyl group and the like.

Examples of the silyl ether type protecting group include hydrocarbon type silyl groups such as trimethylsilyl group, triethylsilyl group, tert-butyldimethylsilyl group, triisopropylsilyl group, tert-butyldiphenylsilyl group and the like.

Examples of the acyl type protecting group include hydrocarbon type acyl groups such as acetyl group, pivaloyl group, benzoyl group and the like; and halogen substituted hydrocarbon type acyl groups such as trichloroacetyl group, trifluoroacetyl group and the like.

LG is a leaving group.

As the leaving group, known leaving groups such as sulfonyloxy group, halogen atom and the like can be mentioned.

Examples of the sulfonyloxy group include alkylsulfonyloxy groups such as methanesulfonyloxy group, trichloromethanesulfonyloxy group, trifluoromethanesulfonyloxy group and the like; arylsulfonyloxy groups such as benzenesulfonyloxy group, p-toluenesulfonyloxy group and the like; and nitrobenzenesulfonyloxy groups such as p-nitrobenzenesulfonyloxy group, o-nitrobenzenesulfonyloxy group and the like.

As the halogen atom, fluorine, chlorine, bromine, and iodine can be mentioned.

R is a hydrocarbon group having 1-8 carbon atoms and optionally having substituent(s).

The hydrocarbon group having 1-8 carbon atoms is preferably an aliphatic hydrocarbon group having 1-8 carbon atoms, or an aromatic hydrocarbon group having 6-8 carbon atoms.

Examples of the aliphatic hydrocarbon group having 1-8 carbon atoms include alkyl group having 1-8 carbon atoms, alkenyl group having 2-8 carbon atoms, and alkynyl group having 2-8 carbon atoms, and these may be linear, branched chain or cyclic.

Examples of the aromatic hydrocarbon group having 6-8 carbon atoms include phenyl group, benzyl group, tolyl group, phenylethyl group and the like.

Examples of the "substituent" of the "optionally having substituent(s)" include oxo group, hydroxyl group, alkyl group having 1-8 carbon atoms, alkenyl group having 2-8 carbon atoms, alkynyl group having 2-8 carbon atoms, alkyloxy group having 1-8 carbon atoms, alkenyloxy group having 2-8 carbon atoms, alkynyloxy group having 2-8 carbon atoms, acyl group having 1-8 carbon atoms, acyloxy group having 1-8 carbon atoms, halogen atom and the like. These substituents may be substituted at any substitutable position in any substitutable number.

Examples of the alkyl group having 1-8 carbon atoms include methyl group, ethyl group, propyl group, butyl group, pentyl group, hexyl group, heptyl group, octyl group and isomers thereof.

Examples of the alkenyl group having 2-8 carbon atoms include ethenyl group, propenyl group, butenyl group, pentenyl group, hexenyl group, heptenyl group, octenyl group and isomers thereof.

Examples of the alkynyl group having 2-8 carbon atoms include ethynyl group, propynyl group, butynyl group, pentynyl group, hexynyl group, heptynyl group, octynyl group and isomers thereof.

Examples of the alkyloxy group having 1-8 carbon atoms include methoxy group, ethoxy group, propoxy group, butoxy group, pentyloxy group, hexyloxy group, heptyloxy group, octyloxy group and isomers thereof.

Examples of the alkenyloxy group having 2-8 carbon atoms include ethenyloxy group, propenyloxy group, butenyloxy group, pentenyloxy group, hexenyloxy group, heptenyloxy group, octenyloxy group and isomers thereof.

Examples of the alkynyloxy group having 2-8 carbon atoms include ethynyloxy group, propynyloxy group, butynyloxy group, pentynyloxy group, hexynyloxy group, heptynyloxy group, octynyloxy group and isomers thereof.

Examples of the acyl group having 1-8 carbon atoms include methanoyl group, ethanoyl group, propanoyl group, butanoyl group, pentanoyl group, hexanoyl group, heptanoyl group, octanoyl group and isomers thereof.

Examples of the acyloxy group having 1-8 carbon atoms include methanoyloxy group, ethanoyloxy group, propanoyloxy group, butanoyloxy group, pentanoyloxy group, hexanoyloxy group, heptanoyloxy group, octanoyloxy group and isomers thereof.

As the halogen atom, fluorine, chlorine, bromine, and iodine can be mentioned.

The formula weight of R may be any as long as the bonded compound is substantially dissolved in an organic solvent. The lower limit is not particularly set, but the upper limit is generally not more than 300, preferably not more than 250, more preferably not more than 200, further preferably not more than 150, particularly preferably not more than 100, from the aspect of operability such as solubility in a solvent and the like. For example, the formula weight of methyl group is 15, and the formula weight of benzyl group is 91.

M is a metal atom.

The "metal atom" is a known metal and, for example, alkali metal, alkaline earth metal, and transition metal can be mentioned.

Examples of the alkali metal include lithium, sodium, potassium, rubidium, cesium, and francium.

Examples of the alkaline earth metal include beryllium, magnesium, calcium, strontium, and barium.

Examples of the transition metal include titanium, zirconium, hafnium, vanadium, niobium, tantalum, bismuth, antimony and the like.

M is preferably alkali metal or alkaline earth metal and, from the aspects of the availability and cost of the starting materials, it is more preferably lithium, sodium, potassium, cesium, magnesium, calcium or barium, particularly preferably sodium or potassium.

[Production Routes of the Present Invention]

The production routes A and B of the present invention include the following steps.

Production Routes A and B

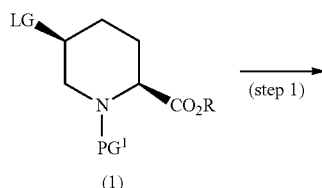

(1)

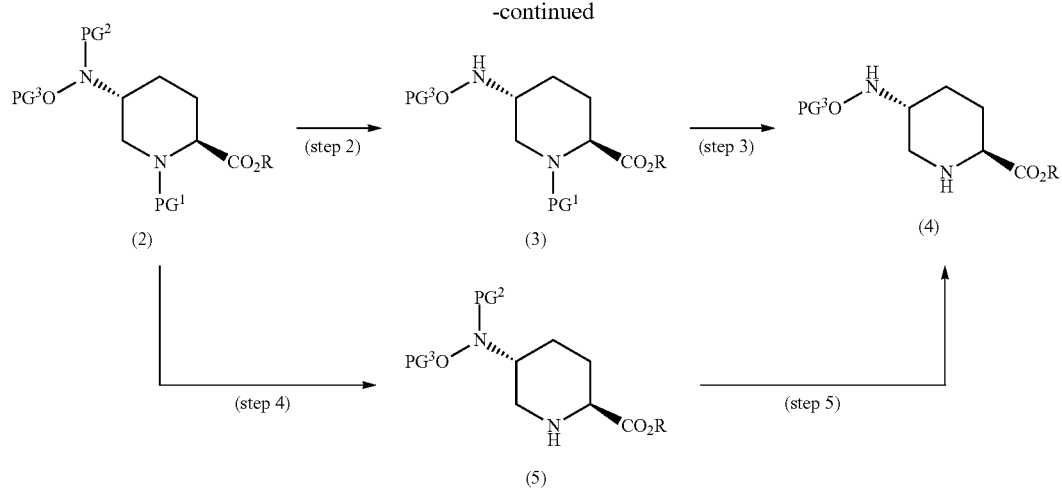

That is, the production routes A and B are methods for producing a compound represented by the formula (4) from a compound represented by the above-mentioned formula (1).

The production route A is a production route having step 1, step 2 and step 3, and the production route B is a production route having step 1, step 4 and step 5.

The production route C of the present invention includes the following steps.

Production Route C

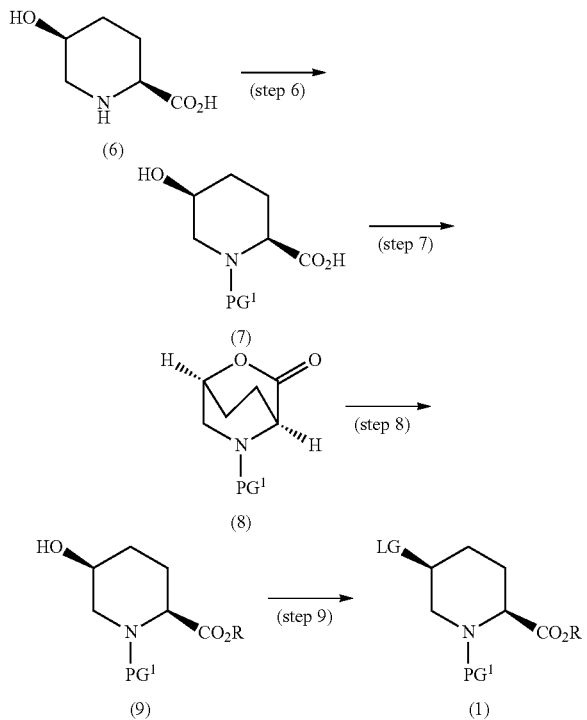

That is, the production route C is a production route for producing a compound represented by the formula (1) which is a starting material of step 1 from a compound represented by the above-mentioned formula (6).

The production routes A and B of the present invention each may further has production route C.

In the production routes A, B and C of the present invention, isomerization of the 2-position substituent of the pipecholic acid skeleton is unlikely to occur since a protecting group having low electron-withdrawing property is adopted as an amino-protecting group of the pipecolic acid skeleton. Therefore, they are superior in that a high purity intermediate can be obtained.

In addition, since step 1 common to the production routes A and B uses a compound represented by the formula (1) which is a stable compound as the starting material, the reaction can be carried out under mild conditions. Even when the compound represented by the formula (1) remains as an unreacted product, it can be easily removed. As described above, step 1 is a step suitable for industrial production and is a characteristic step of the present invention.

The production route C is suitable for industrial production because many of the compounds produced as intermediates have low polarity and ease of crystallizing, and operations such as extraction, recrystallization and the like can be efficiently performed.

[Production Methods of the Present Invention]

In the present specification, production methods 1-7 respectively mean the following production methods.

Production method 1: production method having step 1

Production method 2: production method having steps 2 and 3

Production method 3: production method having steps 4 and

Production method 4: production method having steps 6, 7, 8 and 9

Production method 5: production method having steps 8 and 9 and 3

Production method 6: production method having steps 1, 2

Production method 7: production method having steps 1, 4 and 5

The production method of the present invention is explained in detail below.

<Production Method 1>

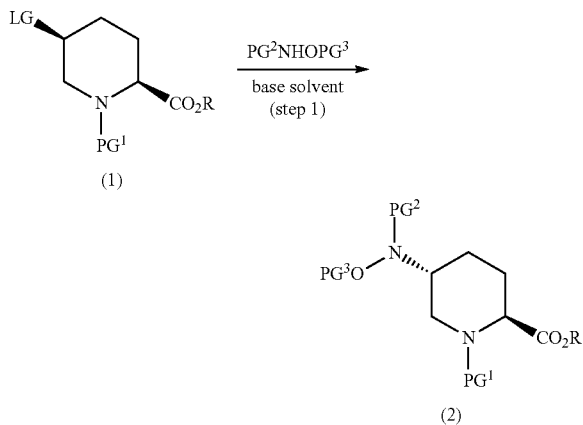

wherein each symbol is as defined above.

Production method 1 includes reacting a compound represented by the formula (1) with a hydroxylamine derivative represented by the formula $PG^2NHOPG^3$ in the presence of a base in a solvent to obtain a compound represented by the formula (2) (step 1).

[Step 1]
(Starting Material)

A compound represented by the formula (1) can be produced by any known method, and is preferably produced by the below-mentioned production method 4 or production method 5.

In the formula (1), the leaving group LG is not particularly limited as long as the reaction with the hydroxylamine derivative proceeds, and a sulfonyloxy group is preferable.

Examples of the sulfonyloxy group include alkylsulfonyloxy groups such as methanesulfonyloxy group and the like; halogenated alkylsulfonyloxy groups such as trichloromethanesulfonyloxy group, trifluoromethanesulfonyloxy group and the like; arylsulfonyloxy groups such as benzenesulfonyloxy group, p-toluenesulfonyloxy group and the like; and nitroarylsulfonyloxy groups such as p-nitrobenzenesulfonyloxy group, o-nitrobenzenesulfonyloxy group, o,p-dinitrobenzenesulfonyloxy group and the like.

Among these, arylsulfonyloxy group and nitroarylsulfonyloxy group are preferable. Furthermore, a nitroarylsulfonyloxy group is more preferable since it has high leaving ability and the elimination reaction proceeds under mild conditions; a p-nitrobenzenesulfonyloxy group and an o-nitrobenzenesulfonyloxy group are further preferable in view of the cost; and a p-nitrobenzenesulfonyloxy group is particularly preferable since production of by-products is less.

When the leaving ability of the leaving group LG is too low, the reaction may not proceed efficiently and a high temperature may be required. When it is too high, the reaction becomes unstable due to heat and basic conditions, and an eliminated product as a by-product may increase and the quality and yield may decrease.

As used herein, the "leaving ability" shows a high degree of reactivity, which is proportional to a high degree of stability of the conjugated acid of the leaving group LG after elimination. The high stability of the conjugated acid can be estimated from, for example, the value of the acid dissociation constant pKa, and a larger value of pKa means higher stability.

As for the value of the leaving ability of the leaving group LG (the value of pKa of the conjugated acid of the leaving group), the lower limit is generally not less than −13, preferably not less than −10, more preferably not less than −6, from the aspect of suppression of by-products, and the upper limit is generally not more than −1.5, preferably not more than −2, more preferably not more than −2.5, from the aspect of reactivity.

For example, the pKa of methanesulfonic acid is −2.6, and the pKa of sulfuric acid is −3. The pKa of trifluoromethanesulfonic acid is −14, which is not preferable as the leaving group LG.

In the formulas (1) and (2), as the amino-protecting group $PG^1$, isomerization is suppressed more when the electron-withdrawing property is lower. Therefore, from the aspect of quality and purity, an amino-protecting group with low electron-withdrawing property is preferable.

As used herein, the "electron-withdrawing property" means the effect of reducing the electron density at a specific position of a molecule. The value of the electron-withdrawing property is known to be in proportion to the value of $\sigma_p^-$ (hereinafter sometimes to be referred to as substituent constant) described in A survey of Hammett substituent constants and resonance and field parameters (Chem. Rev. 1991, 91, 165-195).

As the value of the electron-withdrawing property of $PG^1$, the upper limit of the value of the substituent constant is generally not more than 1.2. From the aspect of the suppression of the isomerization, it is preferably not more than 1.00, more preferably not more than 0.9, particularly preferably not more than 0.85, and the lower limit thereof is generally not less than −0.3, preferably not less than −0.2, more preferably not less than −0.1, particularly preferably not less than 0.

For example, a p-nitrobenzylsulfonyl group with a substituent constant value of 1.06, and a trifluoroacetyl group with a substituent constant value of 1.09 are not preferable as $PG^1$, because the electron-withdrawing property is high.

As an amino-protecting group $PG^1$ with low electron-withdrawing property, carbamate type protecting group and amide type protecting group with low electron-withdrawing property are preferable. Examples of the carbamate type protecting group include aliphatic oxycarbonyl groups such as methyloxycarbonyl group, ethyloxycarbonyl group, tert-butyloxycarbonyl group, allyloxycarbonyl group and the like; and aromatic oxycarbonyl groups such as benzyloxycarbonyl group, p-methyloxybenzylcarbonyl group, p-nitrobenzyloxycarbonyl group, 9-fluorenylmethyloxycarbonyl group and the like, and examples of the amide type protecting group with low electron-withdrawing property include hydrocarbon type acyl groups such as acetyl group, pivaloyl group, benzoyl group and the like.

Among these, from the aspect of the easiness of deprotection, a tert-butyloxycarbonyl group and an acetyl group are more preferable as $PG^1$.

The substituent constant value is 0.64 for the tert-butoxycarbonyl group, and 0.84 for the acetyl group.

In the formula (2) and the above-mentioned hydroxylamine derivative, an amino-protecting group with high electron-withdrawing property is preferable as the amino-protecting group $PG^2$ from the aspect of the reactivity of the hydroxylamine derivative.

As the value of the electron-withdrawing property of $PG^2$, $\sigma_p^-$ of greater than 1 is preferable.

As the amino-protecting group $PG^2$ with high electron-withdrawing property, sulfonamide type protecting group can be mentioned. From the aspect of the easiness of deprotection, nitrobenzenesulfonyl type protecting groups such as o-nitrobenzenesulfonyl group, p-nitrobenzenesulfonyl group, o,p-dinitrobenzenesulfonyl group, and the like are preferable.

In the formula (2) and the above-mentioned hydroxylamine derivative, an ether type protecting group is preferable as the hydroxyl-protecting group $PG^3$ from the aspect of enhancing the reactivity of the hydroxylamine derivative. From the aspect of the easiness of deprotection, an aromatic ether type protecting group is more preferable, and a benzyl group and a p-methoxybenzyl group are particularly preferable.

The hydroxylamine derivative is not particularly limited as long as the reaction proceeds, and from the aspects of reactivity and the availability and cost of the starting materials, N-(p-nitrobenzenesulfonyl)-O-benzyl-hydroxylamine is preferable. Among the hydroxylamine derivatives, a compound in which the amino group is free is unstable to heat, easily decomposed, and may decrease in purity. Therefore, a hydroxylamine derivative in which the amino group is protected is preferably used.

As the hydroxylamine derivative, a commercially available one may be used, or may be prepared and used by any known method. When a hydroxylamine derivative is prepared and used, one prepared in advance may be added to the reaction system, or it may be prepared in the reaction system and used as it is.

As the amount of the hydroxylamine derivative to be used, the lower limit is generally not less than 0.1 molar equivalent, preferably not less than 1 molar equivalent, more preferably not less than 1.02 molar equivalents, with respect to a compound represented by the formula (1), from the aspect of productivity, and the upper limit thereof is generally not more than 10 molar equivalents, preferably not more than 3 molar equivalents, more preferably not more than 2 molar equivalents, from the aspects of operability, quality and cost.

Step 1 is preferably performed in the presence of a base in a solvent.

The base is not particularly limited as long as the reaction proceeds. Examples thereof include tertiary amines, pyridines, organic strong base, metal amide, alkyl metal compound, metal hydride, metal alkoxide, carbonate, phosphate, metal hydroxide, cyanide and the like. As the base used in step 1, one kind may be used alone, or two or more kinds may be used in any combination and ratio.

Examples of the tertiary amines include triethylamine, diisopropylethylamine, N-methylmorpholine, quinuclidine, 1,4-diazabicyclo[2.2.2]octane and the like.

Examples of the pyridines include pyridine, 4-dimethylaminopyridine, 2-methylpyridine, 3-methylpyridine, 4-methylpyridine, 2,6-dimethylpyridine and the like.

Examples of the organic strong base include 1,8-diazabicyclo[5.4.0]undec-7-ene, tetramethylguanidine and the like.

Examples of the metal amide include lithium amide, sodium ethylamide, calcium diethylamide, lithium diisopropylamide, potassium benzylamide, sodium bis(trimethylsilyl)amide, lithium indolide, sodium pyrrolide, lithium pyrrolide, potassium pyrrolide, potassium pyrrolizide, aluminum diethylpyrrolide, ethylaluminum dipyrrolide, aluminum tripyrrolide, lithium diisopropylamide, sodium hexamethyldisilazide and the like.

Examples of the alkyl metal compound include n-butyllithium, sec-butyllithium, tert-butyllithium, isopropylmagnesium bromide and the like.

Examples of the metal hydride include lithium hydride, sodium hydride, potassium hydride, magnesium hydride, calcium hydride, cesium hydride and the like.

Examples of the metal alkoxide include lithium methoxide, lithium ethoxide, lithium propoxide, lithium tert-butoxide, sodium methoxide, sodium ethoxide, sodium propoxide, sodium tert-butoxide, potassium methoxide, potassium ethoxide, potassium propoxide, potassium tert-butoxide and the like.

Examples of the carbonate include sodium carbonate, potassium carbonate, cesium carbonate, sodium hydrogen carbonate, potassium hydrogen carbonate, cesium hydrogen carbonate and the like.

Examples of the phosphate include sodium phosphate, sodium hydrogen phosphate, sodium dihydrogen phosphate, potassium phosphate, potassium hydrogen phosphate, potassium dihydrogen phosphate and the like.

Examples of the metal hydroxide include lithium hydroxide, sodium hydroxide, potassium hydroxide, calcium hydroxide and the like.

Examples of the cyanide include sodium cyanide, potassium cyanide and the like.

When the basicity of the base to be used is too weak, the hydroxylamine derivative may not be activated and the reaction may not proceed. When the basicity is too strong, isomerization at the 2-position and by-products may increase and the purity may decrease. Furthermore, when the basicity is strong, the ester part of the substrate may be hydrolyzed and the purity may decrease.

Therefore, the base is preferably pyridine, carbonate, metal hydride or metal alkoxide, more preferably carbonate, further preferably sodium carbonate, potassium carbonate or cesium carbonate.

As the amount of the base to be used with respect to a compound represented by the formula (1), the lower limit is generally not less than 0.1 molar equivalent, and from the aspect of productivity, it is preferably not less than 1 molar equivalent, more preferably not less than 1.02 molar equivalents, and the upper limit is generally not more than 10 molar equivalents, preferably not more than 3 molar equivalents, more preferably not more than 2 molar equivalents, from the aspects of operability, quality and cost.

The solvent is not particularly limited as long as the reaction proceeds, and organic solvent or aqueous solvent can be used. From the aspect of reactivity, an organic solvent is preferably used.

As the organic solvent, at least one kind of solvent selected from the group consisting of alcohol solvent, ester solvent, ether solvent, ketone solvent, nitrile solvent, amide solvent, sulfoxide solvent, hydrocarbon solvent, and basic organic solvent can be used.

Examples of the alcohol solvent include alcohol represented by the formula ROH (R is as defined above). Preferably, alcohol having an aliphatic hydrocarbon group having 1-8 carbon atoms or an aromatic hydrocarbon group having 6-8 carbon atoms can be used. More preferably, methanol, ethanol, propanol, butanol, pentanol, hexanol, heptanol, octanol, benzyl alcohol, phenylethyl alcohol or isomer alcohol of these and the like can be used.

As the ester solvent, acetic acid esters such as ethyl acetate, propyl acetate, butyl acetate and the like can be used.

As the ether solvent, chain ethers such as diethyl ether, di-n-butyl ether, diisopropyl ether, di-n-butyl ether, tert-butyl methyl ether and the like; and cyclic ethers such as cyclopentyl methyl ether, tetrahydrofuran, 2-methyltetrahydrofuran, dioxane and the like can be used.

As the ketone solvent, aliphatic ketones such as acetone, methyl ethyl ketone, methyl isobutyl ketone and the like can be used.

As the nitrile solvent, aliphatic nitriles such as acetonitrile, propanonitrile, butyronitrile, isobutyronitrile, valeronitrile, isovaleronitrile and the like; aromatic nitriles such as benzonitrile and the like can be used.

As the amide solvent, aprotic amides such as N,N-dimethylformamide, N,N-dimethylacetamide, N-methylpyrrolidinone and the like can be used.

As the sulfoxide solvent, aprotic sulfoxides such as dimethyl sulfoxide and the like can be used.

As the hydrocarbon solvent, aliphatic hydrocarbons such as hexane, cyclohexane, heptane, cycloheptane and the like; aromatic hydrocarbons such as toluene, xylene and the like can be used.

As the basic organic solvent, pyridine solvents such as pyridine, 2-methylpyridine, 3-methylpyridine, 4-methylpyridine, 2,6-dimethylpyridine and the like can be used.

The solvent is preferably amide, ether solvent or hydrocarbon, more preferably amide, from the aspect of reactivity, and further preferably N,N-dimethylformamide or N,N-dimethylacetamide from the aspects of cost and availability of the starting materials.

As the solvent, the above-mentioned organic solvent may be used alone, or two or more kinds thereof mixed at any ratio may be used.

The lower limit of the amount of the solvent to be used is generally not less than 1 L and, from the aspect of operability, preferably not less than 2 L, further preferably not less than 3 L, per 1 kg of the compound represented by the formula (1), and the upper limit thereof is generally not more than 30 L, preferably not more than 20 L, more preferably not more than 10 L, per 1 kg of the compound represented by the formula (1), from the aspects of operability, productivity, cost and the like.

(Reaction Conditions)

The reaction temperature may vary depending on the base and solvent to be used. The lower limit is generally not less than 0° C., preferably not less than 10° C., more preferably not less than 15° C., further preferably not less than 20° C., particularly preferably not less than 25° C., from the aspect of productivity, and the upper limit is generally not more than 100° C., preferably not more than 70° C., more preferably not more than 65° C., further preferably not more than 60° C., particularly preferably not more than 55° C., from the aspects of quality, cost and the like.

When the reaction temperature is too low, the progress of the reaction may be delayed and the productivity may decrease, and when it is too high, the eliminated product and the 2-position isomer may increase and the quality of the obtained compound may decrease.

The reaction time may vary depending on the base and solvent to be used. From the aspect of productivity, it is generally 1 hr-120 hr, preferably 12 hr-72 hr.

The reaction is generally performed under normal pressure.

When a compound represented by the formula (1) and a hydroxylamine derivative are reacted in the presence of a base, the order of supply of these compounds can be appropriately selected. These compounds may be supplied all at once to the reaction system or supplied in plural divided portions. For example, in a reactor, one or more kinds of components from a compound represented by the formula (1), a hydroxylamine derivative, and a base are supplied together with a solvent, and using this as a base solution, the reaction can be performed by supplying the remaining components as a supply solution under reaction conditions. As the order of supply of these, a supply method in which a compound represented by the formula (1) and a hydroxylamine derivative are supplied together with a solvent into a reactor and, using this as a base solution, the reaction is performed by supplying a base under reaction conditions is preferable because the reaction can proceed while controlling the temperature and pH of the reaction solution. When an excessive amount of base is present in the reaction system, an overreacted product may be formed. The base may be present in the reaction system from the start, or may be supplied in the middle. Also, it may be supplied all at once or supplied in plural divided portions.

(Post-Treatment)

While the reaction mixture may be subjected as it is to the next step, it is generally provided as an organic layer after being subjected to treatments such as neutralization, partitioning, filtration and the like. Further, a product isolated from the organic layer by an isolation means such as concentration, crystallization and the like may be provided, or the product may be subjected after further purification by purification means such as recrystallization, column chromatography and the like.

In the reaction of step 1, a compound represented by the formula (2) can be stably obtained without going through an unstable intermediate. In particular, a compound represented by the following formula (2a) is particularly preferable because isomerization of the 2-position is suppressed by a protecting group having low electron-withdrawing property and deprotection of an amino group is easy. The compound is a novel compound.

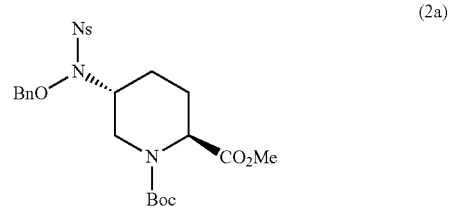

wherein Boc is a tert-butyloxycarbonyl group, Ns is a p-nitrobenzenesulfonyl group, Bn is a benzyl group, and Me is a methyl group.

A compound represented by the formula (2) may form a solvate such as hydrate or organic solvate or the like, the form thereof may vary depending on the starting material, solvent, and the like to be used, and the form thereof is not particularly limited as long as it does not inhibit the target reaction.

In the present invention, unless particularly indicated, "a compound represented by the formula (2)" means both a compound represented by the formula (2) and a solvate thereof.

<Production Method 2>

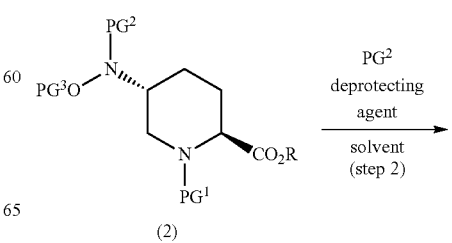

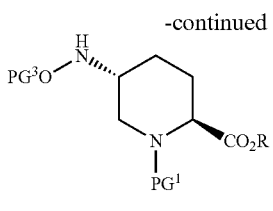

-continued

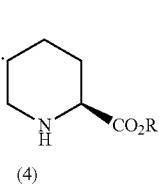

wherein each symbol is as defined above.

The production method 2 is characterized in that it has reacting a compound represented by the formula (2) and a $PG^2$ deprotecting agent to obtain a compound represented by the formula (3) or a salt thereof (step 2); and reacting a compound represented by the formula (3) or a salt thereof and a $PG^1$ deprotecting agent to obtain a compound represented by the formula (4) or a salt thereof (step 3).

[Step 2]

Step 2 is reacting a compound represented by the formula (2) and a $PG^2$ deprotecting agent to obtain a compound represented by the formula (3) or a salt thereof.

(Starting Material)

The $PG^2$ deprotecting agent is not particularly limited as long as it can remove an amino-protecting group $PG^2$, and a known deprotecting agent such as acid, base, oxidizing agent, reducing agent, metal catalyst, secondary amine, thiol compound, fluoride salt and the like can be used.

When $PG^2$ is a nitrobenzenesulfonyl type protecting group, the amino group is preferably deprotected using a thiol compound.

The thiol compound is not particularly limited as long as it can deprotect an amino group protected by a nitrobenzenesulfonamide type protecting group, and alkylthiol, arylthiol, mercaptocarboxylic acid and the like can be mentioned.

Examples of the alkylthiol include ethanethiol, 1-propanethiol, 2-propanethiol, 1-butanethiol, 2-butanethiol, 1-pentanethiol, octanethiol, decanethiol, dodecanethiol, pentadecanethiol and the like.

Examples of the arylthiol include thiophenol, methylbenzenethiol, dimethylbenzenethiol, ethylbenzenethiol, diethylbenzenethiol, naphthalenethiol and the like.

Examples of the mercaptocarboxylic acid include thioglycolic acid, 2-mercaptopropionic acid, 3-mercaptopropionic acid, 3-mercaptobutanoic acid, 2-mercaptoisobutyric acid, 3-mercaptoisobutyric acid, 3-mercapto-3-methylbutyric acid, 2-mercaptovaleric acid, 3-mercaptoisovaleric acid, 4-mercaptovaleric acid, 3-phenyl-3mercaptopropionic acid and the like can be mentioned.

The thiol compound is preferably mercaptocarboxylic acid, more preferably thioglycolic acid, from the aspects of availability of the starting materials and cost.

The amount of the $PG^2$ deprotecting agent to be used is not particularly limited as long as $PG^2$ can be removed. The lower limit is generally not less than 0.1 molar equivalent, preferably not less than 1 molar equivalent, more preferably not less than 1.02 molar equivalents, with respect to a compound represented by the formula (2), from the aspect of productivity. The upper limit thereof is generally not more than 20 molar equivalents, preferably not more than 15 molar equivalents, more preferably not more than 10 molar equivalents, from the aspects of operability, purity of reaction product and cost.

Step 2 is preferably performed in the presence of a base in a solvent.

The base is not particularly limited as long as the reaction proceeds. Examples thereof include tertiary amines, pyridines, organic strong base, metal amide, alkyl metal compound, metal hydride, metal alkoxide, carbonate, phosphate, metal hydroxide, cyanide and the like. As the base used in step 2, one kind may be used alone, or two or more kinds may be used in any combination and ratio.

Examples of the tertiary amines include triethylamine, diisopropylethylamine, N-methylmorpholine, quinuclidine, 1,4-diazabicyclo[2.2.2]octane and the like.

Examples of the pyridines include pyridine, 4-dimethylaminopyridine, 2-methylpyridine, 3-methylpyridine, 4-methylpyridine, 2,6-dimethylpyridine and the like.

Examples of the organic strong base include 1,8-diazabicyclo[5.4.0]undec-7-ene, tetramethylguanidine and the like.

Examples of the metal amide include lithium amide, sodium ethylamide, calcium diethylamide, lithium diisopropylamide, potassium benzylamide, sodium bis(trimethylsilyl)amide, lithium indolide, sodium pyrrolide, lithium pyrrolide, potassium pyrrolide, potassium pyrrolizide, aluminum diethylpyrrolide, ethylaluminum dipyrrolide, aluminum tripyrrolide, lithium diisopropylamide, sodium hexamethyldisilazide and the like.

Examples of the alkyl metal compound include n-butyllithium, sec-butyllithium, tert-butyllithium, isopropylmagnesium bromide and the like.

Examples of the metal hydride include lithium hydride, sodium hydride, potassium hydride, magnesium hydride, calcium hydride, cesium hydride and the like.

Examples of the metal alkoxide include lithium methyloxide, lithium ethyloxide, lithium propyloxide, lithium tert-butyloxide, sodium methyloxide, sodium ethyloxide, sodium propyloxide, sodium tert-butyloxide, potassium methyloxide, potassium ethyloxide, potassium propyloxide, potassium tert-butyloxide and the like.

Examples of the carbonate include sodium carbonate, potassium carbonate, cesium carbonate, sodium hydrogen carbonate, potassium hydrogen carbonate, cesium hydrogen carbonate and the like.

Examples of the phosphate include sodium phosphate, sodium hydrogen phosphate, sodium dihydrogen phosphate, potassium phosphate, potassium hydrogen phosphate, potassium dihydrogen phosphate and the like.

Examples of the metal hydroxide include lithium hydroxide, sodium hydroxide, potassium hydroxide, calcium hydroxide and the like.

Examples of the cyanide include sodium cyanide, potassium cyanide and the like.

Among these bases, from the aspect of the strength of the basicity, tertiary amine, pyridine, carbonate, metal hydride, metal alkoxide or metal hydroxide is preferable, carbonate is more preferable, and potassium carbonate or cesium carbonate is further preferable.

When the basicity of the base is too weak, the thiol compound may not be sufficiently activated and the progress of the reaction may be delayed, and when it is too strong, deesterification of the carboxylic acid ester at the 2-position may occur, and the purity and yield of the reaction product may decrease.

As the amount of the base to be used with respect to a compound represented by the formula (2), the lower limit is generally not less than 0.1 molar equivalent, preferably not less than 1 molar equivalent, more preferably not less than 1.02 molar equivalents, from the aspect of productivity, and the upper limit is generally not more than 20 molar equivalents, preferably not more than 15 molar equivalents, more preferably not more than 10 molar equivalents, from the aspects of operability, purity of the reaction product and cost.

The solvent is not particularly limited as long as the reaction proceeds, and organic solvent or aqueous solvent can be used. From the aspect of reactivity, an organic solvent is preferably used.

As the organic solvent, at least one kind of solvent selected from the group consisting of alcohol solvent, ester solvent, ether solvent, ketone solvent, nitrile solvent, amide solvent, sulfoxide solvent, hydrocarbon solvent, and basic organic solvent can be used.

Examples of the alcohol solvent include alcohol represented by the formula ROH (R is as defined above). Preferably, alcohol having an aliphatic hydrocarbon group having 1-8 carbon atoms or an aromatic hydrocarbon group having 6-8 carbon atoms can be used and, for example, methanol, ethanol, propanol, butanol, pentanol, hexanol, heptanol, octanol, benzyl alcohol, phenylethyl alcohol or these isomer alcohol and the like can be used.

As the ester solvent, acetic acid esters such as ethyl acetate, propyl acetate, butyl acetate and the like can be used.

As the ether solvent, chain ethers such as diethyl ether, di-n-butyl ether, diisopropyl ether, di-n-butyl ether, tert-butyl methyl ether and the like; and cyclic ethers such as cyclopentyl methyl ether, tetrahydrofuran, 2-methyltetrahydrofuran, dioxane and the like can be used.

As the ketone solvent, aliphatic ketones such as acetone, methyl ethyl ketone, methyl isobutyl ketone and the like can be used.

As the nitrile solvent, aliphatic nitriles such as acetonitrile, propanonitrile, butyronitrile, isobutyronitrile, valeronitrile, isovaleronitrile and the like; aromatic nitriles such as benzonitrile and the like can be used.

As the amide solvent, aprotic amides such as N,N-dimethylformamide, N,N-dimethylacetamide, N-methylpyrrolidinone and the like can be used.

As the sulfoxide solvent, aprotic sulfoxides such as dimethyl sulfoxide and the like can be used.

As the hydrocarbon solvent, for example, aliphatic hydrocarbons such as hexane, cyclohexane, heptane, cycloheptane and the like; aromatic hydrocarbons such as toluene, xylene and the like can be used.

As the basic organic solvent, pyridine solvents such as pyridine, 2-methylpyridine, 3-methylpyridine, 4-methylpyridine, 2,6-dimethylpyridine and the like can be used.

The solvent is preferably an alcohol represented by the formula ROH (R is as defined above) from the aspect of the purity of the reaction product. More preferably, it is an alcohol having the same carbon number as R of the compound represented by the formula (2), and having an aliphatic hydrocarbon group having 1-8 carbon atoms or an aromatic hydrocarbon group having 6-8 carbon atoms, since the impurity due to transesterification can be suppressed, further preferably an alcohol having aliphatic hydrocarbon group having 1-3 carbon atoms such as methanol, ethanol, 1-propanol, 2-propanol and the like or benzyl alcohol from the aspects of cost and availability of the starting materials.

As the solvent, the above-mentioned organic solvent may be used alone, or two or more kinds thereof mixed at any ratio may be used.

The lower limit of the amount of the solvent to be used is generally not less than 1 L, preferably not less than 2 L, more preferably not less than 3 L, per 1 kg of the compound represented by the formula (2), from the aspect of operability, and the upper limit thereof is generally not more than 30 L, preferably not more than 20 L, more preferably not more than 15 L, per 1 kg of the compound represented by the formula (2), from the aspects of operability, productivity, cost and the like.

(Reaction Conditions)

The reaction temperature may vary depending on the $PG^2$ deprotecting agent, base, solvent and the like to be used. The lower limit is generally not less than 0° C., preferably not less than 5° C., more preferably not less than 10° C., from the aspect of productivity, and the upper limit is generally not more than ° C., preferably not more than 50° C., more preferably not more than 40° C., from the aspects of the purity of the reaction product and cost.

The reaction time may vary depending on the $PG^2$ deprotecting agent, base, solvent and the like to be used. From the aspect of productivity, it is generally 0.5 hr-48 hr, preferably 1-24 hr.

The reaction is generally performed under normal pressure.

When a compound represented by the formula (2) and a $PG^2$ deprotecting agent are reacted, the order of supply of these compounds can be appropriately selected. These compounds may be supplied all at once to the reaction system or supplied in plural divided portions. For example, in a reactor, one or more kinds of any of a compound represented by the formula (2) and a $PG^2$ deprotecting agent are supplied together with a solvent, and using this as a base solution, the reaction can be performed by supplying the remaining components as a supply solution under reaction conditions. The base may be present in the reaction system from the start, or may be supplied in the middle, or it may be supplied all at once or supplied in plural divided portions.

(Post-Treatment)

The reaction mixture may be subjected as it is to the next step, or subjected to the next step after treatments such as neutralization, partitioning, filtration and the like, or subjected to the next step after isolation of the reaction product by isolation means such as concentration, crystallization and the like. The resultant product may be subjected to the next step after further purification by known purification means such as recrystallization, column chromatography and the like.

The form of the compound represented by the formula (3) is generally a free amine form, but the form is not particularly limited as long as the reaction proceeds, and a salt or a solvate such as hydrate or organic solvate may be used. As the form of the compound represented by the formula (3), a desired form can be appropriately selected depending on the starting material, solvent and the like to be used.

In the present invention, unless particularly indicated, the "compound represented by the formula (3)" means both a compound represented by the formula (3) and a solvate thereof, and the "salt of a compound represented by the formula (3)" means both a salt of a compound represented by the formula (3) and a solvate of the salt thereof.

When a compound represented by the formula (3) is obtained as a free amine form, it may be converted to a salt thereof or a solvate thereof such as hydrate, organic solvate and the like when desired according to a conventional method. When a compound represented by the formula (3) is obtained as a salt or a solvate such as hydrate, organic solvate and the like, it may be converted to a free amine form when desired according to a conventional method.

Examples of the salt of a compound represented by the formula (3) include inorganic acid salt and organic acid salt.

Examples of the inorganic acid salt include hydrochloride, hydrobromide, hydroiodide, sulfate, phosphate, nitrate, polyphosphate and the like.

Examples of the organic acid salt include carboxylates such as acetate, trifluoroacetate, lactate, tartrate, oxalate, fumarate, maleate, benzoate, citrate, glucuronate, gluconate and the like; and sulfonates such as methanesulfonate, ethanesulfonate, benzenesulfonate, p-toluenesulfonate, isethionate, trifluoromethanesulfonate and the like.

The salt of a compound represented by the formula (3) is preferably an inorganic acid salt, more preferably hydrochloride since this compound has ease of crystallizing and industrial handling.

[Step 3]

In step 3, a compound represented by the formula (3) or a salt thereof is reacted with a $PG^1$ deprotecting agent to obtain a compound represented by the formula (4) or a salt thereof.

When a salt of a compound represented by the formula (4) is obtained, for example, removal of an amino-protecting group $PG^1$ and salt formation of a compound represented by the formula (3) may be performed simultaneously, or a salt may be formed after removal of $PG^1$.

When removal of $PG^1$ and salt formation are performed simultaneously, for example, a salt of a compound represented by the formula (4) is obtained by reacting a compound represented by the formula (3) with a $PG^1$ deprotecting agent to remove $PG^1$. When a salt is formed after removal of $PG^1$, for example, a salt of a compound represented by the formula (4) is obtained by reacting a compound represented by the formula (3) with a $PG^1$ deprotecting agent to obtain a free amine form of the compound represented by the formula (4), and reacting same with an acid that forms a salt.

(Starting Material)

The $PG^1$ deprotecting agent is not particularly limited as long as it can remove $PG^1$, and a known deprotecting agent such as acid, base, oxidizing agent, reducing agent, metal catalyst, secondary amine, thiol compound, fluoride salt and the like can be used.

For example, when $PG^1$ is a tert-butyloxycarbonyl group or an acetyl group, $PG^1$ can be removed using an acid as the PG' deprotecting agent.

As the acid, at least one kind of acid selected from the group consisting of inorganic acids and organic acids can be used.

As the inorganic acid, hydrochloric acid, hydrobromic acid, hydroiodic acid, sulfuric acid, nitric acid, phosphoric acid, polyphosphoric acid and the like can be used.

As the organic acid, carboxylic acid such as acetic acid, trifluoroacetic acid, lactic acid, tartaric acid, oxalic acid, fumaric acid, maleic acid, benzoic acid, citric acid, glucuronic acid, gluconic acid and the like; or sulfonic acid such as methanesulfonic acid, ethanesulfonic acid, benzenesulfonic acid, p-toluenesulfonic acid, isethionic acid, trifluoromethanesulfonic acid and the like can be used.

As the acid, trifluoroacetic acid, p-toluenesulfonic acid or hydrochloric acid is preferable, and hydrochloric acid is more preferable, from the aspects of the availability of the starting materials and cost.

The amount of the $PG^1$ deprotecting agent to be used is not particularly limited as long as it can remove $PG^1$. The lower limit is generally not less than 0.1 molar equivalent, preferably not less than 1 molar equivalent, more preferably not less than 1.02 molar equivalents, with respect to a compound represented by the formula (3) or a salt thereof, from the aspect of productivity, and the upper limit is generally not more than 20 molar equivalents, preferably not more than 15 molar equivalents, more preferably not more than 10 molar equivalents, with respect to a compound represented by the formula (3) or a salt thereof, from the aspects of operability, purity of the reaction product, and cost.

Step 3 is preferably performed in a solvent.

The solvent is not particularly limited as long as the reaction proceeds, and an organic solvent or an aqueous solvent can be used. From the aspect of reactivity, an organic solvent is preferably used. The organic solvent is preferably an alcohol represented by the formula ROH (R is as defined above) from the aspect of the purity of the reaction product. More preferably, it is an alcohol having the same carbon number as R of the compound represented by the formula (2), and having an aliphatic hydrocarbon group having 1-8 carbon atoms or an aromatic hydrocarbon group having 6-8 carbon atoms, since the impurity due to transesterification can be suppressed, further preferably an alcohol having aliphatic hydrocarbon group having 1-3 carbon atoms such as methanol, ethanol, 1-propanol, 2-propanol and the like or benzyl alcohol from the aspects of cost and availability of the starting materials.

The lower limit of the amount of the solvent to be used is generally not less than 1 L, preferably not less than 2 L, more preferably not less than 3 L, per 1 kg of the compound represented by the formula (3) or a salt thereof, from the aspect of operability, and the upper limit thereof is generally not more than 30 L, preferably not more than 20 L, more preferably not more than 15 L, per 1 kg of the compound represented by the formula (3) or a salt thereof, from the aspects of operability, productivity, cost and the like.

(Reaction Conditions)

The reaction temperature may vary depending on the PG' deprotecting agent, solvent and the like to be used. The lower limit is generally not less than 20° C., preferably not less than ° C., more preferably not less than 30° C., from the aspect of productivity, and the upper limit is generally not more than 80° C., preferably not more than 70° C., more preferably not more than 60° C., from the aspects of the purity of the reaction product and cost.

The reaction time may vary depending on the PG' deprotecting agent, solvent and the like to be used. From the aspect of productivity, it is generally 0.5 hr-24 hr, preferably 1-12 hr.

The reaction is generally performed under normal pressure.

When a compound represented by the formula (3) or a salt thereof and a $PG^1$ deprotecting agent are reacted, the order of supply of these compounds can be appropriately selected. These compounds may be supplied all at once to the reaction system or supplied in plural divided portions. For example, in a reactor, one or more kinds of any of a compound represented by the formula (3) and a $PG^1$ deprotecting agent are supplied together with a solvent, and using this as a base solution, the reaction can be performed by supplying the remaining components as a supply solution under reaction conditions. When an acid is used as the $PG^1$ deprotecting agent, the acid may be present in the reaction system from the start, or may be supplied in the middle, or it may be supplied all at once or supplied in plural divided portions.

When the PG¹ protecting group of the compound represented by the formula (3) is a tert-butyloxycarbonyl group, isobutene and carbon dioxide are generated as by-product gases during deprotection. To perform the reaction while controlling the amount of these gases generated, it is preferable to supply an acid and a solvent together into a reactor, and using this as a base solution, perform reaction by supplying a compound represented by the formula (3) and a solvent as a supply solution under reaction conditions.
(Post-Treatment)

The reaction mixture may be subjected as it is to the next step, or subjected to the next step after treatments such as neutralization, partitioning, filtration and the like, or subjected to the next step after isolation of the reaction product by isolation means such as concentration, crystallization and the like. The resultant product may be subjected to the next step after further purification by known purification means such as recrystallization, column chromatography and the like.

The form of the compound represented by the formula (4) is not particularly limited as long as the reaction proceeds, and may be a free amine form, or a salt or a solvate such as hydrate or organic solvate may be formed. As the form of the compound represented by the formula (4), a desired form can be appropriately selected depending on the starting material, solvent and the like to be used.

When a compound represented by the formula (4) is obtained as a free amine form, it may be converted to a salt thereof or a solvate thereof such as hydrate, organic solvate and the like when desired according to a conventional method. When a compound represented by the formula (4) is obtained as a salt or a solvate such as hydrate, organic solvate and the like, it may be converted to a free amine form when desired according to a conventional method.

In the present invention, unless particularly indicated, the "compound represented by the formula (4)" means both a compound represented by the formula (4) and a solvate thereof, and the "salt of a compound represented by the formula (4)" means both a salt of a compound represented by the formula (4) and a solvate of the salt thereof.

In the present invention, the form of the compound represented by the formula (4) is preferably a salt.

Examples of the salt of a compound represented by the formula (4) include inorganic acid salt and organic acid salt.

Examples of the inorganic acid salt include hydrochloride, hydrobromide, hydroiodide, sulfate, phosphate, nitrate, polyphosphate and the like.

Examples of the organic acid salt include carboxylates such as acetate, trifluoroacetate, lactate, tartrate, oxalate, fumarate, maleate, benzoate, citrate, glucuronate, gluconate and the like; and sulfonates such as methanesulfonate, ethanesulfonate, benzenesulfonate, p-toluenesulfonate, isethionate, trifluoromethanesulfonate and the like.

The salt of a compound represented by the formula (4) is preferably an inorganic acid salt, more preferably hydrochloride since this compound has ease of crystallizing and industrial handling.

When a compound represented by the formula (4) is converted to a salt, an acid that forms a salt may be used.

The acid is not particularly limited as long as it forms a salt, and at least one kind of acid selected from the group consisting of inorganic acids and organic acids can be used.

As the inorganic acid, hydrochloric acid, hydrobromic acid, hydroiodic acid, sulfuric acid, phosphoric acid, nitric acid, polyphosphoric acid and the like can be used.

As the organic acid, carboxylic acid such as acetic acid, trifluoroacetic acid, lactic acid, tartaric acid, oxalic acid, fumaric acid, maleic acid, benzoic acid, citric acid, glucuronic acid, gluconic acid and the like; or sulfonic acid such as methanesulfonic acid, ethanesulfonic acid, benzenesulfonic acid, p-toluenesulfonic acid, isethionic acid, trifluoromethanesulfonic acid and the like can be used.

As the acid, hydrochloric acid, sulfuric acid, trifluoroacetic acid or p-toluenesulfonic acid is preferable, and hydrochloric acid is more preferable, from the aspects of the availability of the starting materials and cost.

As the amount of the acid to be used, the lower limit is generally not less than 0.1 molar equivalent, preferably not less than 1 molar equivalent, more preferably not less than 1.02 molar equivalents, with respect to a compound represented by the formula (4), from the aspect of productivity, and the upper limit thereof is generally not more than 20 molar equivalents, preferably not more than 15 molar equivalents, more preferably not more than 10 molar equivalents, from the aspects of operability, purity of the reaction product and cost.

When a compound represented by the formula (4) and an acid are reacted, the order of supply of these compounds can be appropriately selected. These compounds may be supplied all at once to the reaction system or supplied in plural divided portions. For example, in a reactor, one or more kinds of a compound represented by the formula (4) and an acid are supplied together with a solvent, and using this as a base solution, the reaction can be performed by supplying the remaining components as a supply solution under reaction conditions.

In step 3, it is more preferable to simultaneously perform removal of an amino-protecting group PG² and salt formation of a compound represented by the formula (5).

<Production Method 3>

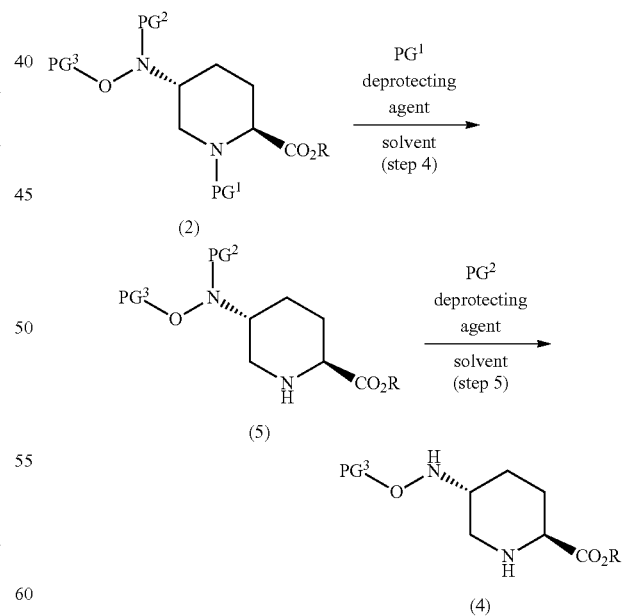

wherein each symbol is as defined above.

The production method 3 is characterized in that it has reacting a compound represented by the formula (2) and a PG² deprotecting agent to obtain a compound represented by the formula (5) or a salt thereof (step 4); and reacting a compound represented by the formula (5) or a salt thereof and a PG² deprotecting agent to obtain a compound represented by the formula (4) or a salt thereof (step 5).

[Step 4]

Step 4 is reacting a compound represented by the formula (2) and a PG¹ deprotecting agent to obtain a compound represented by the formula (5) or a salt thereof.

(Starting Material)

As the PG¹ deprotecting agent, the same PG¹ deprotecting agent as in the aforementioned step 3 can be used.

The amount of the PG¹ deprotecting agent to be used is not particularly limited as long as PG¹ can be removed. The lower limit is generally not less than 0.1 molar equivalent, preferably not less than 1 molar equivalent, more preferably not less than 3 molar equivalents, based on a compound represented by the formula (2), from the aspect of productivity. The upper limit thereof is generally not more than 20 molar equivalents, preferably not more than 15 molar equivalents, more preferably not more than 10 molar equivalents, from the aspects of operability, productivity and cost.

Step 4 can be performed in a solvent.

The solvent is not particularly limited as long as the reaction proceeds, and an organic solvent can be used. The organic solvent is preferably an alcohol represented by the formula ROH (R is as defined above) from the aspect of the purity of the reaction product. More preferably, it is an alcohol having the same carbon number as R of the compound represented by the formula (2), and having an aliphatic hydrocarbon group having 1-8 carbon atoms or an aromatic hydrocarbon group having 6-8 carbon atoms, since the impurity due to transesterification can be suppressed, further preferably an alcohol having aliphatic hydrocarbon group having 1-3 carbon atoms such as methanol, ethanol, 1-propanol, 2-propanol and the like or benzyl alcohol from the aspects of cost and availability of the starting materials.

As the solvent, the above-mentioned organic solvent may be used alone, or two or more kinds thereof mixed at any ratio may be used.

The lower limit of the amount of the solvent to be used is generally not less than 1 L and, from the aspect of operability, it is preferably not less than 2 L, more preferably not less than 3 L, per 1 kg of the compound represented by the formula (2), and the upper limit thereof is generally not more than 30 L, preferably not more than 20 L, more preferably not more than 15 L, per 1 kg of the compound represented by the formula (2), from the aspects of operability, productivity and cost.

(Reaction Conditions)

The reaction temperature may vary depending on the PG¹ deprotecting agent, solvent and the like to be used. The lower limit is generally not less than 20° C., preferably not less than ° C., more preferably not less than 30° C., from the aspect of productivity, and the upper limit is generally not more than ° C., preferably not more than 70° C., more preferably not more than 60° C., from the aspects of the purity of the reaction product and cost.

The reaction time may vary depending on the PG¹ deprotecting agent, solvent and the like to be used. From the aspect of productivity, it is generally 0.5 hr-24 hr, preferably 1-12 hr.

The reaction is generally performed under normal pressure.

When a compound represented by the formula (2) and a PG¹ deprotecting agent are reacted, the order of supply of these compounds can be appropriately selected. These compounds may be supplied all at once to the reaction system or supplied in plural divided portions. For example, in a reactor, one or more kinds of any of a compound represented by the formula (2) and a PG¹ deprotecting agent are supplied together with a solvent, and using this as a base solution, the reaction can be performed by supplying the remaining components as a supply solution under reaction conditions. When an acid is used as the PG¹ deprotecting agent, the acid may be present in the reaction system from the start, or may be supplied in the middle, or it may be supplied all at once or supplied in plural divided portions.

When the PG¹ protecting group of the compound represented by the formula (2) is a tert-butyloxycarbonyl group, isobutene and carbon dioxide are generated as by-product gases during deprotection. To perform the reaction while controlling the amount of these gases generated, it is preferable to supply an acid and a solvent together into a reactor, and using this as a base solution, perform reaction by supplying a compound represented by the formula (2) and a solvent as a supply solution under reaction conditions.

(Post-Treatment)

The reaction mixture may be subjected as it is to the next step, or subjected to the next step after treatments such as neutralization, partitioning, filtration and the like, or subjected to the next step after isolation of the reaction product by isolation means such as concentration, crystallization and the like. The resultant product may be subjected to the next step after further purification by known purification means such as recrystallization, column chromatography and the like.

Among the compounds represented by the formula (5), the compound represented by the following formula (5a) is a novel compound. Since this compound has ease of crystallizing, it can be easily separated from reaction by-products without complicated purification such as chromatography and the like, and is suitable for industrial production.

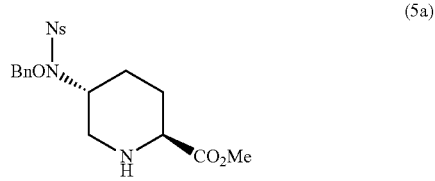

(5a)

wherein Ns is a p-nitrobenzenesulfonyl group, Bn is a benzyl group, and Me is a methyl group.

The form of the compound represented by the formula (5) is generally a free amine form, but the form is not particularly limited as long as the reaction proceeds, and a salt may be used. As the form of the compound represented by the formula (5), a desired form can be appropriately selected depending on the starting material, solvent and the like to be used.

When a compound represented by the formula (5) is obtained as a free amine form, it may be converted to a salt thereof or a solvate thereof such as hydrate, organic solvate and the like when desired according to a conventional method. When a compound represented by the formula (5) is obtained as a salt or a solvate such as hydrate, organic solvate and the like, it may be converted to a free amine form when desired according to a conventional method.

In the present invention, unless particularly indicated, the "compound represented by the formula (5)" means both a compound represented by the formula (5) and a solvate thereof, and the "salt of the compound represented by the formula (5)" means both a salt of the compound represented by the formula (5) and the solvate of a salt thereof.

Examples of the salt of a compound represented by the formula (5) include inorganic acid salt and organic acid salt.

Examples of the inorganic acid salt include hydrochloride, hydrobromide, hydroiodide, sulfate, phosphate, nitrate, polyphosphate and the like.

Examples of the organic acid salt include carboxylates such as acetate, trifluoroacetate, lactate, tartrate, oxalate, fumarate, maleate, benzoate, citrate, glucuronate, gluconate and the like; and sulfonates such as methanesulfonate, ethanesulfonate, benzenesulfonate, p-toluenesulfonate, isethionate, trifluoromethanesulfonate and the like.

The salt of a compound represented by the formula (5) is preferably an inorganic acid salt, more preferably hydrochloride since this compound has ease of crystallizing and industrial handling.

[Step 5]

In step 5, a compound represented by the formula (5) or a salt thereof is reacted with a $PG^2$ deprotecting agent to obtain a compound represented by the formula (4) or a salt thereof.

When a salt of a compound represented by the formula (4) is obtained, for example, removal of an amino-protecting group $PG^2$ and salt formation of a compound represented by the formula (5) may be performed simultaneously, or a salt may be formed after removal of $PG^2$.

When removal of $PG^2$ and salt formation are performed simultaneously, for example, a salt of a compound represented by the formula (4) is obtained by reacting a compound represented by the formula (5) with a $PG^2$ deprotecting agent to remove $PG^2$. When a salt is formed after removal of $PG^2$, for example, a salt of a compound represented by the formula (4) is obtained by reacting a compound represented by the formula (5) with a $PG^2$ deprotecting agent to obtain a free amine form of the compound represented by the formula (4), and reacting same with an acid that forms a salt.

(Starting Material)

As the $PG^2$ deprotecting agent, the same $PG^2$ deprotecting agent as in the aforementioned step 2 can be used.

As the amount of the $PG^2$ deprotecting agent to be used, the lower limit is generally not less than 1 molar equivalent and, from the aspect of productivity, it is preferably not less than 1.5 molar equivalent, more preferably not less than 2 molar equivalents, with respect to a compound represented by the formula (5) or a salt thereof, and the upper limit is generally not more than 20 molar equivalents and, from the aspect of cost, it is preferably not more than 15 molar equivalents, more preferably not more than 10 molar equivalents.

Step 5 is preferably performed in the presence of a base in a solvent.

The base is not particularly limited as long as the reaction proceeds. Examples thereof include tertiary amines, pyridines, organic strong base, metal amide, alkyl metal compound, metal hydride, metal alkoxide, carbonate, phosphate, metal hydroxide, cyanide and the like. As the base used in step 5, one kind may be used alone, or two or more kinds may be used in any combination and ratio.

Examples of the tertiary amines include triethylamine, diisopropylethylamine, N-methylmorpholine, quinuclidine, 1,4-diazabicyclo[2.2.2]octane and the like.

Examples of the pyridines include pyridine, 4-dimethylaminopyridine, 2-methylpyridine, 3-methylpyridine, 4-methylpyridine, 2,6-lutidine and the like.

Examples of the organic strong base include 1,8-diazabicyclo[5.4.0]undec-7-ene, tetramethylguanidine and the like.

Examples of the metal amide include lithium amide, sodium ethylamide, calcium diethylamide, lithium diisopropylamide, potassium benzylamide, sodium bis(trimethylsilyl)amide, lithium indolide, sodium pyrrolide, lithium pyrrolide, potassium pyrrolide, potassium pyrrolizide, aluminum diethylpyrrolide, ethylaluminum dipyrrolide, aluminum tripyrrolide, lithium diisopropylamide, sodium hexamethyldisilazide and the like.

Examples of the alkyl metal compound include n-butyllithium, sec-butyllithium, tert-butyllithium, isopropylmagnesium bromide and the like.

Examples of the metal hydride include lithium hydride, sodium hydride, potassium hydride, magnesium hydride, calcium hydride, cesium hydride and the like.

Examples of the metal alkoxide include lithium methyloxide, lithium ethyloxide, lithium propyloxide, lithium tert-butyloxide, sodium methyloxide, sodium ethyloxide, sodium propyloxide, sodium tert-butyloxide, potassium methyloxide, potassium ethyloxide, potassium propyloxide, potassium tert-butyloxide and the like.

Examples of the carbonate include sodium carbonate, potassium carbonate, cesium carbonate, sodium hydrogen carbonate, potassium hydrogen carbonate, cesium hydrogen carbonate and the like.

Examples of the phosphate include sodium phosphate, sodium hydrogen phosphate, sodium dihydrogen phosphate, potassium phosphate, potassium hydrogen phosphate, potassium dihydrogen phosphate and the like.

Examples of the metal hydroxide include lithium hydroxide, sodium hydroxide, potassium hydroxide, calcium hydroxide and the like.

Examples of the cyanide include sodium cyanide, potassium cyanide and the like.

Among these bases, from the aspect of the strength of the basicity, tertiary amine, pyridine, carbonate, metal hydride, metal hydride, metal alkoxide or hydroxide is preferable, carbonate is more preferable, and potassium carbonate or cesium carbonate is further preferable.

When the basicity of the base is too weak, the thiol compound may not be sufficiently activated and the progress of the reaction may be delayed, and when it is too strong, deesterification of the carboxylic acid ester at the 2-position may occur, and the purity and yield of the reaction product may decrease.

As the amount of the base to be used with respect to a compound represented by the formula (5) or a salt thereof, the lower limit is generally not less than 0.1 molar equivalent, preferably not less than 1 molar equivalent, more preferably not less than 1.02 molar equivalents, from the aspect of productivity, and the upper limit is generally not more than 20 molar equivalents, preferably not more than 15 molar equivalents, more preferably not more than 10 molar equivalents, from the aspects of operability, purity of the reaction product and cost.

The solvent is not particularly limited as long as the reaction proceeds, and organic solvent or aqueous solvent can be used. From the aspect of reactivity, an organic solvent is preferably used.

As the organic solvent, at least one kind of solvent selected from the group consisting of alcohol solvent, ester solvent, ether solvent, ketone solvent, nitrile solvent, amide solvent, sulfoxide solvent, hydrocarbon solvent, and basic organic solvent can be used.

Examples of the alcohol solvent include alcohol represented by the formula ROH (R is as defined above).

Preferably, alcohol having an aliphatic hydrocarbon group having 1-8 carbon atoms or an aromatic hydrocarbon group having 6-8 carbon atoms can be used and, for example, methanol, ethanol, propanol, butanol, pentanol, hexanol, heptanol, octanol, benzyl alcohol, phenylethyl alcohol or these isomer alcohol and the like can be used.

As the ester solvent, acetic acid esters such as ethyl acetate, propyl acetate, butyl acetate and the like can be used.

As the ether solvent, chain ethers such as diethyl ether, di-n-butyl ether, diisopropyl ether, di-n-butyl ether, tert-butyl methyl ether and the like; and cyclic ethers such as cyclopentyl methyl ether, tetrahydrofuran, 2-methyltetrahydrofuran, dioxane and the like can be used.

As the ketone solvent, aliphatic ketones such as acetone, methyl ethyl ketone, methyl isobutyl ketone and the like can be used.

As the nitrile solvent, aliphatic nitriles such as acetonitrile, propanonitrile, butyronitrile, isobutyronitrile, valeronitrile, isovaleronitrile and the like; aromatic nitriles such as benzonitrile and the like can be used.

As the amide solvent, aprotic amides such as N,N-dimethylformamide, N,N-dimethylacetamide, N-methylpyrrolidinone and the like can be used.

As the sulfoxide solvent, aprotic sulfoxides such as dimethyl sulfoxide and the like can be used.

As the hydrocarbon solvent, for example, aliphatic hydrocarbons such as hexane, cyclohexane, heptane, cycloheptane and the like; aromatic hydrocarbons such as toluene, xylene and the like can be used.

As the basic organic solvent, pyridine solvents such as pyridine, 2-methylpyridine, 3-methylpyridine, 4-methylpyridine, 2,6-dimethylpyridine and the like can be used.

The solvent is preferably an alcohol represented by the formula ROH (R is as defined above) from the aspect of the purity of the reaction product. More preferably, it is an alcohol having the same carbon number as R of the compound represented by the formula (2), and having an aliphatic hydrocarbon group having 1-8 carbon atoms or an aromatic hydrocarbon group having 6-8 carbon atoms, since the impurity due to transesterification can be suppressed, further preferably an alcohol having aliphatic hydrocarbon group having 1-3 carbon atoms such as methanol, ethanol, 1-propanol, 2-propanol and the like or benzyl alcohol from the aspects of cost and availability of the starting materials.

As the solvent, the above-mentioned organic solvent may be used alone, or two or more kinds thereof mixed at any ratio may be used.

The lower limit of the amount of the solvent to be used is generally not less than 1 L, preferably not less than 2 L, further preferably not less than 3 L, per 1 kg of the compound represented by the formula (5) or a salt thereof, from the aspect of operability, and the upper limit thereof is generally not more than 30 L, preferably not more than 20 L, further preferably not more than 15 L, per 1 kg of the compound represented by the formula (5), from the aspects of operability, productivity and cost.

(Reaction Conditions)

The reaction temperature may vary depending on the $PG^2$ deprotecting agent, base, solvent and the like to be used. The lower limit is generally not less than 0° C., preferably not less than 5° C., more preferably not less than 10° C., from the aspect of productivity, and the upper limit is generally not more than ° C., preferably not more than 50° C., more preferably not more than 45° C., from the aspects of the purity of the reaction product and cost.

The reaction time may vary depending on the $PG^2$ deprotecting agent, base, solvent and the like to be used. From the aspect of productivity, it is generally 0.5 hr-48 hr, preferably 1-24 hr.

The reaction is generally performed under normal pressure.

When a compound represented by the formula (5) or a salt thereof and a $PG^2$ deprotecting agent are reacted, the order of supply of these compounds can be appropriately selected. These compounds may be supplied all at once to the reaction system or supplied in plural divided portions. For example, in a reactor, one or more kinds of any of a compound represented by the formula (5) and a $PG^2$ deprotecting agent are supplied together with a solvent, and using this as a base solution, the reaction can be performed by supplying the remaining components as a supply solution under reaction conditions. The base may be present in the reaction system from the start, or may be supplied in the middle, or it may be supplied all at once or supplied in plural divided portions.

(Post-Treatment)

The reaction mixture may be subjected as it is to the next step, or subjected to the next step after treatments such as neutralization, partitioning, filtration and the like, or subjected to the next step after isolation of the reaction product by isolation means such as concentration, crystallization and the like. The resultant product may be subjected to the next step after further purification by known purification means such as recrystallization, column chromatography and the like.

The form of the compound represented by the formula (4) is not particularly limited as long as the reaction proceeds, and may be a free amine form, or a salt or a solvate such as hydrate or organic solvate may be formed. As the form of the compound represented by the formula (4), a desired form can be appropriately selected depending on the starting material, solvent and the like to be used.

When a compound represented by the formula (4) is obtained as a free amine form, it may be converted to a salt thereof or a solvate thereof such as hydrate, organic solvate and the like when desired according to a conventional method. When a compound represented by the formula (4) is obtained as a salt or a solvate such as hydrate, organic solvate and the like, it may be converted to a free amine form when desired according to a conventional method.

In the present invention, unless particularly indicated, the "compound represented by the formula (4)" means both a compound represented by the formula (4) and a solvate thereof, and the "salt of a compound represented by the formula (4)" means both a salt of a compound represented by the formula (4) and a solvate of the salt thereof.

The form of the compound represented by the formula (4) is preferably a salt, similar to the above-mentioned step 3.

Examples of the salt of a compound represented by the formula (4) include inorganic acid salt and organic acid salt.

Examples of the inorganic acid salt include hydrochloride, hydrobromide, hydroiodide, sulfate, phosphate, nitrate, polyphosphate and the like.

Examples of the organic acid salt include carboxylates such as acetate, trifluoroacetate, lactate, tartrate, oxalate, fumarate, maleate, benzoate, citrate, glucuronate, gluconate and the like; and sulfonates such as methanesulfonate, ethanesulfonate, benzenesulfonate, p-toluenesulfonate, isethionate, trifluoromethanesulfonate and the like.

The salt of a compound represented by the formula (4) is preferably an inorganic acid salt, more preferably hydrochloride since this compound has ease of crystallizing and industrial handling.

When a compound represented by the formula (4) is converted to a salt, the method described in the above-mentioned step 3 can be used. When a compound represented by the formula (4) is converted to a salt, an acid that forms a salt may be used.

The acid is not particularly limited as long as it forms a salt, and at least one kind of acid selected from the group consisting of inorganic acids and organic acids can be used.

As the inorganic acid, hydrochloric acid, hydrobromic acid, hydroiodic acid, sulfuric acid, nitric acid, phosphoric acid, polyphosphoric acid and the like can be used.

As the organic acid, carboxylic acid such as acetic acid, trifluoroacetic acid, lactic acid, tartaric acid, oxalic acid, fumaric acid, maleic acid, benzoic acid, citric acid, glucuronic acid, gluconic acid and the like; or sulfonic acid such as methanesulfonic acid, ethanesulfonic acid, benzenesulfonic acid, p-toluenesulfonic acid, isethionic acid, trifluoromethanesulfonic acid and the like can be used.

As the acid, trifluoroacetic acid, p-toluenesulfonic acid, hydrochloric acid or sulfuric acid is preferable, and hydrochloric acid is more preferable, from the aspects of the availability of the starting materials and cost.

As the amount of the acid to be used, the lower limit is generally not less than 0.1 molar equivalent, preferably not less than 1 molar equivalent, more preferably not less than 1.02 molar equivalents, with respect to a compound represented by the formula (4), from the aspect of productivity, and the upper limit thereof is generally not more than 20 molar equivalents, preferably not more than 15 molar equivalents, more preferably not more than 10 molar equivalents, from the aspects of operability, purity of the reaction product and cost.

When a compound represented by the formula (4) and an acid are reacted, the order of supply of these compounds can be appropriately selected. These compounds may be supplied all at once to the reaction system or supplied in plural divided portions. For example, in a reactor, one or more kinds of a compound represented by the formula (4) and an acid are supplied together with a solvent, and using this as a base solution, the reaction can be performed by supplying the remaining components as a supply solution under reaction conditions.

(Post-Treatment)

The reaction mixture may be subjected as it is to the next step, or subjected to the next step after treatments such as neutralization, partitioning, filtration and the like, or subjected to the next step after isolation of the reaction product by isolation means such as concentration, crystallization and the like. The resultant product may be subjected to the next step after further purification by known purification means such as recrystallization, column chromatography and the like.

<Production Method 4>

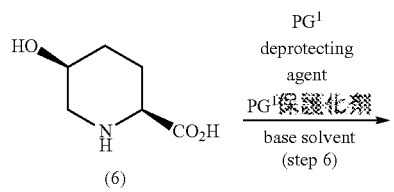

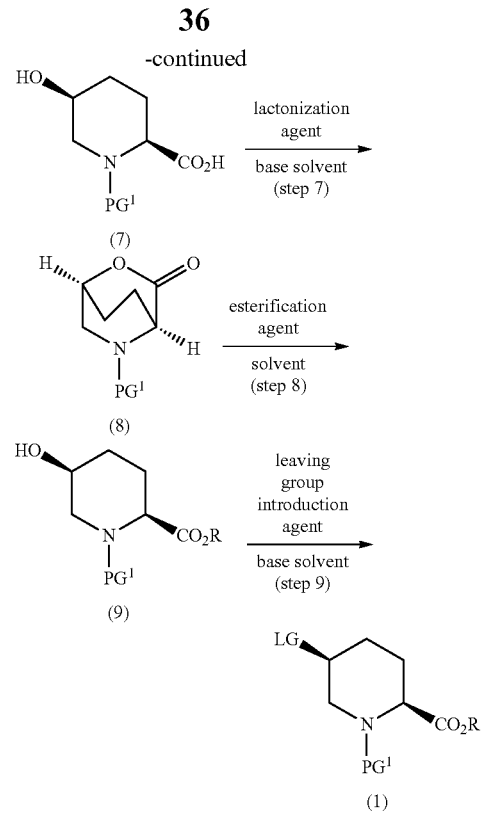

wherein each symbol is as defined above.

Production method 4 is the same as the above-mentioned production route C, and is a production route for producing a compound represented by the formula (1) from a compound represented by the formula (6).

Production method 4 is characterized in that it contains obtaining a compound represented by the formula (7) by reacting a compound represented by the formula (6) with a $PG^1$ protecting agent (step 6);

obtaining a compound represented by the formula (8) by reacting the above-mentioned compound represented by the formula (7) with a lactonization agent (step 7);

obtaining a compound represented by the formula (9) by reacting the above-mentioned compound represented by the formula (8) with an esterification agent (step 8); and obtaining a compound represented by the formula (1) by reacting the above-mentioned compound represented by the formula (9) with a leaving group introduction agent (step 9).

The production method 4 is suitable for industrial production because many of the compounds produced as intermediates have low polarity and ease of crystallizing, and operations such as extraction, recrystallization and the like can be efficiently performed.

[Step 6]

Step 6 is obtaining a compound represented by the formula (7) by reacting a compound represented by the formula (6) with a $PG^1$ protecting agent.

(Starting Material)

The compound represented by the formula (6) (cis-5-hydroxypipecolic acid) can be produced by a known method, for example, the methods described in WO 2014/098188, WO 2014/129459, WO 2015/098774 and the like.

The form of the compound represented by the formula (6) is not particularly limited as long as the reaction proceeds, and a free form is preferable.

In the present invention, unless particularly indicated, the "compound represented by the formula (6)" means both a compound represented by the formula (6) and a solvate thereof, and the "salt of a compound represented by the formula (6)" means both a salt of a compound represented by the formula (6) and a solvate of the salt thereof.

The amino-protecting group $PG^1$ in the formula (7) is particularly preferably a carbamate type protecting group, an amide type protecting group with low electron-withdrawing property, or a sulfonamide type protecting group with low electron-withdrawing property. As the $PG^1$ protecting agent, therefore, carbamate protecting agents such as tert-butyloxycarbonylating agent and the like, and amide protecting agents such as acetylating agent and the like, which are corresponding $PG^1$ protecting agents, are preferable. These are not particularly limited as long as the reaction proceeds and known ones can be used.

Examples of the tert-butyloxycarbonylating agent include di-tert-butyl dicarbonate, N-tert-butylcarbonylimidazole, tert-butylphenylcarbonate, tert-butylcarbazate, N-tert-butyloxycarbonylimidazole and the like; from the aspects of cost and availability of the starting materials, it is preferably di-tert-butyldicarbonate.

Examples of the acetylating agent include acetic anhydride, acetyl chloride, acetyl bromide and the like and, from the aspects of cost and availability of the starting materials, acetic anhydride is preferable.

Among these protecting agents, tert-butyloxycarbonylating agents and acetylating agents are more preferable since a protecting group with low electron-withdrawing property can be introduced.

The amount of the $PG^1$ protecting agent to be used is not particularly limited as long as the reaction proceeds, and the lower limit is generally not less than 0.1 molar equivalent, preferably not less than 1 molar equivalent, more preferably not less than 1.02 molar equivalents, with respect to a compound represented by the formula (6), from the aspect of productivity, and the upper limit thereof is generally not more than 10 molar equivalents, preferably not more than 3 molar equivalents, more preferably not more than 2 molar equivalents, from the aspects of operability, purity of the reaction product and cost.

Step 6 is preferably performed in the presence of a base in a solvent.

The base is not particularly limited as long as the reaction proceeds. Examples thereof include tertiary amines, pyridines, organic strong base, metal amide, alkyl metal compound, metal hydride, metal alkoxide, carbonate, phosphate, metal hydroxide, cyanide and the like. As the base used in step 6, one kind may be used alone, or two or more kinds may be used in any combination and ratio.

Examples of the tertiary amines include triethylamine, diisopropylethylamine, N-methylmorpholine, quinuclidine, 1,4-diazabicyclo[2.2.2]octane and the like.

Examples of the pyridines include pyridine, 4-dimethylaminopyridine, 2-methylpyridine, 3-methylpyridine, 4-methylpyridine, 2,6-lutidine and the like.

Examples of the organic strong base include 1,8-diazabicyclo[5.4.0]undec-7-ene, tetramethylguanidine and the like.

Examples of the metal amide include lithium amide, sodium ethylamide, calcium diethylamide, lithium diisopropylamide, potassium benzylamide, sodium bis(trimethylsilyl)amide, lithium indolide, sodium pyrrolide, lithium pyrrolide, potassium pyrrolide, potassium pyrrolizide, aluminum diethylpyrrolide, ethylaluminum dipyrrolide, aluminum tripyrrolide, lithium diisopropylamide, sodium hexamethyldisilazide and the like.

Examples of the alkyl metal compound include n-butyllithium, sec-butyllithium, tert-butyllithium, isopropylmagnesium bromide and the like.

Examples of the metal hydride include lithium hydride, sodium hydride, potassium hydride, magnesium hydride, calcium hydride, cesium hydride and the like.

Examples of the metal alkoxide include lithium methyloxide, lithium ethyloxide, lithium propyloxide, lithium tert-butyloxide, sodium methyloxide, sodium ethyloxide, sodium propyloxide, sodium tert-butyloxide, potassium methyloxide, potassium ethyloxide, potassium propyloxide, potassium tert-butyloxide and the like.

Examples of the carbonate include sodium carbonate, potassium carbonate, cesium carbonate, sodium hydrogen carbonate, potassium hydrogen carbonate, cesium hydrogen carbonate and the like.

Examples of the phosphate include sodium phosphate, sodium hydrogen phosphate, sodium dihydrogen phosphate, potassium phosphate, potassium hydrogen phosphate, potassium dihydrogen phosphate and the like.

Examples of the metal hydroxide include lithium hydroxide, sodium hydroxide, potassium hydroxide, calcium hydroxide and the like.

Examples of the cyanide include sodium cyanide, potassium cyanide and the like.

Among these bases, from the aspect of the strength of the basicity, tertiary amine, pyridine or carbonate is preferable, triethylamine, pyridine or potassium carbonate is more preferable, and from the aspect of reactivity, trimethylamine is further preferable. When the basicity of the base to be used is too strong, an overreacted product may be produced.

As the amount of the base to be used with respect to a compound represented by the formula (6), the lower limit is generally not less than 0.1 molar equivalent, preferably not less than 1 molar equivalent, more preferably not less than 1.02 molar equivalents, from the aspect of productivity, and the upper limit is generally not more than 15 molar equivalents, preferably not more than 10 molar equivalents, more preferably not more than 5 molar equivalents, from the aspects of operability, purity of the reaction product and cost.

As the base used in step 6, one kind may be used alone, or two or more kinds may be used in any combination and ratio.

The solvent is not particularly limited as long as the reaction proceeds, and aqueous solvents such as water and the like or an organic solvent can be used. From the aspects of operability and cost, water or a mixed solvent of water and organic solvent is preferable, and water is more preferable.

As the organic solvent, at least one kind of solvent selected from the group consisting of alcohol solvent, ester solvent, ether solvent, ketone solvent, nitrile solvent, amide solvent, sulfoxide solvent, hydrocarbon solvent, and basic organic solvent can be used.

Examples of the alcohol solvent include alcohol represented by the formula ROH (R is as defined above). Preferably, alcohol having an aliphatic hydrocarbon group having 1-8 carbon atoms or an aromatic hydrocarbon group having 6-8 carbon atoms can be used and, for example, methanol, ethanol, propanol, butanol, pentanol, hexanol, heptanol, octanol, benzyl alcohol, phenylethyl alcohol or these isomer alcohol and the like can be used.

As the ester solvent, acetic acid esters such as ethyl acetate, propyl acetate, butyl acetate and the like can be used.

As the ether solvent, chain ethers such as diethyl ether, di-n-butyl ether, diisopropyl ether, di-n-butyl ether, tert-butyl methyl ether, cyclopentyl methyl ether and the like; and cyclic ethers such as tetrahydrofuran, 2-methyltetrahydrofuran, dioxane and the like can be used.

As the ketone solvent, aliphatic ketones such as acetone, methyl ethyl ketone, methyl isobutyl ketone and the like can be used.

As the nitrile solvent, aliphatic nitriles such as acetonitrile, propanonitrile, butyronitrile, isobutyronitrile, valeronitrile, isovaleronitrile and the like; aromatic nitriles such as benzonitrile and the like can be used.

As the amide solvent, aprotic amides such as N,N-dimethylformamide, N,N-dimethylacetamide, N-methylpyrrolidinone and the like can be used.

As the sulfoxide solvent, aprotic sulfoxides such as dimethyl sulfoxide and the like can be used.

As the hydrocarbon solvent, aliphatic hydrocarbons such as hexane, cyclohexane, heptane, cycloheptane and the like; aromatic hydrocarbons such as toluene, xylene and the like can be used.

As the basic organic solvent, pyridine solvents such as pyridine, 2-methylpyridine, 3-methylpyridine, 4-methylpyridine, 2,6-dimethylpyridine and the like can be used.

The above-mentioned organic solvent may be used alone, or two or more kinds thereof mixed at any ratio may be used.

The solvent is preferably water from the aspects of cost and operability.

The lower limit of the amount of the solvent to be used is generally not less than 1 L, preferably not less than 2 L, further preferably not less than 3 L, per 1 kg of the compound represented by the formula (6), from the aspect of operability, and the upper limit thereof is generally not more than 30 L, preferably not more than 20 L, more preferably not more than 10 L, per 1 kg of the compound represented by the formula (6), from the aspects of operability, productivity and cost.

When a mixed solvent of water and an organic solvent is used as the solvent in step 6, as the mixing ratio of the organic solvent, the lower limit is generally not less than by mass, preferably not less than 0.2-fold by mass, further preferably not less than 0.3-fold by mass, based on water, and the upper limit is generally not more than 20-fold by mass, preferably not more than 15-fold by mass, further preferably not more than 10-fold by mass, based on water.

The pH of the reaction mixture is generally 5-14, more preferably 7-12, further preferably 8-11, from the aspect of reactivity. When the pH of the reaction mixture is too low, the reaction may not proceed well and when it is too high, an overreacted product may increase and the purity and yield of the reaction product may decrease. The pH of the reaction mixture is the pH of the layer containing water when water is used as the solvent, and when an organic solvent is used, the pH of the aqueous layer when the same volume of water as the reaction mixture is added.

(Reaction Conditions)

The reaction temperature may vary depending on the PG' protecting agent, base, solvent and the like to be used. The lower limit is generally not less than 5° C., preferably not less than 10° C., more preferably not less than 15° C., from the aspect of productivity, and the upper limit is generally not more than ° C., preferably not more than 45° C., more preferably not more than 40° C., from the aspects of the purity of the reaction product and cost.

The reaction time may vary depending on the PG' protecting agent, base, solvent and the like to be used. From the aspect of productivity, it is generally 0.1 hr-24 hr, preferably 0.5 hr-12 hr.

The reaction is generally performed under normal pressure.

When a compound represented by the formula (6) and a PG' protecting agent are reacted, the order of supply of these compounds can be appropriately selected. These compounds may be supplied all at once to the reaction system or supplied in plural divided portions. For example, in a reactor, one or more kinds of any of a compound represented by the formula (6) and a PG$^1$ protecting agent are supplied together with a solvent, and using this as a base solution, the reaction can be performed by supplying the remaining components as a supply solution under reaction conditions. The base may be present in the reaction system from the start, or may be supplied in the middle, or it may be supplied all at once or supplied in plural divided portions.

(Post-Treatment)

The reaction mixture may be subjected as it is to the next step, or subjected to the next step after treatments such as neutralization, partitioning, filtration and the like, or subjected to the next step after isolation of the reaction product by isolation means such as concentration, crystallization and the like. The resultant product may be subjected to the next step after further purification by known purification means such as recrystallization, column chromatography and the like. Among these, from the aspect of productivity, the reaction mixture is preferably subjected as it is to the next step.

A compound represented by the formula (7) may form a salt or a solvate such as hydrate or organic solvate or the like, the form thereof may vary depending on the starting material, solvent, and the like to be used, and the form thereof is not particularly limited as long as it does not inhibit the target reaction.

In the present invention, unless particularly indicated, "a compound represented by the formula (7)" means both a compound represented by the formula (7) and a solvate thereof, and the "salt of a compound represented by the formula (7)" means both a salt of a compound represented by the formula (7) and a solvate of the salt thereof.

Among the compounds represented by the formula (7), since the compound represented by the following formula (7a) has ease of crystallizing, it can be easily separated from reaction by-products without complicated purification such as chromatography and the like, and is suitable for industrial production.

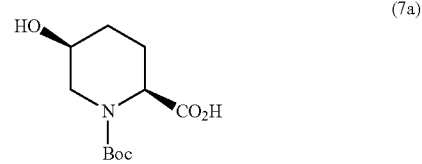 [SMILES: CC(C)(C)OC(=O)N1C[C@@H](O)CC[C@H]1C(=O)O]

(7a)

[Step 7]

Step 7 is obtaining a compound represented by the formula (8) by reacting a compound represented by the formula (7) obtained in step 6 with a lactonization agent.

(Starting Material)

As the lactonization agent, at least one kind of compound selected from the group consisting of acylating agent, alkoxycarbonylating agent and sulfonylating agent can be used.

As the acylating agent, acid anhydride acylating agents such as formic acid-acetic anhydride, acetic anhydride, trifluoroacetic anhydride and the like; and halogenated acyl such as acetyl chloride, chloroacetyl chloride, dichloroacetyl chloride, trichloroacetyl chloride, propionyl chloride, benzoyl chloride, 4-chlorobenzoyl chloride, acetyl bromide, propionyl bromide, benzoyl bromide and the like can be used.

As the alkoxycarbonylating agent, acid anhydride alkoxycarbonylating agents such as di-tert-butyl dicarbonate and the like; and halogenated alkoxycarbonylating agents such as benzyloxycarbonyl chloride, allyloxycarbonyl chloride, benzyloxycarbonyl bromide, allyloxycarbonyl bromide and the like can be used.

As the sulfonylating agent, halogenated sulfonylating agents such as methanesulfonyl chloride, p-toluenesulfonyl chloride, 2-nitrobenzenesulfonyl chloride, methanesulfonyl bromide, p-toluenesulfonyl bromide, 2-nitrobenzenesulfonyl bromide and the like can be used.

The lactonization agent is preferably an acylating agent, more preferably an acid anhydride acylating agent, further preferably acetic anhydride, from the aspect of reactivity.

As the amount of the lactonization agent to be used, the lower limit is generally not less than 0.1 molar equivalent, preferably not less than 1 molar equivalent, more preferably not less than 1.02 molar equivalents, with respect to a compound represented by the formula (7), from the aspect of productivity. The upper limit thereof is generally not more than 10 molar equivalents, preferably not more than 3 molar equivalents, more preferably not more than 2 molar equivalents, from the aspects of operability, purity of reaction product and cost.

Step 7 can be performed in the presence of a base in a solvent.

The base is not particularly limited as long as the reaction proceeds. Examples thereof include tertiary amines, pyridines, organic strong base, metal amide, alkyl metal compound, metal hydride, metal alkoxide, carbonate, phosphate, metal hydroxide, cyanide and the like. As the base used in step 7, one kind may be used alone, or two or more kinds may be used in any combination and ratio.

Examples of the tertiary amines include triethylamine, diisopropylethylamine, N-methylmorpholine, quinuclidine, 1,4-diazabicyclo[2.2.2]octane and the like.

Examples of the pyridines include pyridine, 4-dimethylaminopyridine, 2-methylpyridine, 3-methylpyridine, 4-methylpyridine, 2,6-lutidine and the like.

Examples of the organic strong base include 1,8-diazabicyclo[5.4.0]undec-7-ene, tetramethylguanidine and the like.

Examples of the metal amide include lithium diisopropylamide, sodium hexamethyldisilazide and the like.

Examples of the alkyl metal compound include n-butyllithium, sec-butyllithium, tert-butyllithium, isopropylmagnesium bromide and the like.

Examples of the metal hydride include lithium hydride, sodium hydride, potassium hydride, magnesium hydride, calcium hydride, cesium hydride and the like.

Examples of the metal alkoxide include lithium methyloxide, lithium ethyloxide, lithium propyloxide, lithium tert-butyloxide, sodium methyloxide, sodium ethyloxide, sodium propyloxide, sodium tert-butyloxide, potassium methyloxide, potassium ethyloxide, potassium propyloxide, potassium tert-butyloxide and the like.

Examples of the carbonate include sodium carbonate, potassium carbonate, cesium carbonate, sodium hydrogen carbonate, potassium hydrogen carbonate, cesium hydrogen carbonate and the like.

Examples of the phosphate include sodium phosphate, sodium hydrogen phosphate, sodium dihydrogen phosphate, potassium phosphate, potassium hydrogen phosphate, potassium dihydrogen phosphate and the like.

Examples of the metal hydroxide include lithium hydroxide, sodium hydroxide, potassium hydroxide, calcium hydroxide and the like.

Examples of the cyanide include sodium cyanide, potassium cyanide and the like.

Among these bases, from the aspect of the strength of the basicity, tertiary amine, pyridine and carbonate is preferable, triethylamine, pyridine and potassium carbonate are more preferable and, from the aspect of reactivity, triethylamine is further preferable.

As the amount of the base to be used with respect to a compound represented by the formula (7), the lower limit is generally not less than 0.1 molar equivalent, preferably not less than 1 molar equivalent, more preferably not less than 1.02 molar equivalents, from the aspect of productivity, and the upper limit is generally not more than 10 molar equivalents, preferably not more than 3 molar equivalents, more preferably not more than 2 molar equivalents, from the aspects of operability, purity of the reaction product and cost.

The solvent is not particularly limited as long as the reaction proceeds, and organic solvent or aqueous solvent can be used. From the aspect of reactivity, an organic solvent is preferably used.

As the organic solvent, at least one kind of solvent selected from the group consisting of alcohol solvent, ester solvent, ether solvent, ketone solvent, nitrile solvent, amide solvent, sulfoxide solvent, hydrocarbon solvent, and basic organic solvent can be used.

Examples of the alcohol solvent include alcohol represented by the formula ROH (R is as defined above). Preferably, alcohol having an aliphatic hydrocarbon group having 1-8 carbon atoms or an aromatic hydrocarbon group having 6-8 carbon atoms can be used and, for example, methanol, ethanol, propanol, butanol, pentanol, hexanol, heptanol, octanol, benzyl alcohol, phenylethyl alcohol or these isomer alcohol and the like can be used.

As the ester solvent, acetic acid esters such as ethyl acetate, propyl acetate, butyl acetate and the like can be used.

As the ether solvent, chain ethers such as diethyl ether, di-n-butyl ether, diisopropyl ether, di-n-butyl ether, tert-butyl methyl ether and the like; and cyclic ethers such as cyclopentyl methyl ether, tetrahydrofuran, 2-methyltetrahydrofuran, dioxane and the like can be used.

As the ketone solvent, aliphatic ketones such as acetone, methyl ethyl ketone, methyl isobutyl ketone and the like can be used.

As the nitrile solvent, aliphatic nitriles such as acetonitrile, propanonitrile, butyronitrile, isobutyronitrile, valeronitrile, isovaleronitrile and the like; aromatic nitriles such as benzonitrile and the like can be used.

As the amide solvent, aprotic amides such as N,N-dimethylformamide, N,N-dimethylacetamide, N-methylpyrrolidinone and the like can be used.

As the sulfoxide solvent, aprotic sulfoxides such as dimethyl sulfoxide and the like can be used.

As the hydrocarbon solvent, for example, aliphatic hydrocarbon solvents such as hexane, cyclohexane, heptane, cycloheptane and the like; aromatic hydrocarbon solvents such as toluene, xylene and the like can be used.

As the basic organic solvent, pyridine solvents such as pyridine, 2-methylpyridine, 3-methylpyridine, 4-methylpyridine, 2,6-dimethylpyridine and the like can be used.

The solvent is preferably ester solvent, more preferably ethyl acetate, from the aspect of cost and operability.

As the solvent, the above-mentioned organic solvent may be used alone, or two or more kinds thereof mixed at any ratio may be used.

The lower limit of the amount of the solvent to be used is generally not less than 1 L, preferably not less than 2 L, further preferably not less than 3 L, per 1 kg of the compound represented by the formula (7), from the aspect of operability, and the upper limit thereof is generally not more than 30 L, preferably not more than 20 L, more preferably not more than 10 L, per 1 kg of the compound represented by the formula (7), from the aspects of operability, productivity and cost.

(Reaction Time)

The reaction temperature may vary depending on the lactonization agent, base, solvent and the like to be used. The lower limit is generally not less than 0° C., preferably not less than 5° C., more preferably not less than 10° C., from the aspect of productivity, and the upper limit is generally not more than 50° C., preferably not more than 45° C., more preferably not more than 40° C., from the aspects of the purity of the reaction product and cost.

The reaction time may vary depending on the lactonization agent, base, solvent and the like to be used. From the aspect of productivity, it is generally 0.5 hr-48 hr, preferably 1-24 hr.

The reaction is generally performed under normal pressure.

When a compound represented by the formula (7) and a lactonization agent are reacted, the order of supply of these compounds can be appropriately selected. These compounds may be supplied all at once to the reaction system or supplied in plural divided portions. For example, in a reactor, one or more kinds of any of a compound represented by the formula (7) and a lactonization agent are supplied together with a solvent, and using this as a base solution, the reaction can be performed by supplying the remaining components as a supply solution under reaction conditions. The base may be present in the reaction system from the start, or may be supplied in the middle, or it may be supplied all at once or supplied in plural divided portions.

(Post-Treatment)

The reaction mixture may be subjected as it is to the next step, or subjected to the next step after treatments such as neutralization, partitioning, filtration and the like, or subjected to the next step after isolation of the reaction product by isolation means such as concentration, crystallization and the like. The resultant product may be subjected to the next step after further purification by known purification means such as recrystallization, column chromatography and the like. Among these, from the aspect of productivity, the reaction mixture is preferably subjected as it is to the next step.

The compound represented by the formula (8) may form a solvate such as hydrate or organic solvate. The form thereof may vary depending on the starting material, solvent, and the like to be used. The form thereof is not particularly limited as long as it does not inhibit the desired reaction.

In the present invention, unless particularly indicated, the "compound represented by the formula (8)" means both a compound represented by the formula (8) and a solvate thereof.

Among the compounds represented by the formula (8), since the compounds represented by the formula (8a) and the formula (8b) have ease of crystallizing, it can be easily separated from reaction by-products without complicated purification such as chromatography and the like, and is suitable for industrial production. A compound represented by the formula (8b) is a novel compound.

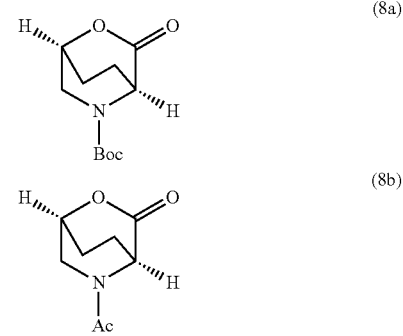

wherein Boc is a tert-butyloxycarbonyl group, and Ac is an acetyl group.

[Step 8]

Step 8 is obtaining a compound represented by the formula (9) by reacting a compound represented by the formula (8) obtained in step 7 with an esterification agent.

(Starting Material)

As the esterification agent, metal alkoxide represented by the formula ROM (R is as defined above) or alcohol represented by the formula ROH (R is as defined above) can be used.

Metal alkoxide is not particularly limited as long as the reaction proceeds. A metal alkoxide wherein R is a aliphatic hydrocarbon group having 1-3 carbon atoms, and M is alkali metal or alkaline earth metal is preferable. For example, lithium methyloxide, lithium ethyloxide, sodium methyloxide, sodium ethyloxide, potassium methyloxide, potassium ethyloxide, magnesium dimethyloxide, magnesium diethyloxide, calcium dimethyloxide, calcium diethyloxide, cesium dimethyloxide, cesium diethyloxide and the like can be used. More preferably, it is a metal alkoxide wherein R is an aliphatic hydrocarbon group having 1-2 carbon atoms and M is alkali metal, and sodium methyloxide or sodium ethyloxide from the aspects of cost and availability of the starting materials.

The alcohol is not particularly limited as long as it is alcohol represented by the formula ROH and the reaction proceeds. Preferably, alcohol having an aliphatic hydrocarbon group having 1-8 carbon atoms or an aromatic hydrocarbon group having 6-8 carbon atoms can be used and, for example, methanol, ethanol, propanol, butanol, pentanol, hexanol, heptanol, octanol, benzyl alcohol, phenylethyl alcohol or these isomer alcohol and the like can be used. It is more preferably an alcohol having a hydrocarbon group having 1-3 carbon atoms such as methanol, ethanol, 1-propanol, 2-propanol and the like or benzyl alcohol, and particularly preferably methanol or benzyl alcohol.

When esterification is performed using an alcohol compound, the reaction is preferably performed in the presence of an acid.

The acid is not particularly limited as long as the reaction proceeds, and inorganic acid or organic acid can be used.

Examples of the inorganic acid include hydrochloric acid, hydrobromic acid, hydroiodic acid, sulfuric acid, phosphoric acid, nitric acid, phosphoric acid, polyphosphoric acid and the like.

Examples of the organic acid include carboxylic acids such as acetic acid, trifluoroacetic acid, trichloroacetic acid, lactic acid, tartaric acid, oxalic acid, fumaric acid, maleic acid, benzoic acid, citric acid, glucuronic acid, gluconic acid and the like; and sulfonic acids such as methanesulfonic acid, ethanesulfonic acid, benzenesulfonic acid, p-toluenesulfonic acid, isethionic acid and the like.

The acid is preferably sulfuric acid or p-toluenesulfonic acid from the aspect of reactivity.

As the amount of the esterification agent to be used, the lower limit is generally not less than 0.1 molar equivalent, preferably not less than 1 molar equivalent, more preferably not less than 1.02 molar equivalents, with respect to a compound represented by the formula (8), from the aspect of productivity, and the upper limit thereof is generally not more than 20 molar equivalents, preferably not more than 10 molar equivalents, more preferably not more than 5 molar equivalents, from the aspects of operability, purity of the reaction product and cost.

Step 8 is preferably performed in a solvent.

The solvent is not particularly limited as long as the reaction proceeds, and an alcohol represented by the formula ROH (R is as defined above) is preferable, an alcohol having an aliphatic hydrocarbon group having 1-8 carbon atoms or aromatic hydrocarbon group having 6-8 carbon atoms is more preferable, and an alcohol having an aliphatic hydrocarbon group having 1-3 carbon atoms such as methanol, ethanol, propanol and the like is further preferable.

As the solvent, the above-mentioned organic solvent may be used alone, or two or more kinds thereof mixed at any ratio may be used.

The lower limit of the amount of the solvent to be used is generally not less than 1 L, preferably not less than 2 L, more preferably not less than 3 L, per 1 kg of the compound represented by the formula (8), from the aspect of operability, and the upper limit thereof is generally not more than 30 L, preferably not more than 25 L, more preferably not more than 20 L, per 1 kg of the compound represented by the formula (8), from the aspects of operability, productivity and cost.

(Reaction Conditions)

The reaction temperature may vary depending on the esterification agent, solvent and the like to be used. The lower limit is generally not less than 0° C., preferably not less than 1° C., more preferably not less than 2° C., from the aspect of productivity, and the upper limit is generally not more than ° C., preferably not more than 20° C., more preferably not more than 10° C., from the aspects of the purity of the reaction product and cost.

The reaction time may vary depending on the esterification agent, solvent and the like to be used. From the aspect of productivity, it is generally 0.1 hr-24 hr, preferably 0.5 hr-12 hr.

While the reaction is generally performed under normal pressure, pressurization may be applied.

When a compound represented by the formula (8) and an esterification agent are reacted, the order of supply of these compounds can be appropriately selected. These compounds may be supplied all at once to the reaction system or supplied in plural divided portions. For example, in a reactor, one or more kinds of any of a compound represented by the formula (8) and an esterification agent are supplied together with a solvent, and using this as a base solution, the reaction can be performed by supplying the remaining components as a supply solution under reaction conditions.

(Post-Treatment)

The reaction mixture may be subjected as it is to the next step, or subjected to the next step after treatments such as neutralization, partitioning, filtration and the like, or subjected to the next step after isolation of the reaction product by isolation means such as concentration, crystallization and the like. The resultant product may be subjected to the next step after further purification by known purification means such as recrystallization, column chromatography and the like. Among these, from the aspect of productivity, the reaction mixture is preferably subjected as it is to the next step.

A compound represented by the formula (9) may form a solvate such as hydrate or organic solvate or the like, the form thereof may vary depending on the starting material, solvent, and the like to be used, and the form thereof is not particularly limited as long as it does not inhibit the target reaction.

In the present invention, unless particularly indicated, "a compound represented by the formula (9)" means both a compound represented by the formula (9) and a solvate thereof.

Among the compounds represented by the formula (9), the compound represented by the following formula (9b) is a novel compound. Since this compound has ease of crystallizing, it can be easily separated from reaction by-products without complicated purification such as chromatography and the like, and is suitable for industrial production.

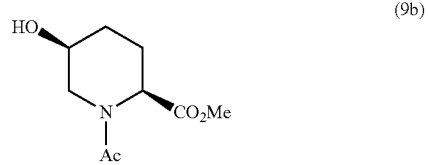

(9b)

wherein Ac is an acetyl group, and Me is a methyl group.

[step 9]

Step 9 is obtaining a compound represented by the formula (1) by reacting the above-mentioned compound represented by the formula (9) obtained in step 8 with a leaving group introduction agent.

(Starting Material)

The leaving group introduction agent is not particularly limited as long as it can introduce a leaving group LG into a compound represented by the formula (9), and a known leaving group introduction agent can be used.

As the leaving group LG in the formula (1), a sulfonyloxy group is particularly preferable. Thus, the leaving group introduction agent is preferably a sulfonyloxylating agent that can introduce the leaving group LG into a compound represented by the formula (9).

Examples of the sulfonyloxylating agent include nitrobenzenesulfonylating agent, toluenesulfonylating agent, methanesulfonylating agent, trifluoromethanesulfonylating agent and the like. From the aspect of reactivity of the introduced leaving group, a nitrobenzenesulfonylating agent is preferable.

The nitrobenzenesulfonylating agent is not particularly limited as long as it can protect an amino group with a nitrobenzenesulfonyl group, and nitrobenzenesulfonyl halide is preferable.

Examples of the nitrobenzenesulfonyl halide include nitrobenzenesulfonyl fluorides such as o-nitrobenzenesulfonyl fluoride, p-nitrobenzenesulfonyl fluoride, 2,4-dinitrobenzenesulfonyl fluoride, 2,3-dinitrobenzenesulfonyl fluoride, 2,5-dinitrobenzenesulfonyl fluoride, 2,6-dinitrobenzenesulfonyl fluoride and the like; nitrobenzenesulfonyl chlorides such as o-nitrobenzenesulfonyl chloride, p-nitrobenzenesulfonyl chloride, 2,4-dinitrobenzenesulfonyl chloride, 2,3-dinitrobenzenesulfonyl chloride, 2,5-dinitrobenzenesulfonyl chloride, 2,6-dinitrobenzenesulfonyl chloride and the like; nitrobenzenesulfonyl bromides such as o-nitrobenzenesulfonyl bromide, p-nitrobenzenesulfonyl bromide, 2,4-dinitrobenzenesulfonyl bromide, 2,3-dinitrobenzenesulfonyl bromide, 2,5-dinitrobenzenesulfonyl bromide, 2,6-dinitrobenzenesulfonyl bromide and the like; and nitrobenzenesulfonyl iodides such as o-nitrobenzenesulfonyl iodide, p-nitrobenzenesulfonyl iodide, 2,4-dinitrobenzenesulfonyl iodide, 2,3-dinitrobenzenesulfonyl iodide, 2,5-dinitrobenzenesulfonyl iodide, 2,6-dinitrobenzenesulfonyl iodide and the like.

Among these, from the aspects of cost and availability of the starting materials, nitrobenzenesulfonyl chloride is preferable, and p-nitrobenzenesulfonyl chloride or o-nitrobenzenesulfonyl chloride is particularly preferable.

Examples of the toluenesulfonylating agent include p-toluenesulfonyl chloride, p-toluenesulfonic anhydride and the like. From the aspects of cost and availability of the starting materials, p-toluenesulfonyl chloride is preferable.

Examples of the methanesulfonylating agent include methanesulfonyl chloride, methanesulfonic anhydride and the like. From the aspects of cost and availability of the starting materials, methanesulfonyl chloride is preferable.

Examples of the trifluoromethanesulfonylating agent include trifluoromethanesulfonyl fluoride, trifluoromethanesulfonyl chloride, and trifluoromethanesulfonic anhydride. From the aspects of cost and availability of the starting materials, trifluoromethanesulfonic anhydride is preferable.

As the amount of the leaving group introduction agent to be used with respect to a compound represented by the formula (9), the lower limit is generally not less than 0.1 molar equivalent, preferably not less than 1 molar equivalent, more preferably not less than 1.02 molar equivalents, from the aspect of productivity, and the upper limit is generally not more than 20 molar equivalents, preferably not more than 10 molar equivalents, more preferably not more than 5 molar equivalents, from the aspects of operability, purity of the reaction product and cost.

Step 9 is preferably performed in the presence of a base in a solvent.

The base is not particularly limited as long as the reaction proceeds. Examples thereof include tertiary amines, pyridines, organic strong base, metal amide, alkyl metal compound, metal hydride, metal alkoxide, carbonate, phosphate, metal hydroxide, cyanide and the like. As the base used in step 9, one kind may be used alone, or two or more kinds may be used in any combination and ratio.

Examples of the tertiary amines include triethylamine, diisopropylethylamine, N-methylmorpholine, quinuclidine, 1,4-diazabicyclo[2.2.2]octane and the like.

Examples of the pyridines include pyridine, 4-dimethylaminopyridine, 2-methylpyridine, 3-methylpyridine, 4-methylpyridine, 2,6-lutidine and the like.

Examples of the organic strong base include 1,8-diazabicyclo[5.4.0]undec-7-ene, tetramethylguanidine and the like.

Examples of the metal amide include lithium amide, sodium ethylamide, calcium diethylamide, lithium diisopropylamide, potassium benzylamide, sodium bis(trimethylsilyl)amide, lithium indolide, sodium pyrrolide, lithium pyrrolide, potassium pyrrolide, potassium pyrrolizide, aluminum diethylpyrrolide, ethylaluminum dipyrrolide, aluminum tripyrrolide, lithium diisopropylamide, sodium hexamethyldisilazide and the like.

Examples of the alkyl metal compound include n-butyllithium, sec-butyllithium, tert-butyllithium, isopropylmagnesium bromide and the like.

Examples of the metal hydride include lithium hydride, sodium hydride, potassium hydride, magnesium hydride, calcium hydride, cesium hydride and the like.

Examples of the metal alkoxide include lithium methyloxide, lithium ethyloxide, lithium propyloxide, lithium tert-butyloxide, sodium methyloxide, sodium ethyloxide, sodium propyloxide, sodium tert-butyloxide, potassium methyloxide, potassium ethyloxide, potassium propyloxide, potassium tert-butyloxide and the like.

Examples of the carbonate include sodium carbonate, potassium carbonate, cesium carbonate, sodium hydrogen carbonate, potassium hydrogen carbonate, cesium hydrogen carbonate and the like.

Examples of the phosphate include sodium phosphate, sodium hydrogen phosphate, sodium dihydrogen phosphate, potassium phosphate, potassium hydrogen phosphate, potassium dihydrogen phosphate and the like.

Examples of the metal hydroxide include lithium hydroxide, sodium hydroxide, potassium hydroxide, calcium hydroxide and the like.

Examples of the cyanide include sodium cyanide, potassium cyanide and the like.

Among these bases, from the aspect of the strength of the basicity, tertiary amines and pyridines are preferable, and trimethylamine is more preferable.

As the amount of the base to be used with respect to a compound represented by the formula (9), the lower limit is generally not less than 0.1 molar equivalent, preferably not less than 1 molar equivalent, more preferably not less than 1.02 molar equivalents, from the aspect of productivity, and the upper limit is generally not more than 30 molar equivalents, preferably not more than 20 molar equivalents, more preferably not more than 10 molar equivalents.

The solvent is not particularly limited as long as the reaction proceeds, and organic solvent or aqueous solvent can be used. From the aspect of reactivity, an organic solvent is preferably used.

As the organic solvent, at least one kind of solvent selected from the group consisting of alcohol solvent, ester solvent, ether solvent, ketone solvent, nitrile solvent, amide solvent, sulfoxide solvent, hydrocarbon solvent, and basic organic solvent can be used.

Examples of the alcohol solvent include alcohol represented by the formula ROH (R is as defined above). Preferably, alcohol having an aliphatic hydrocarbon group having 1-8 carbon atoms or an aromatic hydrocarbon group having 6-8 carbon atoms can be used. For example, methanol, ethanol, propanol, butanol, pentanol, hexanol, heptanol, octanol, benzyl alcohol, phenylethyl alcohol or these isomer alcohol and the like can be used.

As the ester solvent, acetic acid esters such as ethyl acetate, propyl acetate, butyl acetate and the like can be used.

As the ether solvent, chain ethers such as diethyl ether, di-n-butyl ether, diisopropyl ether, di-n-butyl ether, tert-butyl methyl ether and the like; and cyclic ethers such as cyclopentyl methyl ether, tetrahydrofuran, 2-methyltetrahydrofuran, dioxane and the like can be used.

As the ketone solvent, aliphatic ketones such as acetone, methyl ethyl ketone, methyl isobutyl ketone and the like can be used.

As the nitrile solvent, aliphatic nitriles such as acetonitrile, propanonitrile, butyronitrile, isobutyronitrile, valeronitrile, isovaleronitrile and the like; aromatic nitriles such as benzonitrile and the like can be used.

As the amide solvent, aprotic amides such as N,N-dimethylformamide, N,N-dimethylacetamide, N-methylpyrrolidinone and the like can be used.

As the sulfoxide solvent, aprotic sulfoxides such as dimethyl sulfoxide and the like can be used.

As the hydrocarbon solvent, aliphatic hydrocarbons such as hexane, cyclohexane, heptane, cycloheptane and the like; aromatic hydrocarbons such as toluene, xylene and the like can be used.

As the basic organic solvent, for example, pyridine, 2-methylpyridine, 3-methylpyridine, 4-methylpyridine, 2,6-dimethylpyridine and the like can be used.

The solvent is preferably an ester solvent, more preferably ethyl acetate.

As the solvent, the above-mentioned organic solvent may be used alone, or two or more kinds thereof mixed at any ratio may be used.

The lower limit of the amount of the solvent to be used is generally not less than 1 L, preferably not less than 2 L, further preferably not less than 3 L, per 1 kg of the compound represented by the formula (9), from the aspect of operability, and the upper limit thereof is generally not more than 30 L, preferably not more than 20 L, more preferably not more than 15 L, per 1 kg of the compound represented by the formula (9), from the aspects of operability, productivity and cost.

(Reaction Conditions)

The reaction temperature may vary depending on the leaving group introduction agent, base, solvent and the like to be used. The lower limit is generally not less than 0° C., preferably not less than 5° C., more preferably not less than 10° C., from the aspect of productivity, and the upper limit is generally not more than 50° C., preferably not more than 40° C., more preferably not more than 30° C., from the aspects of the purity of the reaction product and cost.

The reaction time may vary depending on the leaving group introduction agent, base, solvent and the like to be used. It is generally 0.5 hr-24 hr, preferably 1-12 hr.

The reaction is generally performed under normal pressure.

When a compound represented by the formula (9) and a leaving group introduction agent are reacted, the order of supply of these compounds can be appropriately selected. These compounds may be supplied all at once to the reaction system or supplied in plural divided portions. For example, in a reactor, one or more kinds of any of a compound represented by the formula (9) and a leaving group introduction agent are supplied together with a solvent, and using this as a base solution, the reaction can be performed by supplying the remaining components as a supply solution under reaction conditions. The base may be present in the reaction system from the start, or may be supplied in the middle, or it may be supplied all at once or supplied in plural divided portions.

(Post-Treatment)

The reaction mixture may be subjected as it is to the next step, or subjected to the next step after treatments such as neutralization, partitioning, filtration and the like, or subjected to the next step after isolation of the reaction product by isolation means such as concentration, crystallization and the like. The resultant product may be subjected to the next step after further purification by known purification means such as recrystallization, column chromatography and the like. Among these, from the aspect of productivity, the reaction mixture is preferably subjected as it is to the next step.

The compound represented by the formula (1) may form a solvate such as hydrate or organic solvate. The form thereof may vary depending on the starting material, solvent, and the like to be used. The form thereof is not particularly limited as long as it does not inhibit the desired reaction.

In the present invention, unless particularly indicated, the "compound represented by the formula (1)" means both a compound represented by the formula (1) and a solvate thereof.

Among the compounds represented by the general formula (1), the compound represented by the following formula (1a) is a novel compound. Since this compound has ease of crystallizing, it can be easily separated from reaction by-products without complicated purification such as chromatography and the like, and is suitable for industrial production.

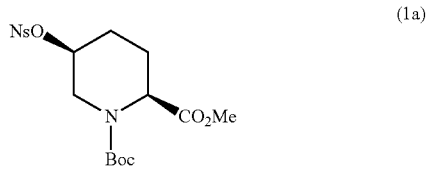

wherein Boc is a tert-butyloxycarbonyl group, Ns is a p-nitrobenzenesulfonyl group, and Me is a methyl group.

<Production Method 5>

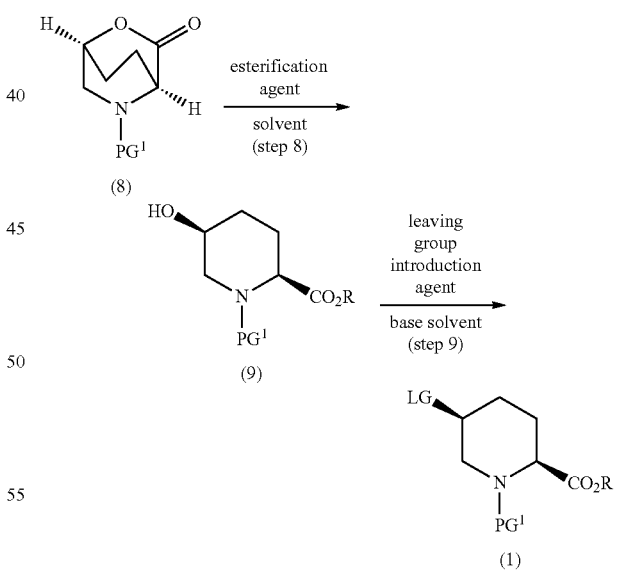

wherein each symbol is as defined above.

Production method 5 is characterized in that it contains obtaining a compound represented by the formula (9) by reacting a compound represented by the formula (8) with an esterification agent (step 8); and obtaining a compound represented by the formula (1) by reacting a compound represented by the formula (9) with a leaving group introduction agent (step 9).

The step 8 and step 9 of the production method 5 are as explained in the above-mentioned <Production method 4>.

The production method 5 is suitable for industrial production because many of the compounds produced as intermediates have low polarity and ease of crystallizing, and operations such as extraction, recrystallization and the like can be efficiently performed.

<Production Method 6>

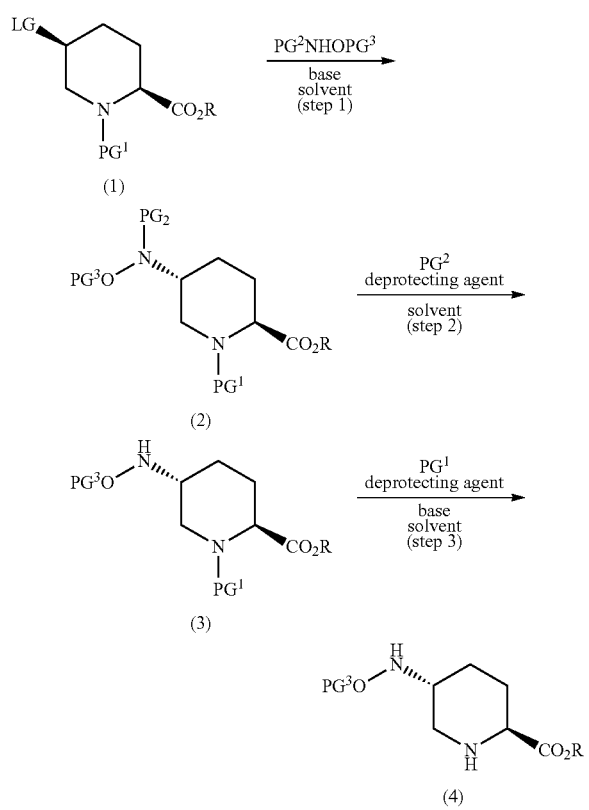

wherein each symbol is as defined above.

Production method 6 is characterized in that it contains reacting a compound represented by the formula (1) with a hydroxylamine derivative represented by the formula $PG^2NHOPG^3$ in the presence of a base in a solvent to obtain a compound represented by the formula (2) (step 1);

obtaining a compound represented by the formula (3) or a salt thereof by reacting the compound represented by the formula (2) obtained in step 1 with a $PG^2$ deprotecting agent (step 2); and obtaining a compound represented by the formula (4) or a salt thereof by reacting the compound represented by the formula (3) or a salt thereof obtained in step 2 with a PG' deprotecting agent (step 3).

That is, production method 6 has production route A of the present invention.

The step 1-step 3 of the production method 6 are as explained in the above-mentioned <production method 1> and <production method 2>.

In addition, production method 6 may further has the following steps

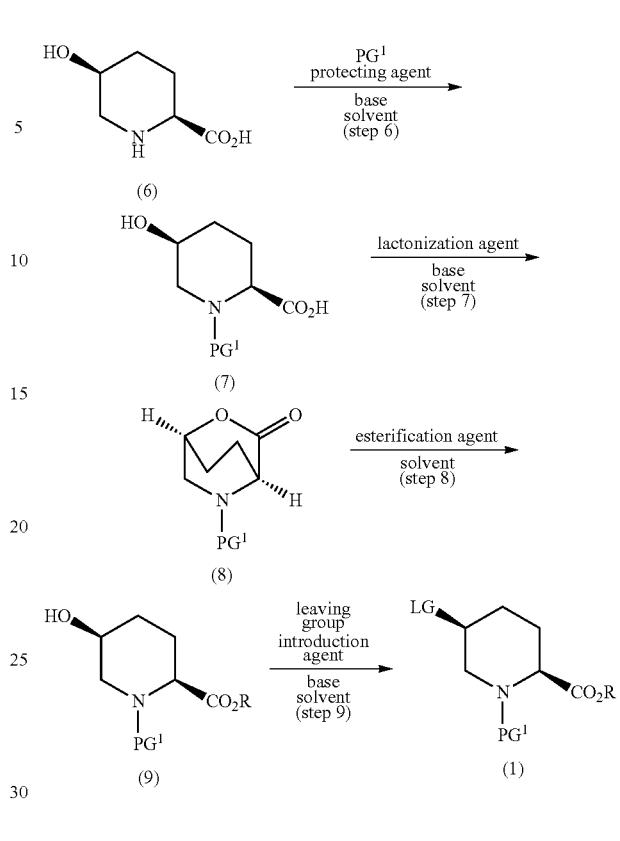

wherein each symbol is as defined above,

The step 6-step 9 of the production method 6 are as explained in the above-mentioned <Production method 4>.

Production method 6 is suitable for industrial production because intermediates with high purity can be obtained, the reaction can be performed under mild conditions, and unreacted products can be removed with ease.

<Production Method 7>

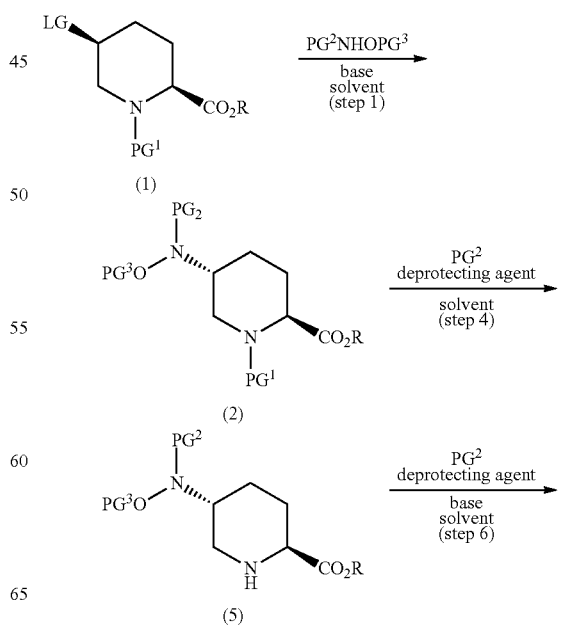

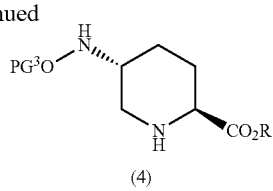

wherein each symbol is as defined above.

Production method 7 is characterized in that it contains reacting a compound represented by the formula (1) with a hydroxylamine derivative represented by the formula $PG^2NHOPG^3$ in the presence of a base in a solvent to obtain a compound represented by the formula (2) (step 1);

obtaining a compound represented by the formula (5) or a salt thereof by reacting the compound represented by the formula (2) obtained in step 1 with a $PG^1$ deprotecting agent (step 4); and obtaining a compound represented by the formula (4) or a salt thereof by reacting the compound represented by the formula (5) or a salt thereof obtained in step 4 with a $PG^2$ deprotecting agent (step 5).

That is, production method 7 has production route B of the present invention.

The step 1, step 4 and step 5 of the production method 7 are as explained in the above-mentioned <production method 1> and <production method 3>.

In addition, production method 7 may further have the following steps.

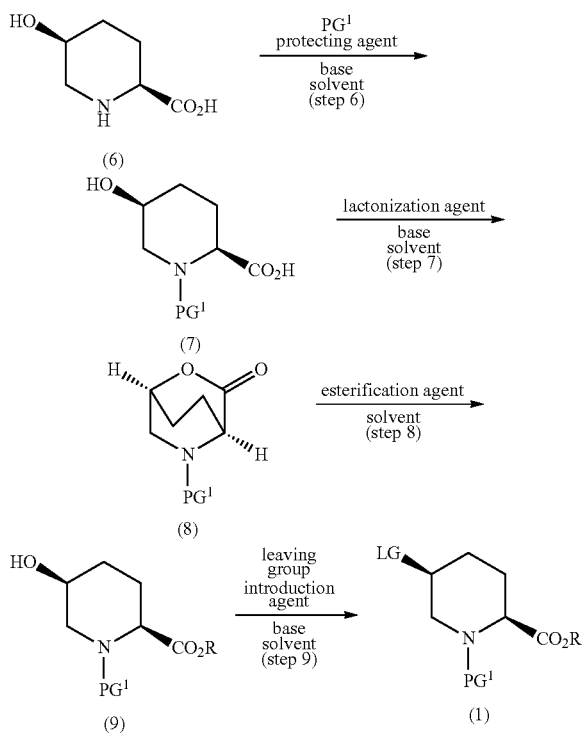

wherein each symbol is as defined above.

The step 6-step 9 of the production method 7 are as explained in the above-mentioned <Production method 4>.

Production method 7 is suitable for industrial production because intermediates with high purity can be obtained, the reaction can be performed under mild conditions, and unreacted products can be removed with ease.

EXAMPLE

The present invention is explained in more detail in the following by referring to Examples; however, the present invention is not limited by these Examples.

In the following Examples, the ratio of the 2-position isomer of the obtained compound was measured under the following HPLC analysis conditions.

(HPLC Analysis Conditions)

TABLE 1

| analysis instrument | Agilent 1100 | |
|---|---|---|
| column | Unison UK-C18 3 μm 4.6 mm I.D. × 250 mm | |
| mobile phase A | 0.1 vol % aqueous phosphoric acid solution | |
| mobile phase B | acetonitrile | |

| gradient | time (min) | mobile phase A (%) | mobile phase B (%) |
|---|---|---|---|
| | 0-3 | 95 | 5 |
| | 3-15 | 95→35 | 5→65 |
| | 15-30 | 35→20 | 65→80 |

| flow | 1 mL/min |
|---|---|
| injection volume | 5 μL |
| detection wavelength | 210 nm |
| column temperature | 40° C. |

Example 1: Step 6→Step 7→Step 8→Step 9

[Step 6]

Production of (2S,5S)-1-(tert-butyloxycarbonyl)-5-hydroxypiperidine-2-carboxylic acid

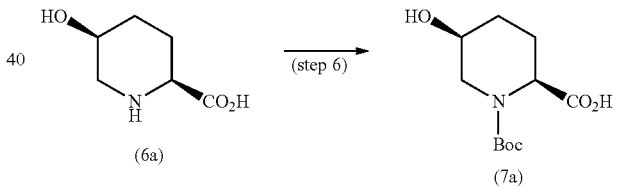

The starting material (2S,5S)-5-hydroxypiperidine-2-carboxylic acid (hereinafter to be referred to as compound (6a)) was synthesized according to the method described in WO 2015/099126.

In a separable flask, compound (6a) (100.0 g, 0.689 mol) was dissolved in water (500 g). To the obtained solution were added di-tert-butyl dicarbonate (195.5 g, 0.897 mol) and triethylamine (146.4 g, 1.448 mol) at 30° C. After stirring at 25° C. for 1 hr, triethylamine (146.4 g, 1.448 mol) was added again, and the mixture was further stirred at 25° C. for 6 hr.

To the obtained reaction mixture was added toluene (200 mL), and the mixture was stirred and the organic layer was removed. The obtained aqueous layer was cooled to 5° C., pH was adjusted to 2.0 by adding 35 wt % hydrochloric acid, and the mixture was extracted with ethyl acetate (500 mL ×2, 300 mL ×1). The recovered organic layers were combined, the organic layer was washed with water (100 mL), and the solvent was evaporated to adjust the liquid amount to 600 mL. To the obtained residue was added n-heptane (400 mL), separately prepared seed crystals of (2S,5S)-1-(tert-butyloxycarbonyl)-5-hydroxypiperidine-2-carboxylic acid (hereinafter to be referred to as compound (7a)) were inoculated and matured to allow for crystal precipitation. n-Heptane (1000 mL) was further added, cooling matured at −5° C., and the obtained crystals were collected by filtration to give the object compound (7a) as a white powder (156.9 g, yield 92.9%).

¹H-NMR (400 MHz, CDCl₃) δ 1.24-1.33 (1H, m), 1.43-1.47 (9H, m), 1.66-1.76 (1H, m), 1.99 (1H, d, J=10.8 Hz), 2.28-2.30 (1H, m), 2.65-2.81 (1H, m), 3.63 (1H, m), 4.09-4.15 (1H, m), 4.688-4.84 (1H, m)

[Step 7→Step 8]
Production of methyl (2S,5S)-1-(tert-butyloxycarbonyl)-5-hydroxy-piperidine-2-carboxylate

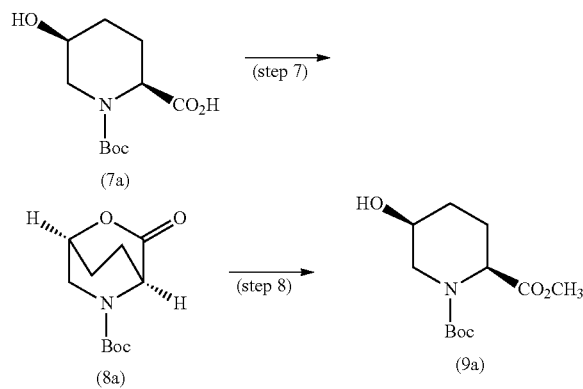

Under a nitrogen atmosphere, in a separable flask, compound (7a) (11.0 g, 0.0448 mol) obtained in the above-mentioned [step 6] was dissolved in tetrahydrofuran (33 mL). To the obtained solution were added triethylamine (5.44 g, mol) and acetic anhydride (5.04 g, 0.0494 mol) at 20° C., and the mixture was reacted at 20° C. for 6 hr.

To the obtained reaction mixture was added methanol (33 mL), and the mixture was cooled to 5° C. 5 mol/L sodium methoxide methanol solution (20.6 mL, 0.103 mol) was added, and the mixture was reacted at 5° C. for 1 hr. To the obtained reaction mixture were added acetic acid (3.77 g, 0.063 mol) and water (33 mL), and methanol and tetrahydrofuran were evaporated. The residue was extracted with ethyl acetate (66 mL). The obtained organic layer was washed with 5 wt % aqueous sodium hydrogen carbonate solution (22 mL), and the solvent was evaporated to give crude methyl (2S,5S)-1-(tert-butyloxycarbonyl)-5-hydroxy-piperidine-2-carboxylate (hereinafter to be referred to as compound (9a)) as a colorless oil (12.6 g (10.4 g in terms of pure amount) (yield 89.1%).

¹H-NMR (400 MHz, CDCl₃) δ 1.17-1.28 (1H, m), 1.44-1.47 (9H, m), 1.68-1.78 (1H, m), 1.96-2.00 (1H, m), 2.27-2.30 (1H, m), 2.63-2.79 (1H, m), 3.62-3.64 (1H, m), 3.74 (3H, s), 4.09-4.21 (1H, m), 4.67-4.85 (1H, m)

[Step 9]
Production of methyl (2S,5S)-1-(tert-butyloxycarbonyl)-5-(p-nitrobenzenesulfonyloxy)-piperidine-2-carboxylate

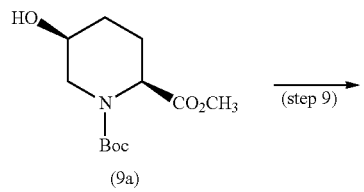

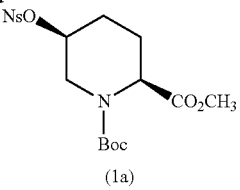

Under a nitrogen atmosphere, in a separable flask, ethyl acetate was added to a crude compound (9a) (12.6 g (10.4 g in terms of pure amount, 0.0400 mol) obtained in the above-mentioned [step 7→step 8] to adjust the liquid amount to 83.2 mL. To the obtained solution were added triethylamine (14.5 g, mol) and p-nitrobenzenesulfonyl chloride (15.9 g, 0.0720 mol) at 15° C., and the mixture was stirred at 15° C. for 4 hr.

To the obtained reaction mixture was added water (41 mL) and the mixture was stirred and the aqueous layer was discarded. Then, water (31 mL) and acetic acid (2.44 g) were added, the mixture was stirred and the aqueous layer was discarded. Furthermore, the organic layer was washed with 5 wt % aqueous sodium hydrogen carbonate solution (30.9 mL) and water (10 mL). The obtained organic layer was concentrated to adjust the liquid amount to 32 mL, n-heptane (21 mL) was added at 45° C., separately prepared seed crystals of methyl (2S,5S)-1-(tert-butyloxycarbonyl)-5-(p-nitrobenzenesulfonyloxy)-piperidine-2-carboxylate were inoculated, n-heptane (62 mL) was further added, and crystals were allowed to precipitate. After cooling maturation at 5° C., the obtained crystals were collected by filtration to give methyl (2S,5S)-1-(tert-butyloxycarbonyl)-5-(p-nitrobenzenesulfonyloxy)-piperidine-2-carboxylate (hereinafter to be referred to as compound (1a)) as a pale-yellow powder (16.1 g, yield 90.6%).

¹H-NMR (400 MHz, CDCl₃) δ 1.41-1.48 (10H, m), 1.69-1.75 (1H, m), 1.97-2.12 (1H, m), 2.27-2.33 (1H, m), 2.78-2.99 (1H, m), 3.73-3.74 (3H, m), 4.06-4.20 (1H, m), 4.49-4.58 (1H, m), 4.64-4.84 (1H, m), 8.12-8.14 (2H, m), 8.41-8.43 (2H, m)

Example 2

[Step 7]
Production of (1S,4S)-5-(tert-butyloxycarbonyl)-2-oxa-5-azabicyclo[2.2.2]octan-3-one

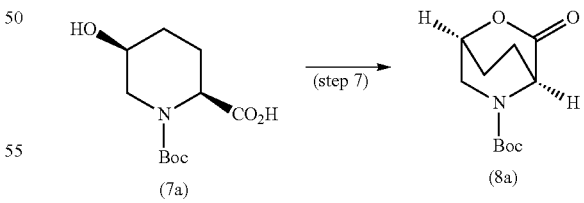

Under a nitrogen atmosphere, in a separable flask, compound (7a) (3.00 g, 0.0122 mol) obtained in Example 1 [step 6] was dissolved in ethyl acetate (12 mL). To the obtained solution were added triethylamine (1.48 g, 0.0147 mol) and acetic anhydride (1.37 g, 0.0134 mol) at 20° C., and the mixture was reacted at 20° C. for 6 hr.

The obtained reaction mixture was washed with water (9 mL) and 5 wt % aqueous sodium hydrogen carbonate solution (9 mL). The organic layer was dried over anhydrous magnesium sulfate and filtered. The filtrate was concentrated to give the object compound (1S,4S)-5-(tert-butyloxycarbonyl)-2-oxa-5-azabicyclo[2.2.2]octan-3-one (hereinafter to be referred to as compound (8a)) as a white powder (2.65 g) (yield 95.4%).

$^1$H-NMR (400 MHz, CDCl$_3$) δ 1.47 (9H, s), 1.81-1.84 (1H, m), 1.97-2.22 (3H, m), 3.44-3.47 (1H, m), 3.63 (1H, d, J=11.6 Hz), 4.60-4.83 (2H, m)

Example 3: Step 1→Step 2→Step 3

[Step 1]
Production method of methyl (2S,5R)-1-(tert-butyloxycarbonyl)-5-(N-benzyloxy-p-nitrobenzenesulfonylamino)-piperidine-2-carboxylate

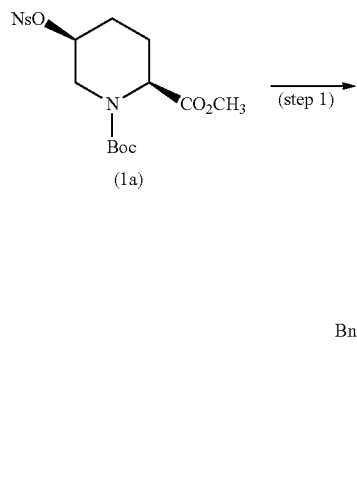

Under a nitrogen atmosphere, in a separable flask, compound (1a) (20 g, 0.0450 mol) obtained in Example 1 [step 9] was dissolved in N,N-dimethylformamide (hereinafter to be referred to as DMF) (80 mL). To the obtained solution were added N-(p-nitrobenzenesulfonyl)-O-benzyl-hydroxylamine (14.98 g, 0.0486 mol) and potassium carbonate (6.71 g, 0.0486 mol), and the mixture was stirred at 35° C. for 30 hr until the reaction conversion ratio reached not less than 99%. The ratio of the 2-position isomer in the obtained reaction mixture was (2S,5R):(2R,5R)=99.2:0.8 (HPLC).

To the obtained reaction mixture were added toluene (100 mL) and water (64.5 mL), the pH was adjusted to 4.8 with acetic acid for partitioning, and the aqueous layer was extracted again with toluene (40 mL). The organic layers were combined, water (80 mL) was added, potassium carbonate was added until the pH of the aqueous layer reached not less than 9, and the aqueous layer was discarded. The organic layer was dried over anhydrous magnesium sulfate, filtered, and the solvent was evaporated to give crude compound (2a) as a pale-yellow oil (30.96 g (21.55 g in terms of pure amount) (yield 87.0%).

$^1$H-NMR (400 MHz, DMSO-d$_6$) δ 1.32 (9H, s), 1.48-1.57 (1H, m), 1.73-1.76 (2H, m), 2.03-2.10 (1H, m), 3.19 (1H, m), 3.65-3.71 (4H, m), 3.89 (1H, d, J=12.0 Hz), 4.48-4.51 (1H, m), 5.01-5.07 (2H, m), 7.40-7.45 (5H, m), 8.12-8.15 (2H, m), 8.42-8.46 (2H, m)

[Step 2]
Production method of methyl (2S,5R)-1-(tert-butyloxycarbonyl)-5-(benzyloxyamino)-piperidine-2-carboxylate

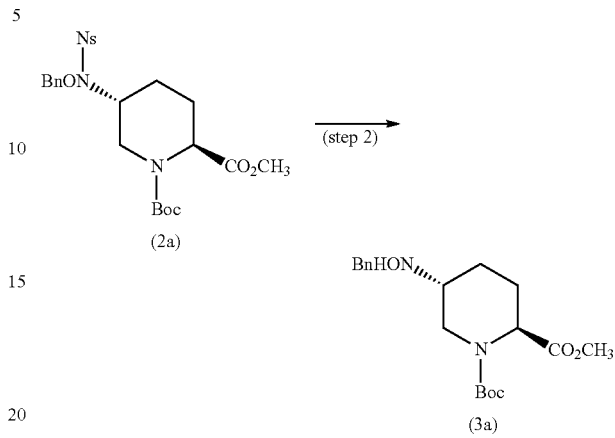

Under a nitrogen atmosphere, in a separable flask, crude compound (2a) (31.9 g (21.4 g in terms of pure amount, 0.0390 mol) obtained by a method similar to that in the above-mentioned [step 1] was dissolved in methanol (128 mL). To the obtained solution were added thioglycolic acid (14.3 g, 0.156 mol) and potassium carbonate (43.0 g, 0.312 mol) at 25° C., and the mixture was stirred at 25° C. for 18 hr, and the solvent was evaporated.

To the obtained residue were added water (228 mL), toluene (128 mL), and ethyl acetate (102 mL). Furthermore, the mixture was neutralized with acetic acid to pH6, and the aqueous layer was discarded. To the organic layer was added water (70 mL), potassium carbonate was added to pH9, and the aqueous layer was discarded. The organic layer was dried over anhydrous magnesium sulfate, filtered, and the solvent was evaporated to give crude methyl (2S,5R)-1-(tert-butyloxycarbonyl)-5-(benzyloxyamino)-piperidine-2-carboxylate (hereinafter to be referred to as compound (3a)) as a pale-yellow oil (20.8 g (13.2 g in terms of pure amount) (yield 92.8%).

$^1$H-NMR (400 MHz, CDCl$_3$) δ 1.46-1.59 (10H, m), 1.67-1.70 (1H, m), 1.88-2.04 (2H, m), 3.05-3.21 (2H, m), 3.74 (3H, s), 4.18 (1H, d, J=12.4 Hz), 4.68-4.76 (2H, m), 4.91 (1H, br), 5.46 (1H, br), 7.29-7.36 (5H, m)

[Step 3]
Production method of methyl (2S,5R)-5-(benzyloxyamino)-piperidine-2-carboxylate 2 hydrochloride

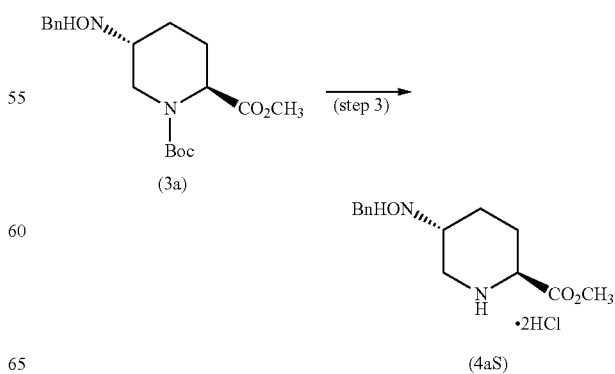

Under a nitrogen atmosphere, in a separable flask, a crude compound (3a) (9.38 g (7.01 g in terms of pure amount, mol) obtained in the above-mentioned [step 2] was dissolved in methanol (15.2 g). The obtained solution was added dropwise to 2 mol/L hydrochloric acid methanol solution (28.8 mL) adjusted to temperature 45° C., and the mixture was stirred at 45° C. for 4 hr.

The obtained reaction mixture was cooled to −5° C., filtered, and the obtained solid was dried to give methyl (2S,5R)-5-(benzyloxyamino)-piperidine-2-carboxylate 2 hydrochloride (hereinafter to be referred to as compound (4 aS)) as a white powder (6.17 g) (yield 95.2%).

$^1$H-NMR (400 MHz, D$_2$O) δ 1.67-1.89 (2H, m), 2.12-2.15 (1H, m), 2.43-2.47 (1H, m), 3.05 (1H, t, J=12.0 Hz), 3.50-3.56 (1H, m), 3.71-3.75 (1H, m), 3.81 (3H, s), 4.04-4.08 (1H, m), 4.90 (2H, s), 7.43 (5H, s)

Example 4: Step 1→Step 4→Step 5

[Step 1→Step 4]
Production method of methyl (2S,5R)-5-(N-benzyloxy-p-nitrobenzenesulfonylamino)-piperidine-2-carboxylate

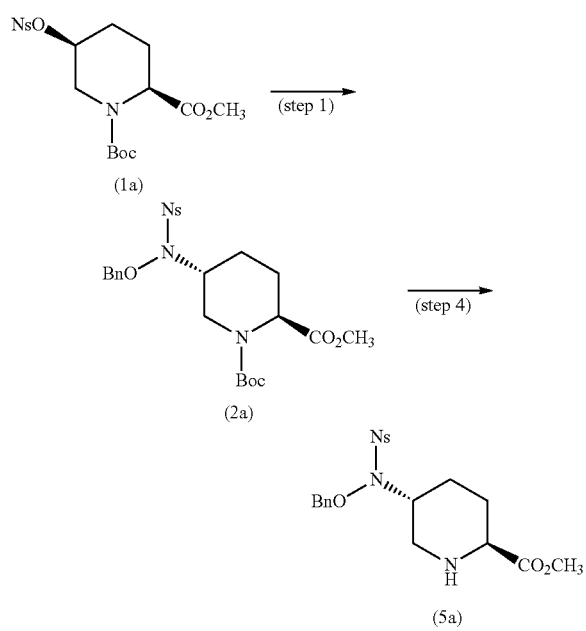

Under a nitrogen atmosphere, in a test tube, compound (1a) (2.16 g, 4.86 mmol) was dissolved in DMF (10 mL). To the obtained solution were added N-(p-nitrobenzenesulfonyl)-O-benzyl-hydroxylamine (1.65 g, 5.35 mmol) and potassium carbonate (0.74 g, 5.35 mmol), and the mixture was stirred at 65° C. for 24 hr.

The obtained reaction mixture was subjected to solvent extraction and water washing treatment, dried over anhydrous magnesium sulfate, and filtered. The solvent was evaporated. To the obtained residue was added 0.5 mol/L hydrochloric acid methanol solution, and the mixture was stirred at 65° C. for 17 hr.

The obtained reaction mixture was concentrated and the obtained residue was subjected to partitioning extraction by adding ethyl acetate and 5 wt % aqueous sodium hydrogen carbonate solution, and the aqueous layer was discarded. The obtained organic layer was concentrated to give methyl (2S,5R)-carboxylate (hereinafter to be referred to as compound (5a)) as a yellow oil (1.45 g, yield 88.7%).

$^1$H-NMR (400 MHz, CDCl$_3$) δ 1.26-1.51 (2H, m), 1.95-2.04 (2H, m), 2.52 (1H, dd), 3.14 (1H, dd), 3.51 (1H, m), 3.71-3.73 (4H, m), (2H, brs), 7.26-7.41 (5H, m), 8.08-8.13 (2H, m), 8.32-8.37 (2H, m)

[Step 5]
Production method of methyl (2S,5R)-5-(N-benzyloxyamino)-piperidine-2-carboxylate 2 hydrochloride

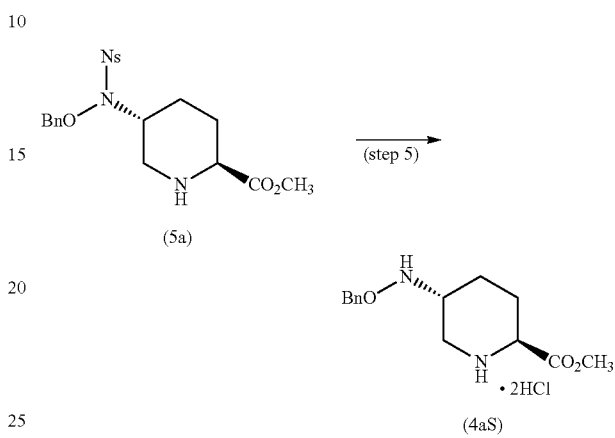

Under a nitrogen atmosphere, in a test tube, compound (5a) (4.2 g, 9.35 mmol) obtained by a method similar to that in the above-mentioned [step 1→step 4] was dissolved in methanol (42 mL). To the obtained solution were added thioglycolic acid (3.4 g, 37.42 mmol) and potassium carbonate (9.9 g, 74.8 mmol) at 25° C., and the mixture was stirred at 25° C. for 19 hr.

To the obtained reaction mixture were added water and ethyl acetate and, after partitioning extraction, the aqueous layer was discarded. The obtained organic layer was washed with 5 wt % aqueous sodium hydrogen carbonate solution. The organic layer was dried over anhydrous magnesium sulfate, filtered, and the solvent was evaporated to give a residue (1.27 g). To the obtained residue was added 0.5 mol/L hydrochloric acid methanol solution (48 mL), and the mixture was stirred at 60° C. for 19 hr. The obtained reaction mixture was concentrated to give methyl (2S,5R)-5-(N-benzyloxyamino)-piperidine-2-carboxylate 2 hydrochloride (hereinafter to be referred to as compound (4 aS)) as pale-red crystals (1.27 g, yield 78%).

$^1$H-NMR (400 MHz, D$_2$O) δ 1.67-1.89 (2H, m), 2.13 (1H, m), 2.45 (1H, m), 3.05 (1H, t, J=12.0 Hz), 3.53 (1H, m), 3.73 (1H, m), 3.81 (3H, s), 4.06 (1H, m), 4.90 (2H, s), 7.43 (5H, m)

Example 5: Step 8→Step 9

[Step 8]
Production method of methyl (2S,5S)-1-acetyl-5-hydroxy-piperidine-2-carboxylate

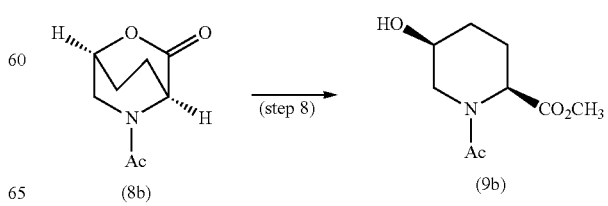

Under a nitrogen atmosphere, in a test tube, (1S,4S)-5-acetyl-2-oxa-5-azabicyclo[2.2.2]octan-3-one (10.0 g (59.17 mmol) synthesized according to the method described in WO 2015/099126 was dissolved in methanol (30 mL). To the obtained solution was added p-toluenesulfonic acid monohydrate (5.6 g, 29.6 mmol) at room temperature, and the mixture was heated to ° C. and stirred at 60° C. for 1.5 hr.

The obtained reaction mixture was concentrated to give a colorless transparent oily residue (14.3 g) containing methyl (2S,5S)-1-acetyl-5-hydroxy-piperidine-2-carboxylate (hereinafter to be referred to as compound (9b)).

¹H-NMR (400 MHz, CDCl₃) δ 1.28-1.32 (2H, m), 1.61-1.70 (1H, m), 1.96-2.00 (1H, m), 2.20 (3H, s), 3.02 (1H, dd), 3.61-3.69 (1H, m), 3.73 (3H, s), 3.90 (1H, dd), 5.25 (1H, d)

[Step 9]
Production method of methyl (2S,5S)-1-acetyl-5-(p-nitrobenzenesulfonyloxy)-piperidine-2-carboxylate

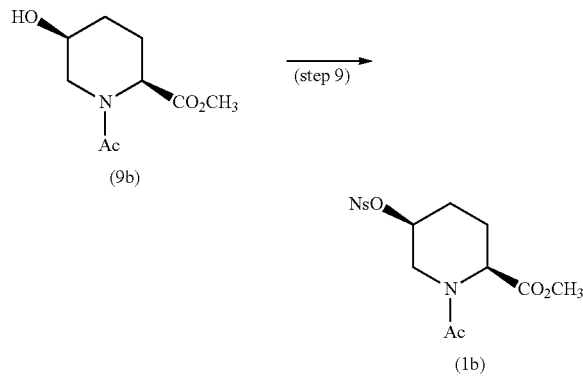

Under a nitrogen atmosphere, in a test tube, an oily residue (11.9 g, 59.17 mmol) containing compound (9b) obtained in the above-mentioned [step 8] was dissolved in ethyl acetate (83 mL). To the obtained solution were added triethylamine (30 g, 295.85 mmol) and p-nitrobenzenesulfonyl chloride (14.3 g, 65.09 mmol) at 30° C. and the mixture was heated and stirred at ° C. for 16 hr.

The obtained reaction mixture was successively washed with water, 10% aqueous acetic acid solution, and 5 wt % sodium bicarbonate water, and the organic layer was concentrated. The obtained residue was purified by silica gel column using a mixed solvent of ethyl acetate/n-heptane=2/8 (volume ratio) to give methyl (2S,5S)-1-acetyl-5-(p-nitrobenzenesulfonyloxy)-piperidine-2-carboxylate (hereinafter to be referred to as compound (1b)) as a colorless oil (6.68 g, consistent yield 29.2% from step 8).

Example 6: Step 1→Step 2→Step 3

[step 1]
Production method of methyl (2S,5R)-1-acetyl-5-(N-benzyloxy-p-nitrobenzenesulfonylamino]-piperidine-2-carboxylate

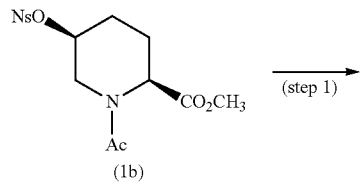

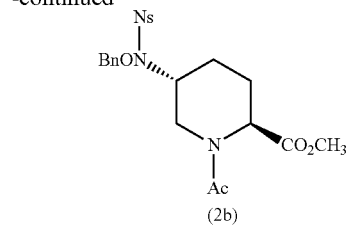

Under a nitrogen atmosphere, in a test tube, compound (1b) (1.1 g, 2.85 mmol) obtained in Example 5 [step 9] was dissolved in DMF (10 mL). To the obtained solution were added N-(p-nitrobenzenesulfonyl)-O-benzyl-hydroxylamine (0.95 g, 3.08 mmol) and potassium carbonate (0.43 g, 3.08 mmol), and the mixture was stirred at 65° C. for 7 hr.

To the obtained reaction mixture was added toluene (50 mL), and the organic layer was successively washed with 10% aqueous acetic acid solution and 5 wt % aqueous sodium hydrogen carbonate solution. The organic layer was dried over anhydrous magnesium sulfate, filtered, and the solvent was evaporated. The obtained residue was purified by silica gel column using a mixed solvent of ethyl acetate/n-heptane=1:1 (volume ratio) to give crude methyl (2S,5R)-1-acetyl-5-(N-benzyloxy-p-nitrobenzenesulfonylamino]-piperidine-2-carboxylate (hereinafter to be referred to as compound (2b)) as a pale-yellow oil (1.34 g (1.02 g in terms of pure amount) (yield 73.0%).

(2S,5R):(2R,5R)=91.2:8.8 (HPLC)

[Step 2]
Production method of methyl (2S,5R)-1-acetyl-5-(benzyloxyamino)-piperidine-2-carboxylate

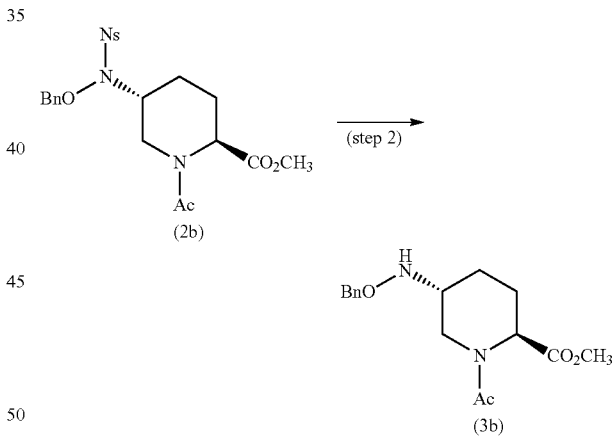

Under a nitrogen atmosphere, in a test tube, compound (2b) (1.0 g (2.08 mmol) obtained in the above-mentioned [step 1] was dissolved in methanol (20 mL). To the obtained solution were added thioglycolic acid (0.77 g, 8.32 mmol) and potassium carbonate (2.3 g, 16.64 mmol) at 25° C., and the mixture was stirred at 25° C. for 13 hr, and the solvent was evaporated.

To the obtained residue were added water and ethyl acetate, and the aqueous layer was discarded. The organic layer was dried over anhydrous magnesium sulfate and filtered, and the solvent was evaporated to give crude methyl (2S,5R)-1-acetyl-5-(benzyloxyamino)-piperidine-2-carboxylate (hereinafter to be referred to as compound (3b)) as a pale-yellow oil (0.37 g (0.31 g in terms of pure amount) (yield 43.8%).

$^1$H-NMR (400 MHz, CDCl$_3$) δ 1.63-1.66 (2H, m), 1.77-1.82 (1H, m), 1.98-2.02 (1H, m), 2.16 (1H, s), 3.21 (1H, m), 3.33 (1H, dd), 4.01 (1H, dd), 4.67-4.74 (2H, m), 5.33 (1H, m), 7.27-7.36 (5H, m)

[Step 3]
Production method of methyl (2S,5R)-5-(benzyloxyamino)-piperidine-2-carboxylate 2 hydrochloride

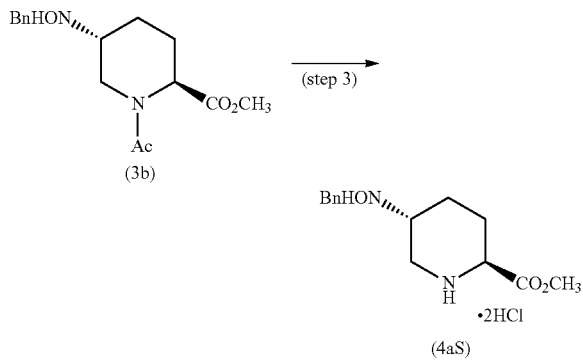

Under a nitrogen atmosphere, in a test tube, to crude compound (3b) (0.15 g (as pure amount) (0.44 mmol) obtained in the above-mentioned [step 2] was added a mixed solvent (5 mL) of 2 mol/L hydrochloric acid methanol solution, and the mixture was stirred at 70° C. for 5 hr.

The obtained reaction product was cooled to room temperature and concentrated. To the obtained concentrate was added ethyl acetate (10 mL) to give compound (4 aS) (0.1 g, yield 68.2%).
(2S,5R):(2R,5R)=98.4:1.6 (HPLC)
$^1$H-NMR (400 MHz, D$_2$O) δ 1.67-1.89 (2H, m), 2.13 (1H, m), 2.45 (1H, m), 3.05 (1H, t, J=12.0 Hz), 3.53 (1H, m), 3.73 (1H, m), 3.81 (3H, s), 4.06 (1H, m), 4.90 (2H, s), 7.43 (5H, m)

Example 7

[Step 1]
Production method of methyl (2S,5R)-1-(tert-butyloxycarbonyl)-5-(N-benzyloxy-p-nitrobenzenesulfonylamino)-piperidine-2-carboxylate

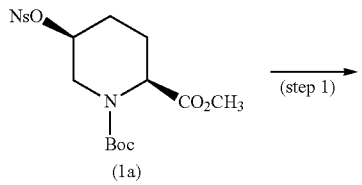

The reaction was performed under the same conditions as in Example 3 except that, in Example 3 [step 1], the amounts of the compound and the solvent used in the reaction were changed to ½₀-fold amounts, the reaction temperature was changed to 25° C., and the stirring time was changed to 37 hr to ensure reaction until the reaction conversion ratio reaches not less than 99%. As a result, the ratio of the 2-position isomer in the obtained reaction mixture was (2S,5R):(2R,5R)=99.3:0.7 (HPLC).

Example 8

[Step 1]
Production method of methyl (2S,5R)-1-(tert-butyloxycarbonyl)-5-(N-benzyloxy-p-nitrobenzenesulfonylamino)-piperidine-2-carboxylate The reaction was performed under the same conditions as in Example 3 except that, in Example 3 [step 1], the amounts of the compound and the solvent used in the reaction were changed to ½₀-fold amounts, the reaction temperature was changed to 45° C., and the stirring time was changed to 23 hr to ensure reaction until the reaction conversion ratio reaches not less than 99%. As a result, the ratio of the 2-position isomer in the obtained reaction mixture was (2S,5R):(2R,5R)=98.5:1.5 (HPLC).

Example 9

[Step 1]
Production method of methyl (2S,5R)-1-(tert-butyloxycarbonyl)-5-(N-benzyloxy-p-nitrobenzenesulfonylamino)-piperidine-2-carboxylate The reaction was performed under the same conditions as in Example 3 except that, in Example 3 [step 1], the amounts of the compound and the solvent used in the reaction were changed to ½₀-fold amounts, the reaction temperature was changed to ° C., and the stirring time was changed to 6 hr to ensure reaction until the reaction conversion ratio reaches not less than 99%. As a result, the ratio of the 2-position isomer in the obtained reaction mixture was (2S,5R):(2R,5R)=98.3:1.7 (HPLC).

Example 10

[Step 1]
Production method of methyl (2S,5R)-1-(tert-butyloxycarbonyl)-5-(N-benzyloxy-p-nitrobenzenesulfonylamino)-piperidine-2-carboxylate The reaction was performed under the same conditions as in Example 3 except that, in Example 3 [step 1], the amounts of the compound and the solvent used in the reaction were changed to ½₀-fold amounts, the reaction temperature was changed to 65° C., and the stirring time was changed to 5 hr to ensure reaction until the reaction conversion ratio reaches not less than 99%. As a result, the ratio of the 2-position isomer in the obtained reaction mixture was (2S,5R):(2R,5R)=96.3:3.7 (HPLC).

Example 11: Step 9→Step 1

[step 9]
Production method of methyl (2S,5S)-1-(tert-butyloxycarbonyl)-5-toluenesulfonyloxy-piperidine-2-carboxylate

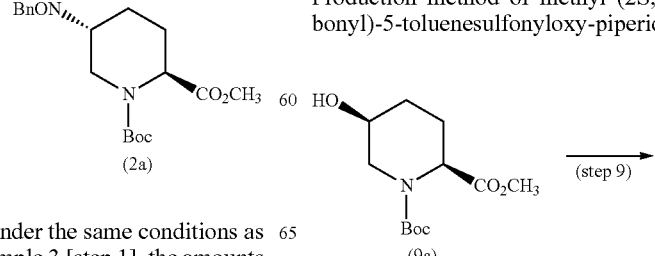

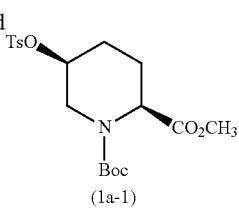

Under a nitrogen atmosphere, in a test tube, compound (9a) (1.0 g (3.86 mmol) obtained by a method similar to that in Example 1 [step 7→step 8] was dissolved in toluene (20 mL). To the obtained solution were added N,N-dimethylaminopyridine (0.94 g, 7.72 mmol) and toluenesulfonyl chloride (0.96 g, 5.02 mmol) at 25° C., and the mixture was heated and stirred at 45° C. for 2 hr. Then, N,N-dimethylaminopyridine (0.47 g, 3.86 mmol) was added and the mixture was stirred at 45° C. for 1.5 hr. Furthermore, N,N-dimethylaminopyridine (0.3 g, 1.93 mmol) was added and the mixture was stirred at 45° C. for 16 hr, and cooled to room temperature.

The obtained reaction mixture was partitioned and extracted with ethyl acetate, and the aqueous layer was discarded. The organic layer was successively washed with 10 wt % aqueous acetic acid solution and 5% sodium bicarbonate water, dried over anhydrous magnesium sulfate, and filtered.

The filtrate was concentrated, and the precipitated crystals were collected by filtration, and dried to give methyl (2S, 5S)-1-(tert-butyloxycarbonyl)-5-toluenesulfonyloxy-piperidine-2-carboxylate (hereinafter to be referred to as compound (1a-1)) as a white powder (0.53 g, yield 34.5%).

$^1$H-NMR (400 MHz, CDCl$_3$) δ 1.42-1.51 (10H, m), 1.65-1.72 (1H, m), 1.93-2.08 (1H, m), 2.25-2.28 (1H, m), 2.45 (3H, s), 2.74-2.92 (1H, dd), 3.72 (3H, s), 3.99-4.17 (1H, m), 4.34 (1H, m), 4.62-4.82 (m, 1H), 7.34-7.36 (2H, m), 7.78-7.80 (2H, m)

[Step 1]
Production method of methyl (2S,5R)-1-(tert-butyloxycarbonyl)-5-(N-benzyloxy-p-nitrobenzenesulfonylamino)-piperidine-2-carboxylate

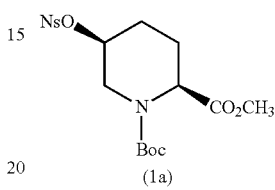

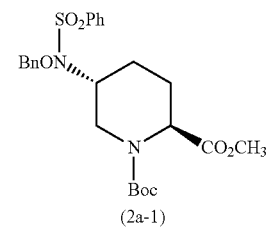

In the same manner as in Example 3 except that compound (1c) obtained in the above-mentioned [step 9] was used instead of compound (1a), the reaction was performed. After the reaction, the obtained reaction mixture was analyzed by NMR. As a result, compound (2a) was confirmed as the main resultant product.

$^1$H-NMR (400 MHz, DMSO-d$_6$) δ 1.32 (9H, s), 1.53 (1H, m), 1.73 (2H, m), 2.06 (1H, m), 3.19 (1H, m), 3.67 (4H, m), 3.89 (1H, d, J=12.0 Hz), 4.50 (1H, m), 5.04 (2H, m), 7.41 (5H, m), 8.13 (2H, m), 8.44 (2H, m)

Example 12

[Step 1]
Production method of methyl (2S,5R)-1-(tert-butyloxycarbonyl)-5-(N-benzyloxy-benzenesulfonylamino)-piperidine-2-carboxylate

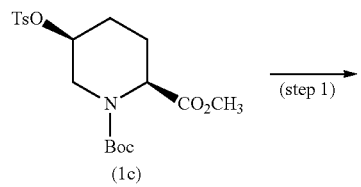

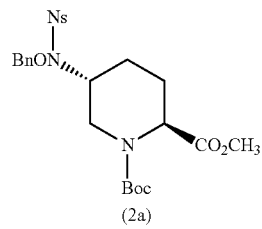

Under a nitrogen atmosphere, in a test tube, compound (1a) (300 mg, 0.68 mmol) obtained by a method similar to that in Example 1 [step 9] was dissolved in DMF (5 mL). To the obtained solution were added N-(benzyloxy)-benzenesulfonamide (213 mg, 0.81 mmol) and potassium carbonate (111.9 mg, 0.81 mmol), and the mixture was stirred at 65 HC for 26 hr. The reaction mixture was analyzed by thin layer chromatography (hereinafter to be referred to as TLC) (hexane:ethyl acetate (volume ratio)=2:1). As a result, it was confirmed that the main resultant product was methyl (2S, 5R)-1-(tert-butyloxycarbonyl)-5-(N-benzyloxy-benzenesulfonylamino)-piperidine-2-carboxylate (hereinafter to be referred to as compound (2c)). The obtained reaction mixture was extracted and washed with toluene [[TL]], and the organic layer was successively washed with 10 wt % aqueous acetic acid solution and 5 wt % aqueous sodium hydrogen carbonate solution. The organic layer was dried over anhydrous magnesium sulfate and filtered, and the solvent was evaporated to give compound (2a-1) as an oil.

Example 13

[Step 1]
Production method of methyl (2S,5R)-1-acetyl-5-(N-benzyloxy-p-nitrobenzenesulfonylamino)-piperidine-2-carboxylate

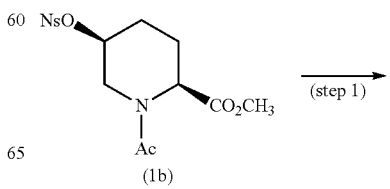

-continued

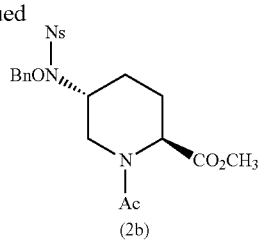

Under a nitrogen atmosphere, in a separable flask, compound (1b) (1.05 g (1.01 g in terms of pure amount, 2.62 mol) was dissolved in DMF (4 mL). To the obtained solution were added N-(p-nitrobenzenesulfonyl)-O-benzyl-hydroxylamine (0.873 g, 2.83 mmol) and potassium carbonate (0.391 g, 2.83 mmol), and the mixture was stirred for 3 hr at a reaction temperature of the inside temperature 35° C. until the reaction conversion ratio reached not less than 99%.

To the obtained reaction mixture was added toluene (9 mL) under ice-cooling and the mixture was stirred for 30 min. A 40% aqueous acetic acid solution (4 mL) was added, and the mixture was allowed to stand for partitioning. The solvent was evaporated from the obtained organic layer to give compound (2b) as a pale-yellow oil.
((2S,5R):(2R,5R)=98.8:1.2 (HPLC))

Comparative Example 1: Step 8→Step 9→Step 1

[Step 8]
Production method of methyl (2S,5S)-1-(p-nitrobenzenesulfonyl)-5-hydroxy-piperidine-2-carboxylate

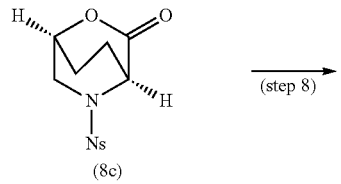

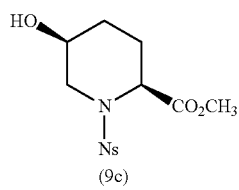

The starting material (1S,4S)-5-(p-nitrobenzenesulfonyl)-2-oxa-5-azabicyclo[2.2.2]octan-3-one (hereinafter to be referred to as compound (8c)) was synthesized according to the method described in WO 2014/200786.

Under a nitrogen atmosphere, in a 100 mL kolben, compound (8c) (2 g, 6.4 mmol) was suspended in methanol (10 mL). To the obtained suspension was added 28% sodium methoxide methanol solution (1.26 g, 6.53 mmol) under ice-cooling. After reaction for 2 hr, the reaction conversion ratio was confirmed to be not less than 99%.

To the reaction mixture was added acetic acid (0.4 mL) under ice-cooling, and the mixture was concentrated using a high vacuum diaphragm pump for 30 min. To the obtained residue was added ethyl acetate (14 mL), and the mixture was washed successively with water (6 mL) and saturated sodium hydrogen carbonate water (6 mL). The obtained organic layer was dried over magnesium sulfate (0.4 g) and filtered, and the filtrate was concentrated to give compound (9c) (2.12 g, yield 96%).

[Step 9]
Production method of methyl (2S,5R)-1-(p-nitrobenzenesulfonyl)-5-)p-nitrobenzenesulfonyloxy)-piperidine-2-carbxylate

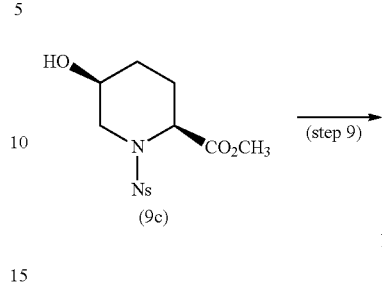

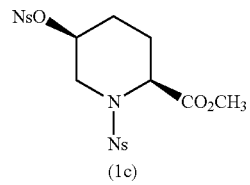

Under a nitrogen atmosphere, in a 100 mL kolben, compound (9c) (2.03 g, 5.9 mmol) obtained in the above-mentioned [step 8] was dissolved in ethyl acetate (16 mL). To the obtained solution was added triethylamine (2.12 g, 21.2 mmol) at room temperature and the mixture was stirred. Under ice-cooling, p-nitrobenzenesulfonyl chloride (2.35 g, 10.58 mmol) was added. After reaction for 4 hr, the reaction conversion ratio was confirmed to be not less than 99%.

To the obtained reaction mixture were added acetic acid (0.4 mL) and water (6 mL) under ice-cooling for washing. The obtained organic layer was concentrated to give compound (1c) (2.82 g, yield 90%).

[Step 1]
Production method of methyl (2S,5R)-1-(p-nitrobenzenesulfonyl)-5-(N-benzyloxy-p-nitrobenzenesulfonylamino)-piperidine-2-carboxylate

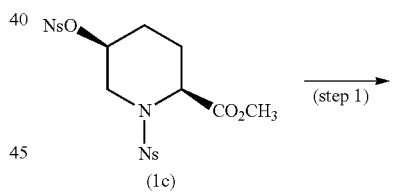

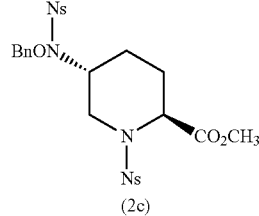

Under a nitrogen atmosphere, in a separable flask, compound (1c) (1 g, 1.88 mmol) obtained in the above-mentioned [step 9] was dissolved in DMF (4 mL). To the obtained solution were added N-(p-nitrobenzenesulfonyl)-O-benzyl-hydroxylamine (0.626 g, 2.03 mmol) and potassium carbonate (0.281 g, 2.03 mmol), and the mixture was stirred for 102 hr at a reaction temperature of the inside temperature 35° C. until the reaction conversion ratio reached not less than 99%. The ratio of the 2-position isomer in the obtained reaction mixture was (2S,5R):(2R,5R)=63:37 (HPLC).

To the obtained reaction mixture was added toluene (5 mL) under ice-cooling and the mixture was stirred for 30 min. A 40% aqueous acetic acid solution (4 mL) was added, and the mixture was allowed to stand for partitioning. The solvent was evaporated from the obtained organic layer to give crude compound (2c) as a pale-yellow oil.

Comparative Example 2

[Step 1]
Production method of methyl (2S,5R)-1-(p-nitrobenzenesulfonyl)-5-(N-benzyloxy-p-nitrobenzenesulfonylamino)-piperidine-2-carboxylate

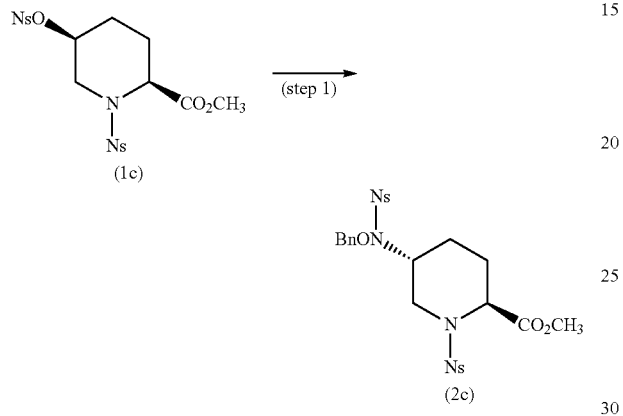

In the same manner as in Comparative Example 1 [step 1] except that the reaction temperature was changed from 35° C. to ° C. and the reaction time was changed from 102 hr to 6 hr, experiment was performed to give compound (2c) as a pale-yellow oil.

The ratio of the 2-position isomer in the obtained reaction mixture was (2S,5R):(2R,5R)=53:47 (HPLC).

Comparative Example 3: Step 9→Step 1

[Step 9]
Production method of methyl (2S,5S)-1-trifluoroacetyl-5-(p-nitrobenzenesulfonyloxy)-piperidine-2-carboxylate

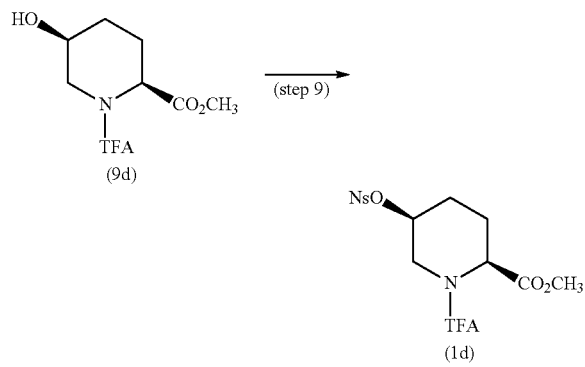

The starting material methyl (2S,5S)-1-(trifluoroacetyl)-(hereinafter to be referred to as compound (9d)) was synthesized according to the method described in WO 2013/180197.

Under a nitrogen atmosphere, in a kolben, compound (9d) (14.5 g, 56.2 mmol) was dissolved in ethyl acetate (115 mL). To the obtained solution was added triethylamine (20.5 g, 202 mmol), and p-nitrobenzenesulfonyl chloride (22.7 g, 101 mmol) was added under ice-cooling. After reaction for 3 hr, the reaction conversion ratio was confirmed to be not less than 99%.

To the obtained reaction mixture were added acetic acid (4.7 mL) and water (43 mL) under ice-cooling. After washing, the obtained organic layer was washed twice with saturated sodium hydrogen carbonate water (43 mL) and further washed with water (14 mL). The organic layer was concentrated to give compound (1d) (24.6 g, yield 99%).

[Step 1]
Production method of methyl (2S,5R)-1-trifluoroacetyl-5-(N-benzyloxy-p-nitrobenzenesulfonylamino)-piperidine-2-carboxylate

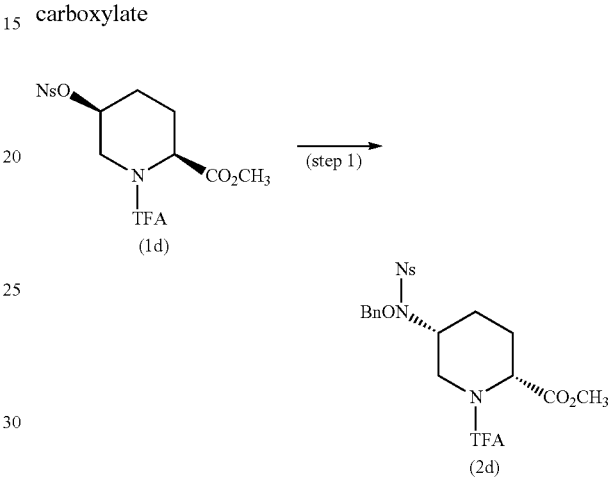

Under a nitrogen atmosphere, in a separable flask, compound (1d) (1.11 g (1.01 g in terms of pure amount, 2.29 mmol) obtained in the above-mentioned [step 9] was dissolved in DMF (4 mL). To the obtained solution were added N-(p-nitrobenzenesulfonyl)-O-benzyl-hydroxylamine (0.763 g, 2.47 mmol) and potassium carbonate (0.342 g, 2.47 mmol), and the mixture was stirred for 21 hr at a reaction temperature of the inside temperature 35° C. until the reaction conversion ratio reached not less than 99%. The ratio of the 2-position isomer in the obtained reaction mixture was (2S,5R):(2R,5R)=92:8 (HPLC).

To the obtained reaction mixture was added toluene (5 mL) under ice-cooling and the mixture was stirred for 30 min. A 40% aqueous acetic acid solution (4 mL) was added, and the mixture was allowed to stand for partitioning. The solvent was evaporated from the obtained organic layer to give compound (2d) as a pale-yellow oil.

Comparative Example 4

[Step 1]
Production method of methyl (2S,5R)-1-trifluoroacetyl-5-(N-benzyloxy-p-nitrobenzenesulfonylamino)-piperidine-2-carboxylate

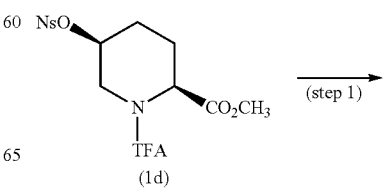

-continued

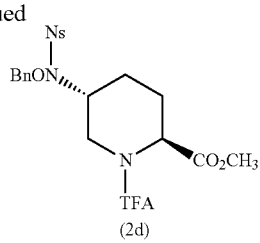

In the same manner as in Comparative Example 3 [step 1] except that the reaction temperature was changed from 35° C. to ° C. and the reaction time was changed from 21 hr to 2 hr, experiment was performed to give compound (2d) as a pale-yellow oil.

The ratio of the 2-position isomer in the obtained reaction mixture was (2S,5R):(2R,5R)=80:20 (HPLC).

TABLE 2

| | $PG^1$ | [step 1] reaction temperature (° C.) | compound (2) ratio of 2-position isomer | |
|---|---|---|---|---|
| | | | 2S,5R (%) | 2R,5R (%) |
| Example 7 | Boc | 25 | 99.3 | 0.7 |
| Example 3 | Boc | 35 | 99.2 | 0.8 |
| Example 8 | Boc | 45 | 98.5 | 1.5 |
| Example 9 | Boc | 55 | 98.3 | 1.7 |
| Example 10 | Boc | 65 | 96.3 | 3.7 |
| Example 13 | Ac | 35 | 98.8 | 1.2 |
| Example 6 | Ac | 65 | 91.2 | 8.8 |
| Comparative Example 1 | Ns | 35 | 63 | 37 |
| Comparative Example 2 | Ns | 65 | 53 | 47 |
| Comparative Example 3 | TFA | 35 | 92 | 8 |
| Comparative Example 4 | TFA | 65 | 80 | 20 |

The results of Examples 3, 6-10 and 13, and Comparative Examples 11-14 are collectively shown in Table 2.

As is clear from Table 2, when $PG^1$ is a protecting group with high electron-withdrawing property such as Ns, TFA, the ratio of the 2-position isomer (2R,5R) of compound (2) tended to be high. When the reaction temperature is high, the ratio of the 2-position isomer (2R,5R) of compound (2) tended to be high.

INDUSTRIAL APPLICABILITY

The method of the present invention is a method for producing a (2S,5R)-5-(protected oxyamino)-piperidine-2-carboxylic acid derivative at a low cost that can be performed under mild reaction conditions not requiring a facility at an extremely low temperature, is safer, can control the quality of the desired product with ease, and shows good workability in the site of production.

This application is based on patent application No. 2018-177774 filed in Japan, the contents of which are encompassed in full herein.

The invention claimed is:

1. A method for producing a compound represented by the formula (1):

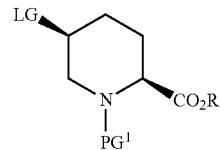

wherein LG is a leaving group, $PG^1$ is an amino-protecting group, and R is a hydrocarbon group having 1-8 carbon atoms and optionally having substituent(s), comprising reacting a compound represented by the formula (6):

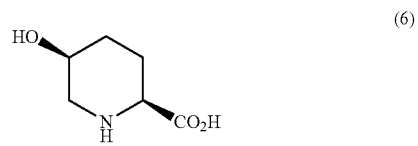

with an amino group protecting agent to obtain a compound represented by the formula (7):

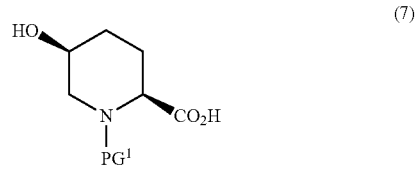

wherein each symbol is as defined above, or a salt thereof;

reacting the aforementioned compound represented by the formula (7) with a lactonization agent to obtain a compound represented by the formula (8):

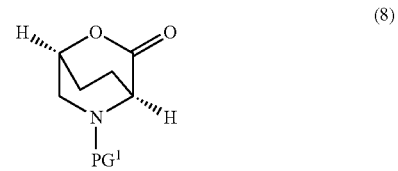

wherein each symbol is as defined above;

reacting the aforementioned compound represented by the formula (8) with an esterification agent to obtain a compound represented by the formula (9):

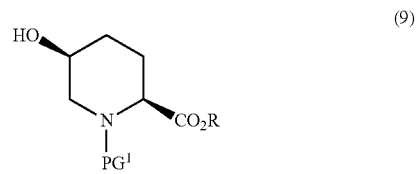

wherein each symbol is as defined above; and reacting the aforementioned compound represented by the formula (9) with a leaving group introduction agent.

2. A method for producing a compound represented by the formula (1):

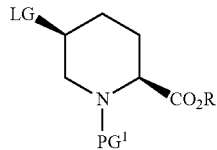
(1)

wherein LG is a leaving group, $PG^1$ is an amino-protecting group, and R is a hydrocarbon group having 1-8 carbon atoms and optionally having substituent(s), comprising
reacting a compound represented by the formula (8):

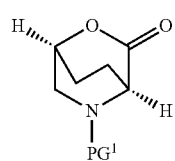
(8)

wherein $PG^1$ is as defined above,
with an esterification agent to give a compound represented by the formula (9):

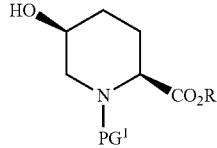
(9)

wherein each symbol is as defined above; and
reacting the aforementioned compound represented by the formula (9) with a leaving group introduction agent.

3. A compound represented by the following formula (1a) or (1b):

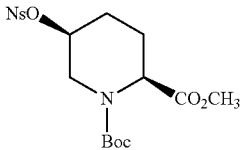
(1a)

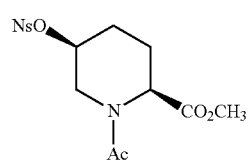
(1b)

wherein
Boc is a tert-butoxycarbonyl group,
Ac is an acetyl group, and
Ns is a p-nitrobenzenesulfonyl group.

* * * * *